United States Patent
Carlson et al.

(10) Patent No.: US 11,117,869 B2
(45) Date of Patent: Sep. 14, 2021

(54) COMPOUNDS, COMPOSITIONS AND METHODS FOR TREATMENT OF MYOPIA

(71) Applicant: Aerie Pharmaceuticals, Inc., Bedminster, NJ (US)

(72) Inventors: Eric Carlson, Irvine, CA (US); Mitchell A. deLong, Chapel Hill, NC (US); Heeren Gordhan, Durham, NC (US); Cynthia L. Lichorowic, Raleigh, NC (US); Jill M. Sturdivant, Chapel Hill, NC (US)

(73) Assignee: Aerie Pharmaceuticals, Inc., Bedminster, NJ (US)

( * ) Notice: Subject to any disclaimer, the term of this patent is extended or adjusted under 35 U.S.C. 154(b) by 0 days.

(21) Appl. No.: 16/779,188

(22) Filed: Jan. 31, 2020

(65) Prior Publication Data

US 2020/0247760 A1 Aug. 6, 2020

Related U.S. Application Data

(60) Provisional application No. 62/819,236, filed on Mar. 15, 2019, provisional application No. 62/801,515, filed on Feb. 5, 2019, provisional application No. 62/800,312, filed on Feb. 1, 2019.

(51) Int. Cl.
| | |
|---|---|
| *C07D 471/08* | (2006.01) |
| *C07D 239/26* | (2006.01) |
| *C07D 213/40* | (2006.01) |
| *A61K 9/00* | (2006.01) |
| *C07D 409/12* | (2006.01) |
| *C07D 213/30* | (2006.01) |
| *C07D 405/12* | (2006.01) |

(52) U.S. Cl.
CPC .......... *C07D 239/26* (2013.01); *A61K 9/0048* (2013.01); *C07D 213/30* (2013.01); *C07D 213/40* (2013.01); *C07D 405/12* (2013.01); *C07D 409/12* (2013.01); *C07D 471/08* (2013.01)

(58) Field of Classification Search
CPC ..................................................... C07D 471/08
See application file for complete search history.

(56) References Cited

FOREIGN PATENT DOCUMENTS

ES 2526580 * 1/2015

OTHER PUBLICATIONS

Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice, pp. 949-982, 1996.*

* cited by examiner

*Primary Examiner* — Patricia L Morris
(74) *Attorney, Agent, or Firm* — K&L Gates LLP; Louis C. Cullman; Benjamin D. Heuberger

(57) ABSTRACT

Provided herein are 8-methyl-8-azabicyclo[3.2.1]octan-3-yl and pyridin-4-ylmethanyl ester and amide compounds and compositions. Also provided herein are methods of preventing or delaying the onset of myopia in a subject in need thereof, comprising administering the compounds or compositions provided herein to the subject. Also provided herein are methods of reducing or preventing the progression of myopia in a subject in need thereof, comprising administering the compounds or compositions provided herein to the subject.

2 Claims, 3 Drawing Sheets

COMPOUNDS, COMPOSITIONS AND METHODS FOR TREATMENT OF MYOPIA

RELATED APPLICATIONS

This application claims priority of U.S. Provisional Patent Application No. 62/800,312, filed Feb. 1, 2019, U.S. Provisional Patent Application No. 62/801,515, filed Feb. 5, 2019, and U.S. Provisional Patent Application No. 62/819,236, filed Mar. 15, 2019, the entire content of each of which are incorporated herein by reference.

TECHNICAL FIELD

Provided herein are 8-methyl-8-azabicyclo[3.2.1]octan-3-yl and pyridin-4-ylmethanyl ester and amide compounds and compositions. Also provided herein are methods of preventing or delaying the onset of myopia in a subject in need thereof, comprising administering the compounds or compositions provided herein to the subject. Also provided herein are methods for reducing or preventing the progression of myopia in a subject in need thereof, comprising administering the compounds or compositions provided herein to the subject.

BACKGROUND

Myopia, otherwise known as, nearsightedness or short sightedness, is a type of refractive error of the eye, in which the visual image is focused in front of the retina, typically resulting in blurred vision of distant objects. Myopia is especially prevalent among Asians and has been reported to be as high as 70-90% in Asian countries. Myopia may be corrected by prescription lenses (for example, spectacles or contact lenses) or refractive surgery (for example, LASIK or phakic intraocular lens implantation). Additionally, patients having a higher degree of myopia are at a higher risk of developing sight threatening disorders such as degenerative retina changes such as peripheral lattice changes, tears and detachment, myopic choroidal neo-vascularization, myopic macular schists and holes, posterior staphylomas, myopic macular degeneration, early-onset cataracts (in the 30 s-40 s), open angle glaucoma, and peri-papillary atrophy, optic disc tilt and pits. These disorders, if left untreated, may result in visual loss later in life. Children with early onset myopia are also more likely to eventually develop high myopia. A recent Singapore-based paper pooling data from, the Singapore, Chinese, Indian and Malaysian adult studies showed that pathological symptoms of myopia, in particular staphyloma and chorioretinal atrophy, worsened with the progression of age, myopic refraction and axial length (Chang et al (2013)). As such, compounds, or compositions capable of slowing the development and/or progression of myopia of a patient in childhood, so that the eventual myopia, if it develops, would be less than it would have been (e.g., –5.00 D rather than –10.00 D), would have a major beneficial impact on the life of the patient.

BRIEF SUMMARY

This application relates to compounds, and compositions thereof, to prevent or delay onset of myopia, if given before myopia occurs, or preventing or reducing the progression of myopia, if present. While not wishing to be bound by theory, it is thought that these compounds work by antagonizing one or more of the family of muscarinic receptors. Although much work had been done in the area of muscarinic receptors, common side effects such as blurred vision, and a lack of truly selective antagonists remain.

In one aspect, provided herein are compounds of Formula I:

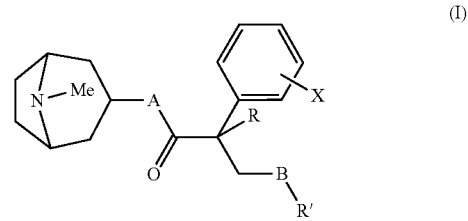

(I)

or a polymorph, zwitterion, solvate, or a pharmaceutically acceptable salt thereof,
wherein R and R' are, independently, H or lower alkyl, A and B are, independently, $CH_2$, $NR^1$, or O, $R^1$ is H or lower alkyl, and X is hydrogen, hydroxyl, halogen, $C_1$-$C_4$ alkyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl. The attachment of the heteroatom to the 8-methyl-8-azabicyclo[3.2.1]octan-3-yl system may be either endo or exo, provided that when the configuration is endo, then R and R' cannot both be hydrogen and A be oxygen at the same time.

In another aspect, provided herein are compounds of Formula II:

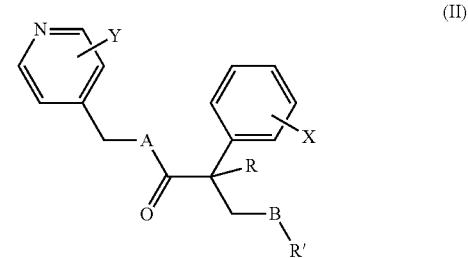

(II)

or a polymorph, zwitterion, solvate, or a pharmaceutically acceptable salt thereof,
wherein R and R' are, independently, H or lower alkyl, A and B are, independently, $CH_2$, $CF_3$, $CF_2H$, $NR^1$, or O, $R^1$ is H or lower alkyl, and X and Y are, independently, hydrogen, hydroxyl, halogen, $C_1$-$C_4$ alkyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl.

In yet another aspect, provided herein are compounds of Formula III:

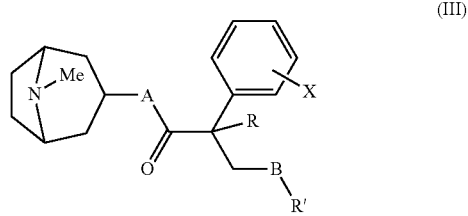

(III)

or a polymorph, zwitterion, solvate, or a pharmaceutically acceptable salt thereof,
wherein R and R' are, independently, H or lower alkyl, A and B are, independently, CH$_2$, NR$^1$, or O, R$^1$ is H or lower alkyl, and X is hydrogen, hydroxyl, halogen, C$_1$-C$_4$ alkyl, amino, nitro, cyano, C$_1$-C$_4$ carbonyl, C$_1$-C$_4$ carbonylamino, C$_1$-C$_4$ alkoxy, C$_1$-C$_4$ sulfonyl, C$_1$-C$_4$ sulfonylamino, C$_1$-C$_4$ thioalkyl or C$_1$-C$_4$ carboxyl. The attachment of the heteroatom to the 8-methyl-8-azabicyclo[3.2.1]octan-3-yl system may be either endo or exo.

In still another aspect, provided herein are compounds of Formula IV:

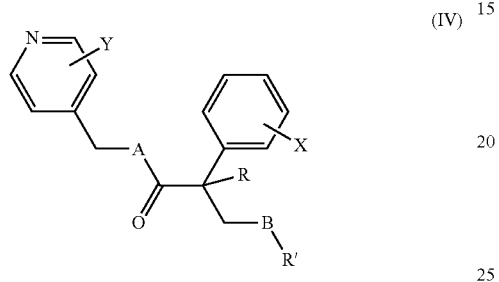

(IV)

or a polymorph, zwitterion, solvate, or a pharmaceutically acceptable salt thereof,
wherein R and R' are, independently, H or lower alkyl, A and B are, independently, CH$_2$, CF$_3$, CF$_2$H, NR$^1$, or O, R$^1$ is H or lower alkyl, and X and Y are, independently, hydrogen, hydroxyl, halogen, C$_1$-C$_4$ alkyl, amino, nitro, cyano, C$_1$-C$_4$ carbonyl, C$_1$-C$_4$ carbonylamino, C$_1$-C$_4$ alkoxy, C$_1$-C$_4$ sulfonyl, C$_1$-C$_4$ sulfonylamino, C$_1$-C$_4$ thioalkyl or C$_1$-C$_4$ carboxyl.

In yet another aspect, provided herein are compositions comprising: a compound of Formula (I), a compound of Formula (II), a compound of Formula (III), a compound of Formula (IV), benzeneacetic acid, α-(hydroxymethyl)-(3-endo)-8-methyl-8-azabicyclo[3.2.1]oct-3-yl ester, (αR)-benzeneacetic acid, α-(hydroxymethyl)-(3-endo)-8-methyl-8-azabicyclo[3.2.1]oct-3-yl ester, (αS)-benzeneacetic acid, α-(hydroxymethyl)-(3-endo)-8-methyl-8-azabicyclo[3.2.1]oct-3-yl ester, endo-benzeneacetic acid, α-(hydroxymethyl)-8-(methyl-d$_3$)-8-azabicyclo[3.2.1]oct3-yl ester,

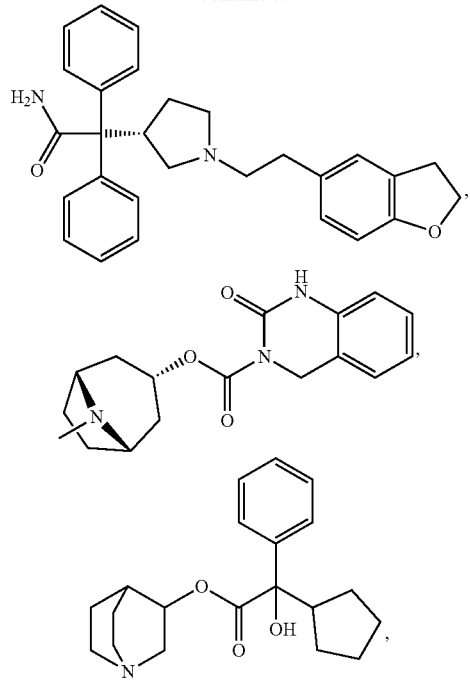

the (3R,2'R)-enantiomer of EA-3167,

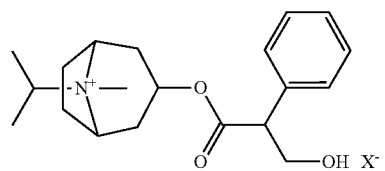

wherein X is Cl, Br or I,

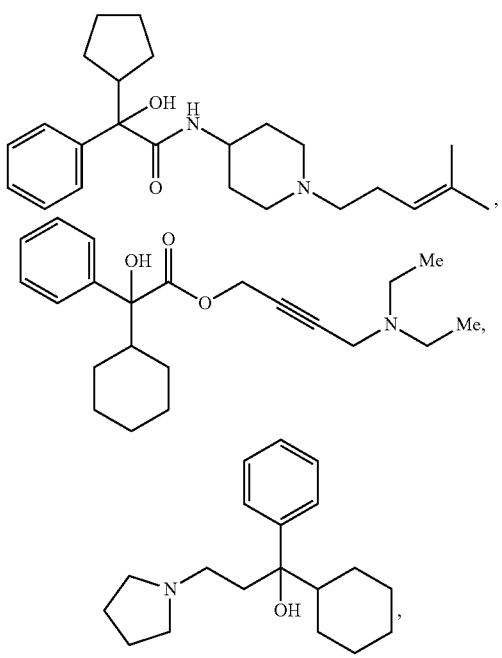

-continued

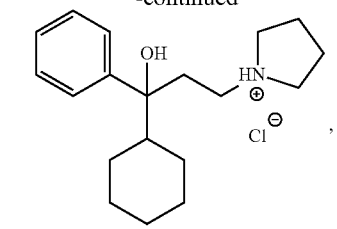

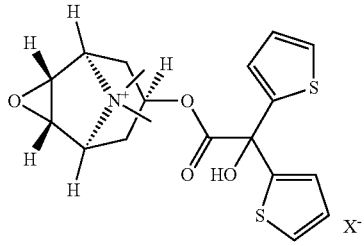

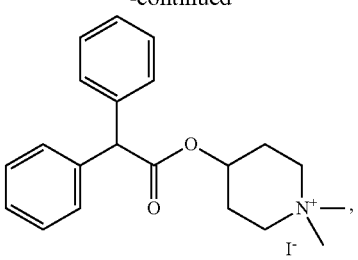

wherein X is Cl, Br or I,

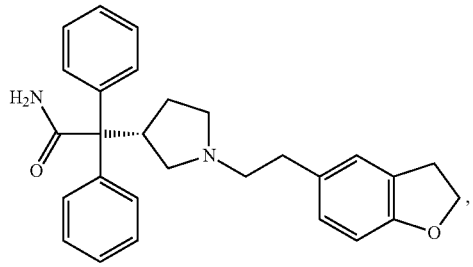

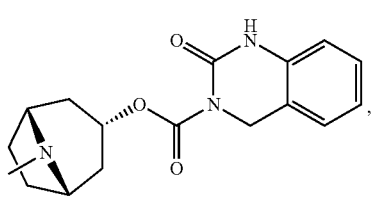

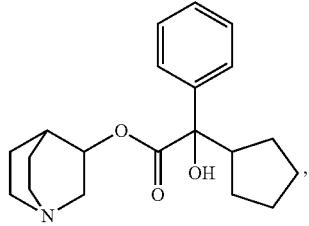

or a polymorph, zwitterion, solvate, or a pharmaceutically acceptable salt thereof or a combination thereof; and a pharmaceutically acceptable vehicle.

In another aspect, compositions are provided comprising: a compound of Formula (I), a compound of Formula (II), a compound of Formula (III), a compound of Formula (IV), benzeneacetic acid, α-(hydroxymethyl)-(3-endo)-8-methyl-8-azabicyclo[3.2.1]oct-3-yl ester, (αR)-benzeneacetic acid, α-(hydroxymethyl)-(3-endo)-8-methyl-8-azabicyclo[3.2.1] oct-3-yl ester, (αS)-benzeneacetic acid, α-(hydroxymethyl)-(3-endo)-8-methyl-8-azabicyclo[3.2.1]oct-3-yl ester, endo-benzeneacetic acid, α-(hydroxymethyl)-8-(methyl-d$_3$)-8-azabicyclo[3.2.1]oct-3-yl ester, the (3R,2'R)-enantiomer of EA-3167,

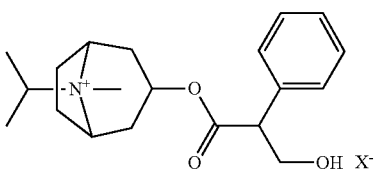

wherein X is Cl, Br or I,

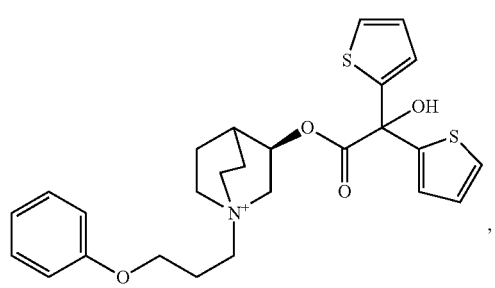

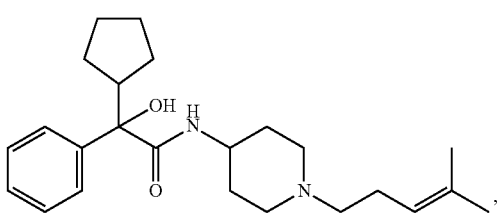

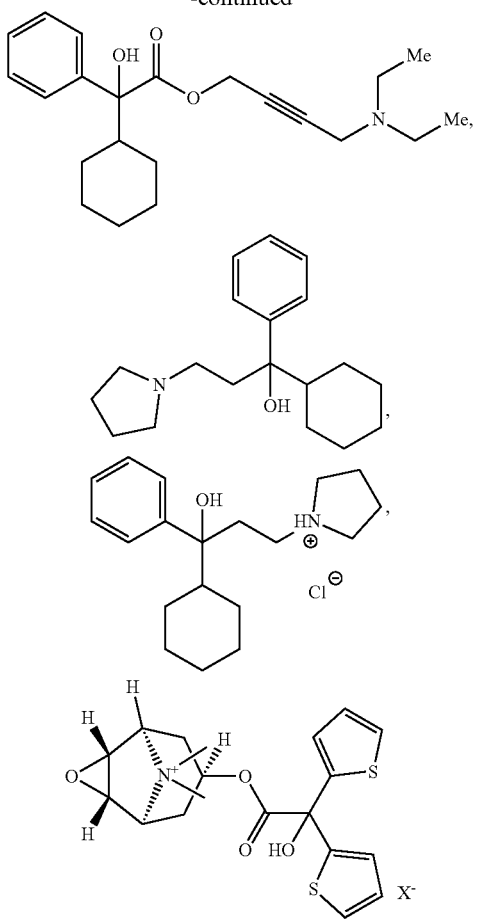

wherein X is Cl, Br or I,

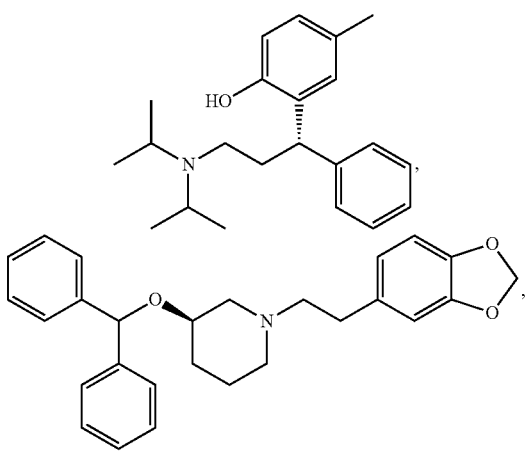

or a polymorph, zwitterion, solvate, or a pharmaceutically acceptable salt thereof, or a combination thereof; and a non-aqueous solvent. Suitable compounds can be also found in the publication *Archiv der Pharmazie* (Weinheim, Germany) Volume 306 Issue 12 Pages 943-7 1973, and are herein incorporated by reference. In addition, some natural products will be found to possess the necessary structures, one example is *Dokladi na Bulgarskata Akademiya na Naukite* Volume 57 Issue 5 Pages 41-44, 2004, but all natural products encompassed by Formula III and IV are specifically contemplated.

In yet another aspect, this disclosure provides a method for preventing or delaying the onset of myopia comprising administering to a subject in an eye a composition comprising less than 0.1% of the compounds of Formula III or Formula IV. In some embodiments, the compound is present in the form of a pharmaceutically-acceptable salt. In some embodiments, the composition comprises about 0.01% of a compound of Formula III or Formula IV. In some embodiments, wherein the composition comprises about 1.0% to 0.0049% of a compound of Formula III or Formula IV. In some embodiments, the subject is a human being, between 4 and 21 years old. In some embodiments, the subject is the subject is a human being, between 5 and 10 years old. In some embodiments, the subject has pre-myopia. In some embodiments, the composition of a compound of Formula III or Formula IV is administered every other day, or at least once daily, or at least twice daily. In some embodiments, each administration is performed by instilling at least one drop, at least two drops, or at least three drops to each eye, wherein each drop contains about 20-100 microliter of the composition. In some embodiments, the administration continues for at least six months, or at least one year, or at least two years, or at least 10 years or longer. In some embodiments, the composition further comprises a non-aqueous formulation. In some embodiments, the composition further comprises a non-aqueous formulation that contains one or more partially fluorinated hydrocarbons (these are also known as semi-fluorinated alkanes, or SFAs). In some embodiments, at least one pharmaceutically acceptable excipient is selected from the group consisting of benzalkonium chloride. In some embodiments, benzalkonium chloride is present in the composition at a concentration of about 0.01%. In some embodiments, no preservative excipients are present in the composition. In some embodiments, the Spherical Equivalent (SE) of the eye is within the range of from ~1.00 D to −0.49 D before administration of the composition. In some embodiments, the SE is measured by Autorefractor after administration of cycloplegia. In some embodiments, the subject has no astigmatism or has astigmatism of not more than 1.50 D as measured by cycloplegic or non-cycloplegic autorefraction before administration of the composition. In some embodiments, the pupil of the eye has no dilation or a dilation of no greater than 2 mm, e.g., no greater than 1.9 mm, no greater than 1.8 mm, no greater than 1.7 mm, no greater than 1.5 mm, no greater than 1.49 mm during the period of administration of the composition. In some embodiments, the eye has no clinically significant loss of accommodation or experience a loss of accommodation of no greater than 10 D, e.g., no greater than 9 D, no greater than 8.5 D, no greater than 8.8 D, or no greater than 8 D. In some embodiments, the eye has no clinically significant loss of near visual acuity from loss of accommodation. In some embodiments, wherein the onset of myopia is delayed for greater than 6 months, 12 months, 18 months, two years, three years, five years, six years, eight years, or longer. In another aspect, this disclosure provides a method for reducing or preventing myopia progression comprising administering to a subject in an eye the composition of a compound of Formula III or Formula IV, wherein the composition is administered no more frequently than once every two days, once every three days, or once every four days. In some embodiments, each administration is performed by instilling at least one drop, at least two drops, or at least three drops to the eye, wherein each, drop contains about 20-100 microliters of liquid. In some embodiments, the SE of the eye is less than −1.50 D before administration of the composition. In some embodiments, the SE of the eye is within the range of from −0.50 D to −1.50 D before administration of the composition. In some embodiments, the subject is between 4 to 21 years old. In some embodiments, the subject is between 5 and 9 years old. In some embodiments, the composition of a compound of Formula III or Formula IV is presented in perfluorohexyloctane. In some embodiments, the composition of a compound of Formula III or Formula IV, presented in perfluorohexyloctane, comprises about 0.1% to 0.0049% a compound of Formula III or Formula IV, In some embodiments, the composition further comprises at least one pharmaceutically acceptable excipient. In some embodiments, the at least one pharmaceutically acceptable excipient is selected from ethyl alcohol.

In some embodiments, the composition of Formula III and IV further comprises an additional therapeutic agent, or a polymorph, zwitterion, solvate, or pharmaceutically acceptable salt of such additional therapeutic agent. In some embodiments, the composition of Formula III and IV further comprises at least one additional therapeutic agent that is a known muscarinic receptor antagonist. In some embodiments, the composition of Formula III and IV further comprises one or more additional active(s) that is a known muscarinic receptor antagonist, chosen from the list:

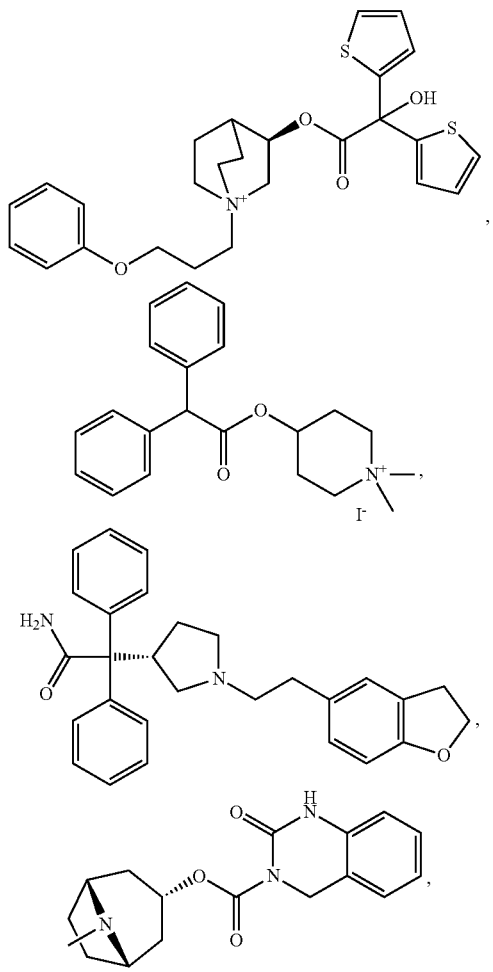

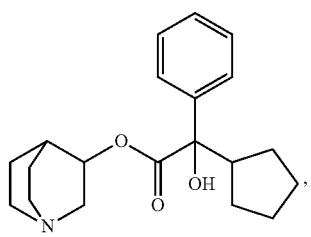

the (3R,2'R)-enantiomer of EA-3167,

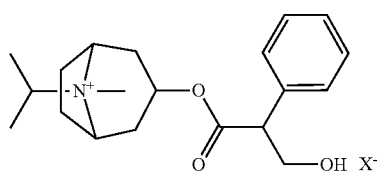

wherein X is Cl, Br or I,

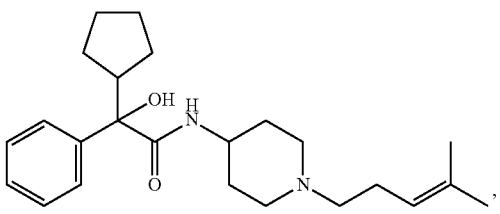

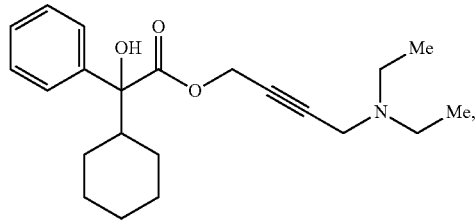

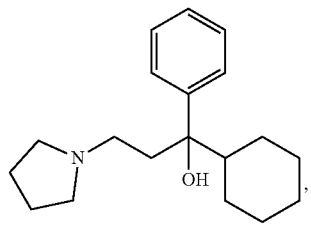

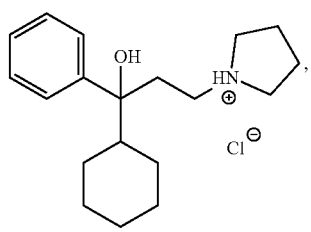

-continued

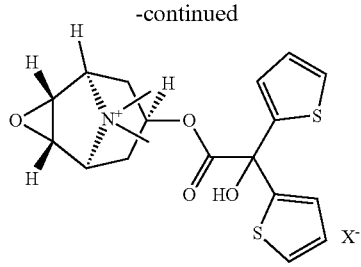

wherein X is Cl, Br or I,

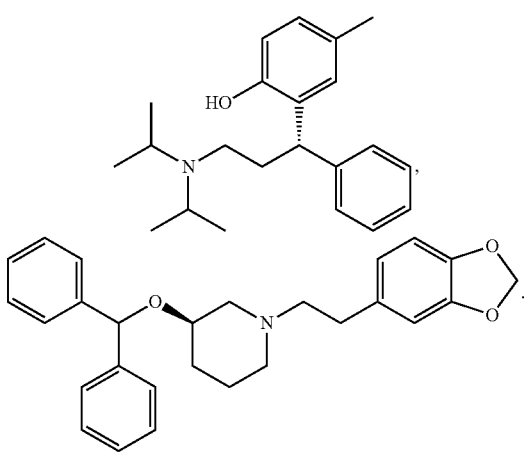

When used with another agent.

In some embodiments, the mean change of SE during a two-year period following the start of administration of the composition is reduced by at least 20% as compared to controls. In some embodiments, treating a patient, e.g., a patient having pre-myopia, reduces the change in refraction by at least 10%, at least 20%, at least 30%, or at least 40%, or at least 50%. In some embodiments, treating a patient having pre-myopia with a composition comprising a compound of Formula III or Formula IV, reduces the further increase of the axial length by at least 10%, at least 15%, at least 20%, at least 30% over a period of 1 week, 2 weeks, 1 month, 2 months, 6 months, one year, two years or more from or more, from the initiation of the treatment. In some embodiments, treating a patient having pre-myopia, with the composition with a composition comprising a compound of Formula III or Formula IV, disclosed herein, can reduce change in refraction by at least 10%, at least 20%, at least 30%, or at least 40%.

In some embodiments, administration of the composition comprising a compound of Formula III or Formula IV, disclosed herein reduces the change in refraction (i.e., myopic refractive error shift) by at least 10%, e.g., at least 20%, at least 30%, or at least 40%, at least 50%, as compared to controls. In some embodiments, during treatment the pupil of the eye of the patient evinces no dilation or a dilation of no greater than 1.9 mm, no greater than 1.8 mm, no greater than 1.7 mm, no greater than 1.5 mm, no greater than 1.49 mm during the period of administration of the composition comprising a compound of Formula III or Formula IV. In some embodiments, the eye has no loss of accommodation or a loss of accommodation of no greater than 10 D, e.g., no greater than 9 D, no greater than 8.5 D, no greater than 8.8 D, or no greater than 8 D.

Also provided in this disclosure is a use of a compound of Formula III or Formula IV in the preparation of a composition for preventing or delaying the onset of myopia progression and the composition comprises a partially fluorinated hydrocarbon as the carrier. A compound of Formula III can also be used to treat a number of other ocular diseases such as uveitis and early amblyopia.

DETAILED DESCRIPTION

Figure 1:
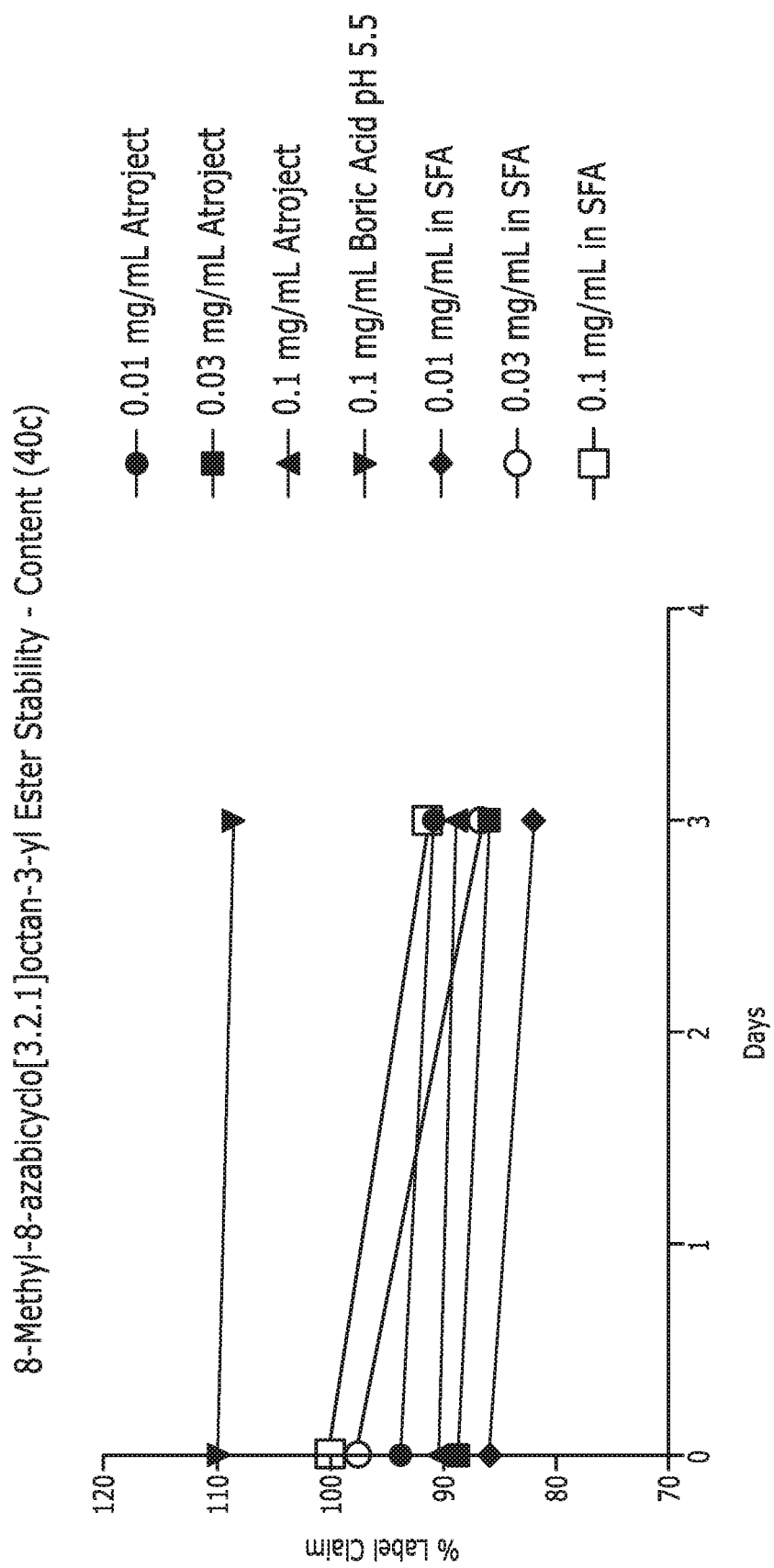
FIG. 1 shows the superior stability of the SFA formulation of Table 8 as compared to aqueous formulations for other compounds provided herein.

Publications and patents are referred to throughout this disclosure. All U.S. Patents or U.S. Patent Application Publications cited herein are hereby incorporated by reference. All percentages, ratios, and proportions used herein are percent by weight unless otherwise specified.

8-methyl-8-azabicyclo[3.2.1]octan-3-yl and pyridin-4-yl-methanyl esters and amides are provided. Compositions and methods of treating myopia are provided.

"Alkyl" refers to a saturated aliphatic hydrocarbon including straight chain and branched chain groups (e.g., $C_1$-$C_{20}$ alkyl, $C_1$-$C_{10}$ alkyl, or $C_1$-$C_4$ alkyl). "Alkyl" may be exemplified by groups such as methyl, ethyl, n-propyl, isopropyl, n-butyl and the like. Alkyl groups may be substituted or unsubstituted. Substituents may also be themselves substituted. When substituted, the substituent group is preferably but not limited to $C_1$-$C_4$ alkyl, aryl, amino, cyano, halogen, alkoxy or hydroxyl. "$C_1$-$C_4$ alkyl" refers to alkyl groups containing one to four carbon atoms.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. Substituents may also be themselves substituted. When substituted, the substituent group is preferably alkyl, halogen or alkoxy. Substituents may also be themselves substituted. Substituents be placed on the alkene itself and also on the adjacent member atoms or the alkynyl moiety. "$C_2$-$C_4$ alkenyl" refers to alkenyl groups containing two to four carbon atoms.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. When substituted, the substituent group is preferably alkyl, amino, cyano, halogen, alkoxyl or hydroxyl. Substituents may also be themselves substituted. Substituents are not on the alkyne itself but on the adjacent member atoms of the alkynyl moiety. "$C_2$-$C_4$ alkynyl" refers to alkynyl groups containing two to four carbon atoms.

"Acyl" or "carbonyl" refers to the group —C(O)R wherein R is alkyl, alkenyl, alkynyl, aryl, heteroaryl, carbocydic, heterocarbocyclic, alkylaryl or alkylheteroaryl.

Alkylcarbonyl refers to a group wherein the carbonyl moiety is preceded by an alkyl chain of 1-4 carbon atoms.

"Alkoxy" refers to the group —O—R wherein R is acyl, alkyl alkenyl, alkyl alkynyl, aryl, carbocyclic, heterocarbocyclic, heteroaryl, $C_1$-$C_4$ alkyl aryl or $C_1$-$C_4$ alkyl heteroaryl.

"Amino" refers to the group —NR'R' wherein each R' is, independently, hydrogen, amino, hydroxyl, alkoxyl, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring. The R' groups may themselves be further substituted, in which case the group also known as guanidyl is specifically contemplated under the term "amino".

"Aryl" refers to an aromatic carbocyclic group. "Aryl" may be exemplified by phenyl. The aryl group may be substituted or unsubstituted. Substituents may also be themselves substituted. When substituted, the substituent group is preferably but not limited to heteroaryl; acyl, carboxyl, carbonylamino, nitro, amino, cyano, halogen, or hydroxyl.

"8-methyl-8-azabicyclo[3.2.1]octan-3-yl" refers to the bicyclic heteroaliphatic ring structure:

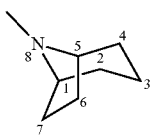

with the systematic numbering as shown, wherein the bicyclic ring is attached to the remainder of the molecule via Carbon 3, in either an endo, or an exo configuration, or a mixture of the two.

"Pyridin-4-ylmethanyl" refers to the heteroaromatic ring structure:

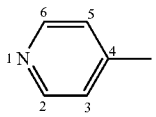

with the systematic numbering shown, wherein the ring system is attached to the remainder of the molecule via attachment to the methyl which itself is attached to the ring at the 4-position.

"Carboxyl" refers to the group —C(=O)O—$C_1$-$C_4$ alkyl.

"Carbonyl" refers to the group —C(O)R wherein each R is, independently, hydrogen, alkyl, aryl, cycloalkyl; heterocycloalkyl; heteroaryl, $C_1$-$C_4$ alkyl aryl or $C_1$-$C_4$ alkyl heteroaryl.

"Carbonylamino" refers to the group —C(O)NR'R' wherein each R' is, independently, hydrogen, alkyl, aryl, cycloalkyl; heterocycloalkyl; heteroaryl, $C_1$-$C_4$ alkyl aryl or $C_1$-$C_4$ alkyl heteroaryl. The two R' groups may themselves be linked to form a ring.

"Alkylaryl" refers to alkyl groups having an aryl substituent such that the aryl substituent is bonded through an alkyl group. "Alkylaryl" may be exemplified by benzyl.

"Alkylheteroaryl" refers to alkyl groups having a heteroaryl substituent such that the heteroaryl substituent is bonded through an alkyl group.

"Carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. Substituents may also be themselves substituted. Preferred carbocyclic groups include cydopropyl, cyclobutyl, cyclopentyl, cyclohexyl, cyclohexenyl, and cycloheptyl. More preferred carbocyclic groups include cyclopropyl and cyclobutyl. The most preferred carbocyclic group is cyclopropyl. Carbocyclic groups are not aromatic.

"Halogen" refers to fluoro, chloro, bromo or iodo moieties. Preferably, the halogen is fluoro, chloro, or bromo.

"Heteroaryl" or "heteroaromatic" refers to a monocyclic or bicyclic aromatic carbocyclic radical having one or more heteroatoms in the carbocyclic ring. Heteroaryl may be substituted or unsubstituted. When substituted, the substituents may themselves be substituted. Preferred but non-limiting substituents are aryl; $C_1$-$C_4$ alkylaryl; amino; halogen, hydroxy, cyano, nitro; carboxyl; carbonylamino or $C_1$-$C_4$ alkyl. Preferred heteroaromatic groups include isoquinolinyl, benzoisothiazolyl, benzoisothiadiazolyl, benzothiofuranyl, thienyl, furanyl, tetrazoyl, triazolyl, and pyridyl.

"Heteroatom" means an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups are not aromatic.

"Hydroxy" or "hydroxyl" means a chemical entity that consists of —OH. Alcohols contain hydroxy groups. Hydroxy groups may be free or protected. An alternative name for hydroxyl is hydroxyl.

"Linker" means a linear chain of n member atoms where n is an integer of from 1 to 4.

"Member atom" means a carbon, nitrogen, oxygen or sulfur atom. Member atoms may be substituted up to their normal valence. If substitution is not specified the substituents required for valency are hydrogen.

"Ring" means a collection of member atoms that are cyclic. Rings may be carbocyclic, aromatic, or heterocyclic or heteroaromatic, and may be substituted or unsubstituted, and may be saturated or unsaturated. Ring junctions with the main chain may be fused or spirocyclic. Rings may be monocyclic or bicyclic. Rings contain at least three (3) member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S-alkyl.

"Sulfonyl" refers to the —S(O)$_2$R' group wherein R' is alkoxy, alkyl, aryl, carbocyclic, heterocarbocyclic; heteroaryl, C$_1$-C$_4$ alkyl aryl or C$_1$-C$_4$ alkyl heteroaryl.

"Sulfonylamino" refers to the —S(O)$_2$NR'R' group wherein each R' is independently alkyl, aryl, heteroaryl, C$_1$-C$_4$ alkyl aryl or C$_1$-C$_4$ alkyl heteroaryl.

"Pharmaceutically acceptable carrier" means a carrier that is useful for the preparation of a pharmaceutical composition that is: generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

"Excipient" as used herein includes physiologically compatible additives useful in preparation of a pharmaceutical composition. Examples of pharmaceutically acceptable carriers and excipients can for example be found in Remington Pharmaceutical Science, 16$^{th}$ Ed.

As used herein, "pharmaceutically acceptable salts" refers to an ionizable therapeutic agent that has been combined with a counter-ion to form a neutral complex. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the singular form of "a", "an" and "the" include plural references unless the context clearly dictates otherwise.

As used herein, the term "comprising" is intended to mean that the compositions and methods include the recited elements, but do not exclude others.

"About" and "approximately" are interchangeable, and mean plus or minus a percent (e.g., ±5%) of the number, parameter, or characteristic so qualified, which would be understood as appropriate by a skilled artisan to the scientific context in which the term is utilized. Furthermore, since all numbers, values, and expressions referring to quantities used herein, are subject to the various uncertainties of measurement encountered in the art, and then unless otherwise indicated, all presented values may be understood as modified by the term "about."

Where a numerical range is disclosed herein, then such a range is continuous, inclusive of both the minimum and maximum values of the range, as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include any and all subranges between the minimum value of 1 and the maximum value of 10.

As used herein, "therapeutic agent" refers to a compound or substance in a pharmaceutical composition that is biologically active and produces the effects of the pharmaceutical composition.

As used herein, the term "pharmaceutical composition" refers to a composition that comprises a therapeutic agent (i.e. a compound provided herein), excipient, a carrier, etc. Generally, pharmaceutical compositions are administered to a patient rather than the therapeutic agent alone.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a therapeutic agent or a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset.

The term "zwitterion" as used herein refers to a molecule or ion having separate positively and negatively charged groups.

The term "solvate" as used herein refers to a complex of a solute molecule and at least one solvent molecule.

The terms "polymorph" or "polymorphism" as used herein refer to the ability of a solid material to exist in more than one form or crystal. A crystal form may be referred to herein as being characterized by graphical data. Such data include, for example, powder X-ray diffractograms and solid-state NMR spectra. As is well-known in the art, the graphical data potentially provides additional technical information to further define the respective solid state form (a so-called "fingerprint") which can not necessarily be described by reference to numerical values or peak positions alone.

The terms "effective amount" or "therapeutically effective amount" refer to an amount, i.e. a dosage, of therapeutic agent administered to a subject (e.g., a mammalian subject, i.e. a human subject), either as a single dose or as part of a series of doses, which is effective to produce a desired therapeutic effect (e.g., effective for influencing, reducing or inhibiting the activity of or preventing activation of a kinase, or effective at bringing about a desired in vivo effect in an animal, preferably, a human, such as reduction in intraocular pressure).

"Administering" as used herein refers to administration of the compounds as needed to achieve the desired effect.

"Eye disease" as used herein includes, but is not limited to, glaucoma, allergy, cancers of the eye, neurodegenerative diseases of the eye such as DME and AMD, and dry eye.

The term "disease or condition associated with kinase activity" is used to mean a disease or condition treatable, in whole or in part, by inhibition of one or more kinases.

The term "controlling the disease or condition" is used to mean changing the activity of one or more kinases to affect the disease or condition.

The term "contacting a cell" is used to mean contacting a cell in vitro or in vivo (i.e. in a subject, such as a mammal, including humans, cats and dogs).

The term "non-aqueous solvent" is used to mean a solvent or mixture of solvents that contain less than 5% water by weight. Non-aqueous solvents include mixtures where the main solvent is a partially fluorinated hydrocarbon. Non-aqueous solvents may have preservatives or be preservative free.

The term "partially fluorinated hydrocarbon" refers to a hydrocarbon wherein some, but not all, of the hydrogen atoms of the hydrocarbon have been replaced by fluorine atoms. Non-limiting examples include perfluorohexyloctane, and perfluoropentylnonane. These are also known as semi-fluorinated alkanes, or SFA's in the art.

The term "myopia" refers to a patient's condition in which the patient has at least one eye with an SE value greater than −0.5 D, for example, −1.0 D, −2.0 D. Depending on context, "myopia" also refers to the condition of the eye, the SE value of which is higher than −0.5 D.

The term "pre-myopia" refers to a patient's condition in which the patient has at least one eye with an SE value within the range of −0.49 D to 1.00 D. Depending on context, myopic can also refer to the condition of the eye, the SE value of which is within the range of −0.49 D to 1.00 D.

The term "low myopia" refers to a patient's condition in which the patient has at least one eye with an SE value within the range of −0,501) to −1.501). Depending on context, "low7 myopia" can also refer to the condition of the eye, the SE value of which is within the range of 0.50 D to −1.50 D The term "high myopia" refers to a person having at least one eye with an SE value that is greater than −5.0 D. Depending on context, "high myopia" can also refer to the condition of the eye, the SE value of winch is greater than −5.0 D.

The term "drop" refers to tire a unit of measure of volume, which is equal to the amount dispensed as one drop from a dropper or drip chamber to the eye. Typically, a drop that is water-based contains 20-100 microliter liquid. In some cases, a drop contains between 30 microliters to 70 microliters, e.g., about 50 microliter liquid. Some drops, especially of partially fluorinated hydrocarbons, may be smaller than 30 microliters.

Compounds

In another aspect, provided herein are compounds, wherein the compound is: a compound of Formula (I),

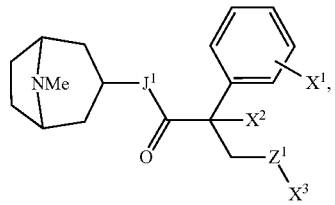

(I)

or an analog, derivative, solvate, zwitterion, or polymorph thereof, or a pharmaceutically acceptable salt thereof, wherein $X^1$ is hydrogen, hydroxyl, halogen, $C_1$ alkyl, amino, nitro, cyano, $C_{1-4}$ carbonyl, $C_{1-4}$ carbonylamino, $C_{1-4}$ alkoxy, $C_{1-4}$ sulfonyl, $C_{1-4}$ sulfonylamino, $C_{1-4}$ thioalkyl, or $C_{1-4}$ carboxyl;

$X^2$ is H or lower alkyl;

$X^3$ is H or lower alkyl;

$J^1$ is —$CH_2$—, —$N(R^1)$—, or —O—, wherein $R^1$ is H or lower alkyl;

$Z^1$ is —$CH_2$—, —$N(R^2)$—, or —O—, wherein $R^2$ is H or lower alkyl; and when the 8-methyl-8-azabicyclo[3.2.1]octan-3-yl moiety is in an endo conformation and $J^1$ is —O—, $X^2$ is lower alkyl or $X^3$ is lower alkyl.

In some embodiments, the 8-methyl-8-azabicyclo[3.2.1]octan-3-yl moiety is in an endo conformation.

In some embodiments, the 8-methyl-8-azabicyclo[3.2.1]octan-3-yl moiety is in an exo conformation.

In some embodiments, $J^1$ is —$CH_2$— or —$N(R^1)$—.

In some embodiments, when $J^1$ is —O—, $X^2$ is lower alkyl or $X^3$ is lower alkyl.

In some embodiments, $Z^1$ is $CH_2$ or $N(R^2)$.

In some embodiments, $X^2$ is lower alkyl or $X^3$ is lower alkyl.

In some embodiments, $X^1$ is hydroxyl, halogen, $C_{1-4}$ alkyl, amino, nitro, cyano, $C_{1-4}$ carbonyl, $C_{1-4}$ carbonylamino, $C_{1-4}$ alkoxy, $C_{1-4}$ sulfonyl, $C_{1-4}$ sulfonylamino, $C_{1-4}$ thioalkyl, or $C_{1-4}$ carboxyl.

In some embodiments, $X^1$ is hydroxyl, $C_{1-4}$ alkyl, amino, nitro, cyano, $C_{1-4}$ carbonyl, $C_{1-4}$ carbonylamino, $C_{1-4}$ alkoxy, $C_{1-4}$ sulfonyl, $C_{1-4}$ sulfonylamino, $C_{1-4}$ thioalkyl, or $C_{1-4}$ carboxyl.

In some embodiments, $X^1$ is hydroxyl, $C_{1-4}$ alkyl, amino, nitro, cyano, $C_{1-4}$ carbonyl, $C_{1-4}$ carbonylamino, $C_{1-4}$ sulfonyl, $C_{1-4}$ sulfonylamino, $C_{1-4}$ thioalkyl, or $C_{1-4}$ carboxyl.

In some embodiments: $Z^1$ is —$CH_2$— or —$N(R^2)$—; and $X^1$ is hydrogen, hydroxyl, $C_{1-4}$ alkyl, amino, nitro, cyano, $C_{1-4}$ carbonyl, $C_{1-4}$ carbonylamino, $C_{1-4}$ alkoxy, $C_{1-4}$ sulfonyl, $C_{1-4}$ sulfonylamino, $C_{1-4}$ thioalkyl, or $C_{1-4}$ carboxyl.

In some embodiments, the compound is:

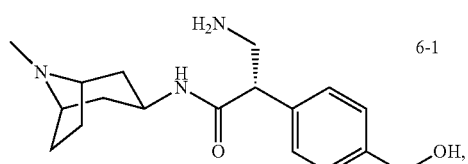

6-1

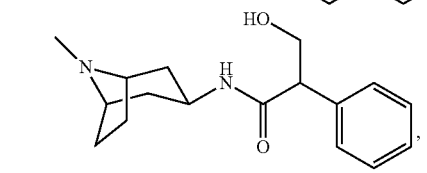

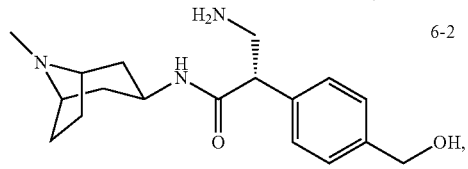

6-2

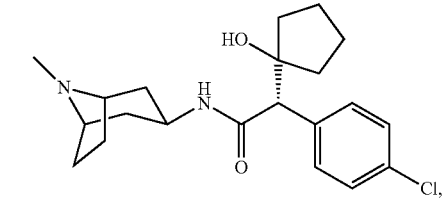

-continued
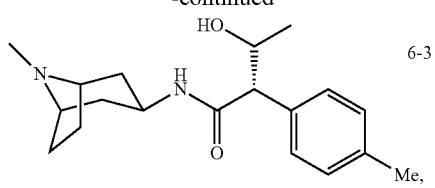
6-3
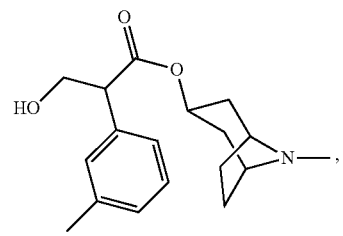
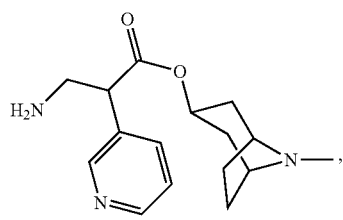
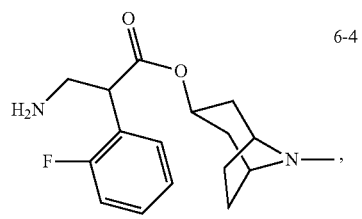
6-4
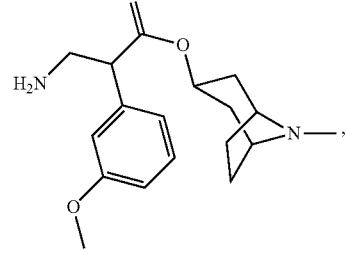
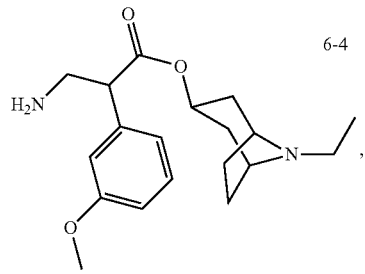
6-4
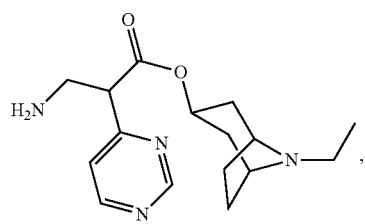
-continued
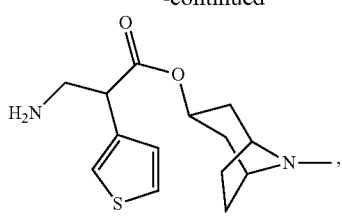
6-5
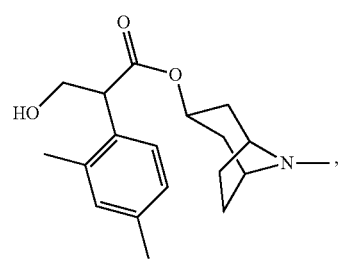
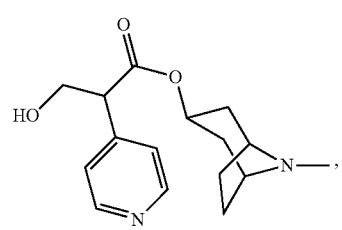
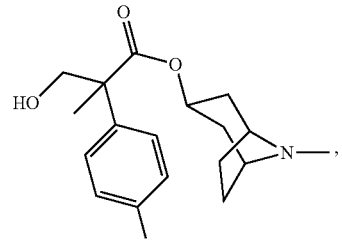
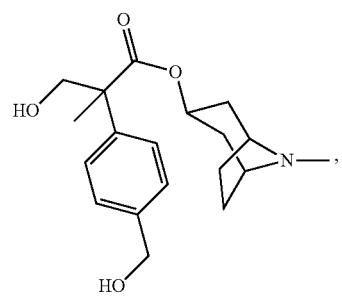
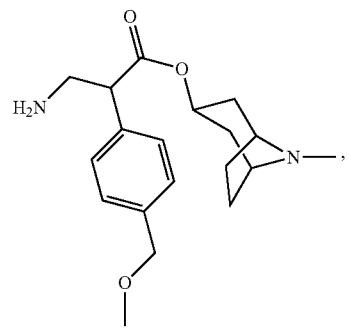
6-6

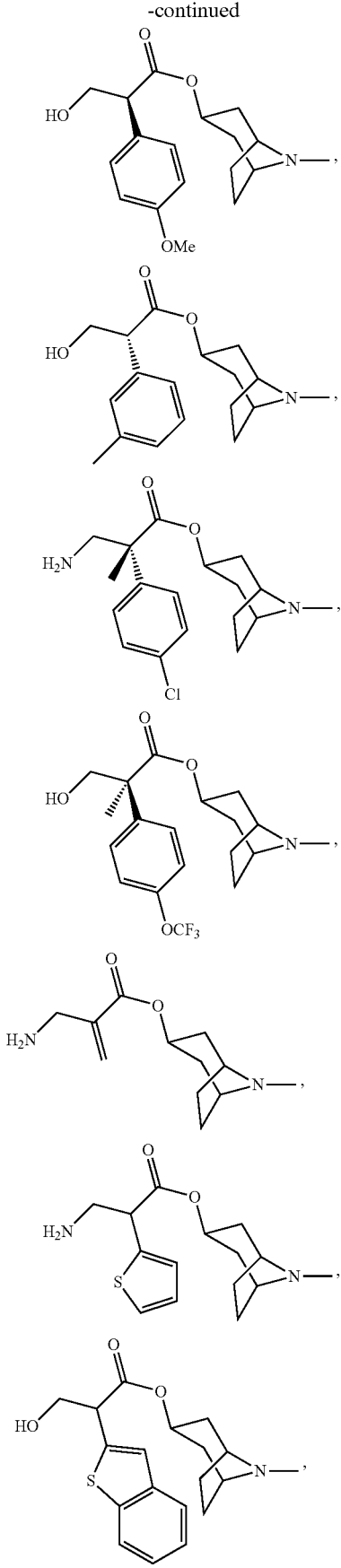
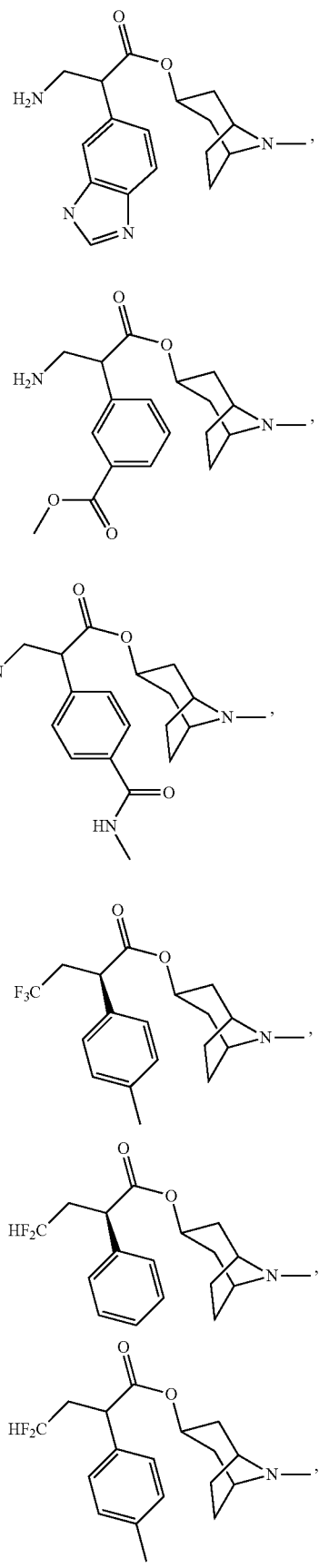

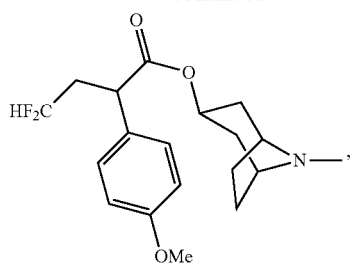
7-3
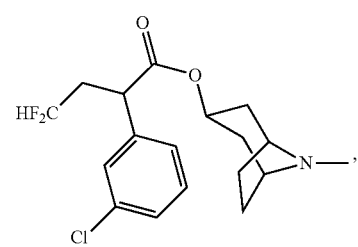
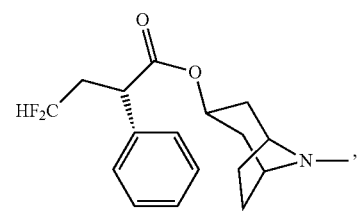
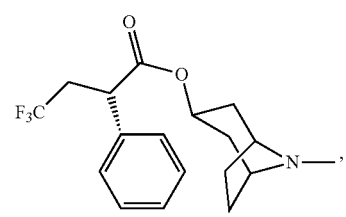
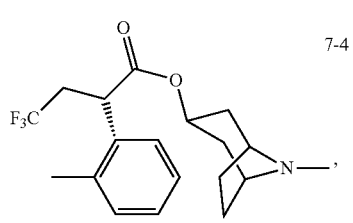
7-4
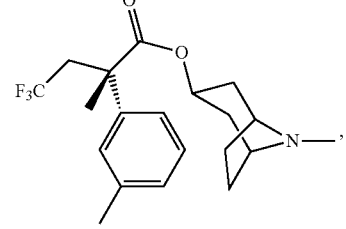
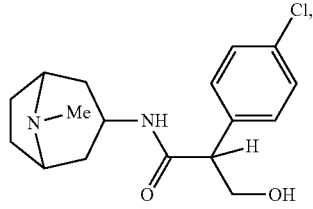
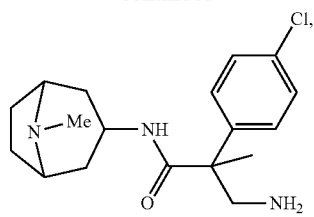
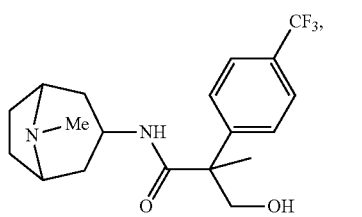
7-5
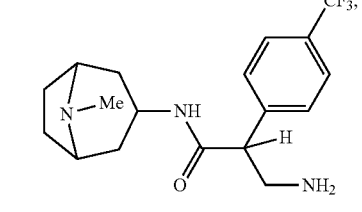
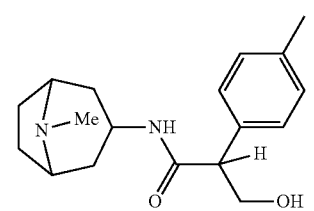
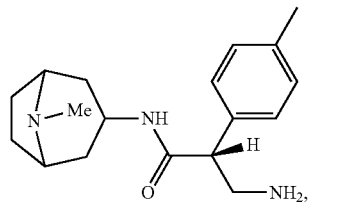
7-6
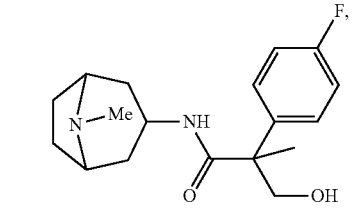
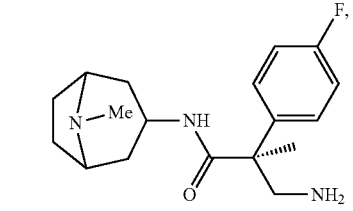
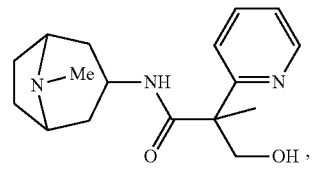

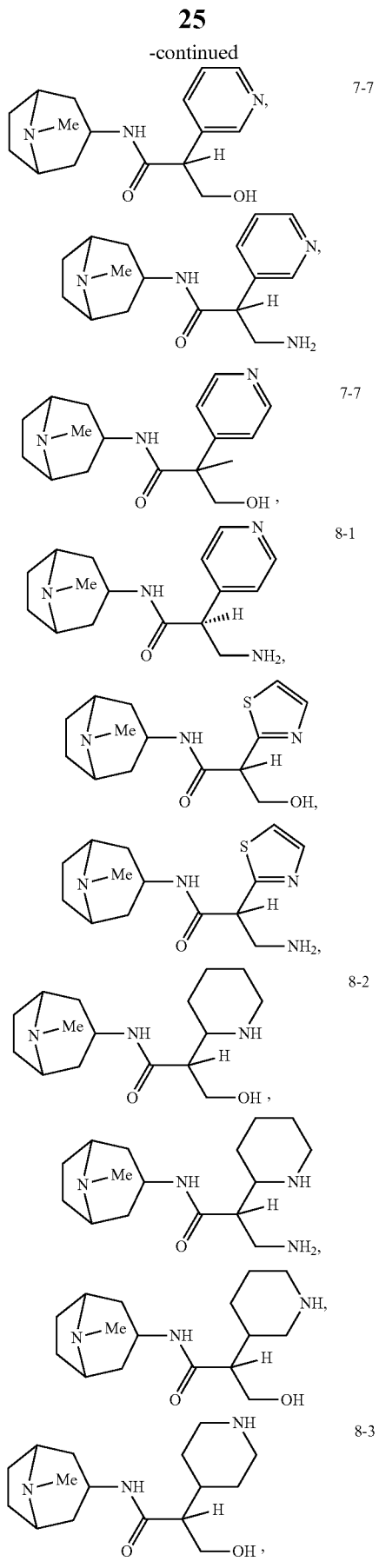

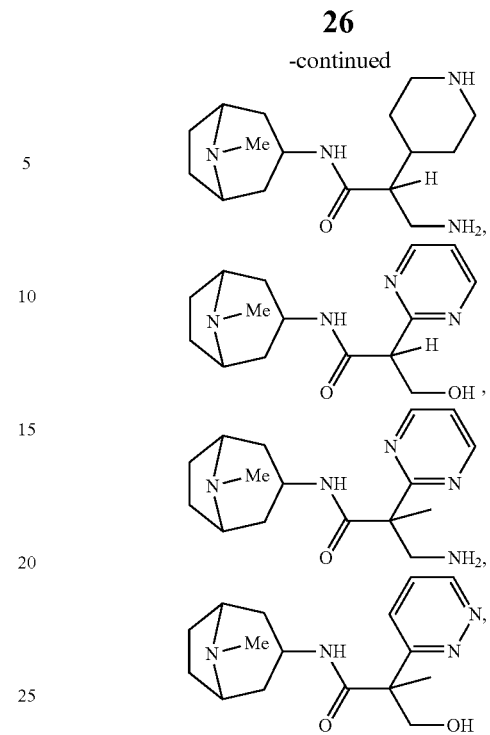

or an analog, derivative, solvate, zwitterion, or polymorph thereof, or a pharmaceutically acceptable salt thereof.

In another aspect, provided herein are compounds, wherein the compound is: a compound of Formula (II),

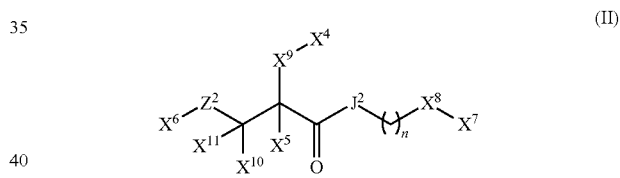

(II)

or an analog, derivative, solvate, zwitterion, or polymorph thereof, or a pharmaceutically acceptable salt thereof, wherein $X^4$ is hydrogen, hydroxyl, halogen, $C_{1-4}$ alkyl, $C_{1-4}$ haloalkyl, amino, nitro, cyano, $C_{1-4}$ carbonyl, $C_{1-4}$ carbonylamino, $C_{1-4}$ alkoxy, $C_{1-4}$ sulfonyl, $C_{1-4}$ sulfonylamino, $C_{1-4}$ thioalkyl, or $C_{1-4}$ carboxyl;

$X^5$ is H or lower alkyl;

$X^6$ is H or lower alkyl;

$X^7$ is hydrogen, hydroxyl, halogen, $C_{1-4}$ alkyl, amino, nitro, cyano, $C_{1-4}$ carbonyl, $C_{1-4}$ carbonylamino, $C_{1-4}$ alkoxy, $C_{1-4}$ sulfonyl, $C_{1-4}$ sulfonylamino, $C_{1-4}$ thioalkyl, or $C_{1-4}$ carboxyl;

$X^8$ is phenyl, pyridinyl, pyrimidinyl, or thienopyridinyl;

$X^9$ is phenyl, pyridinyl, pyrimidinyl, furanyl, or thiophenyl;

$X^{10}$ is hydrogen, halogen, $C_{1-4}$ alkyl, $C_{3-7}$ cycloalkyl, $C_{1-4}$ alkoxy, $C_{1-4}$ thioalkyl, or $C_{1-4}$ alkyl-phenyl;

$X^{11}$ is hydrogen, halogen, $C_{1-4}$ alkyl, $C_{3-7}$ cycloalkyl, $C_{1-4}$ alkoxy, $C_{1-4}$ thioalkyl, or $C_{1-4}$ alkyl-phenyl;

or $X^{10}$ and $X^{11}$, together with the atom to which they are attached, form $C_{3-7}$ cycloalkyl or $C_{3-7}$ cycloalkyl-$(X^{12})_p$, wherein each $X^{12}$ is, independently, halogen, hydroxyl, $C_{1-4}$ alkyl, $C_{1-4}$ alkoxy, $C_{1-4}$ haloalkyl, or phenyl, and p is 0, 1, 2, or 3;

$J^2$ is —CH$_2$—, —N(R$^3$)—, or —O—, wherein R$^3$ is H or lower alkyl;

$Z^2$ is —CH$_2$, —N(R$^4$)—, or —O—, wherein R$^4$ is H or lower alkyl; and n is 0 or 1.

In some embodiments, Formula (II) is of:

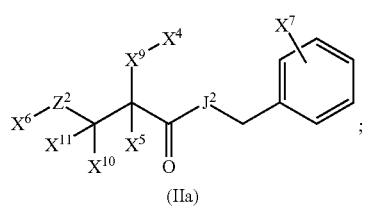

Formula (IIa)

(IIa)

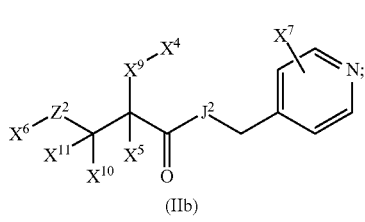

Formula (IIb)

(IIb)

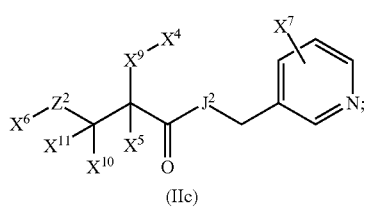

Formula (IIc)

(IIc)

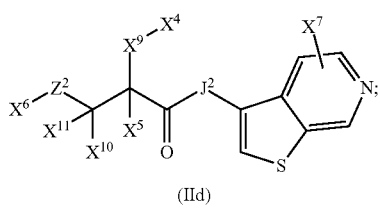

Formula (IId)

(IId)

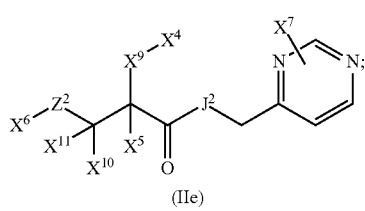

Formula (IIe)

(IIe)

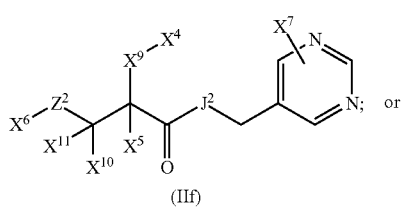

Formula (IIf)

(IIf)

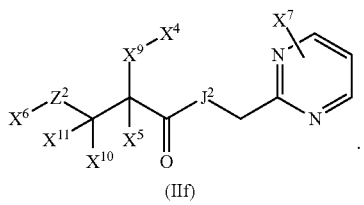

Formula (IIg)

(IIg)

In some embodiments, Formula (II) is of Formula (IIb-1),

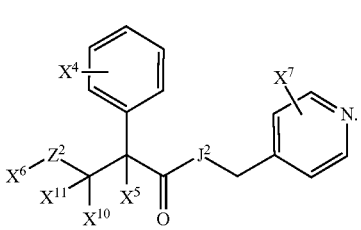

(IIb-1)

In some embodiments: $X^8$ is phenyl or pyridinyl; and $X^9$ is phenyl, pyridinyl, furanyl, or thiophenyl.

In some embodiments, $X^4$ is hydrogen, halogen, $C_{1-4}$ alkyl, $C_{1-4}$ haloalkyl, or $C_{1-4}$ alkoxy.

In some embodiments, $X^7$ is hydrogen, halogen, or $C_{1-4}$ alkyl.

In some embodiments, —Z$^2$—X$^6$ is —OH or —NH$_2$.

In some embodiments: $X^{10}$ is hydrogen, $C_{1-4}$ alkyl, $C_{3-7}$ cycloalkyl, or $C_{1-4}$ alkyl-phenyl, and $X^{11}$ is hydrogen or $C_{1-4}$ alkyl; or $X^{10}$ and $X^{11}$, together with the atom to which they are attached, form $C_{3-7}$ cycloalkyl or $C_{3-7}$ cycloalkyl-phenyl.

In some embodiments, the compound is:

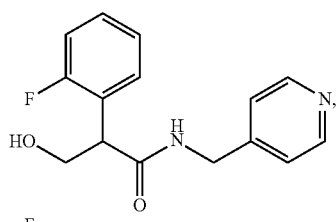

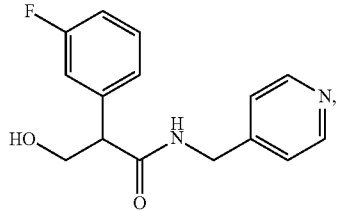

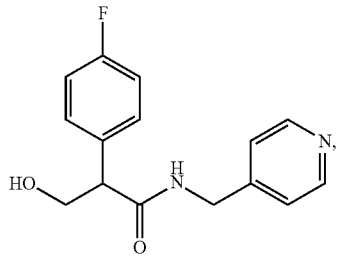

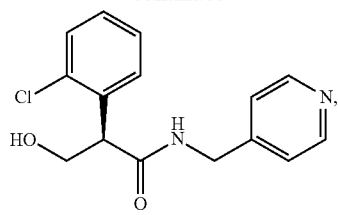
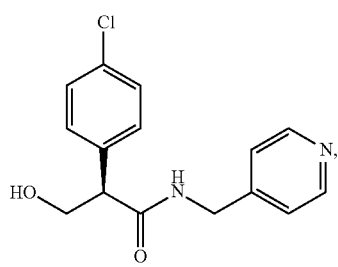
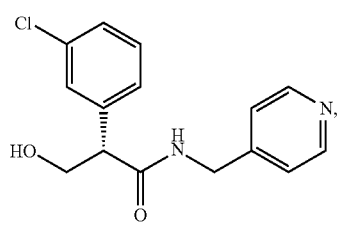
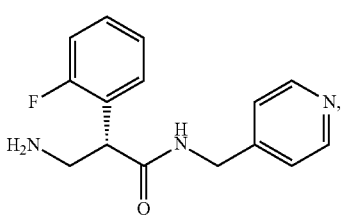
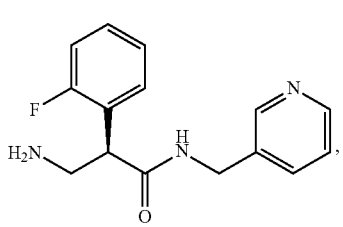
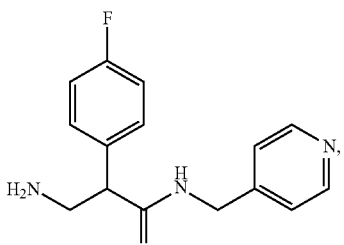
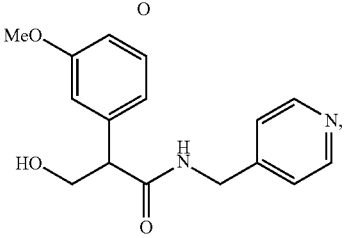
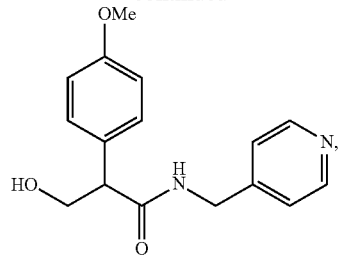
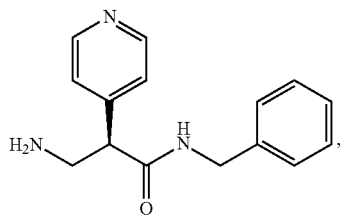
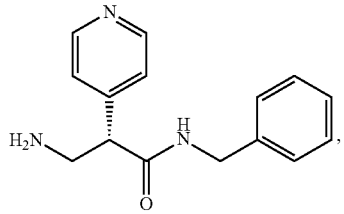
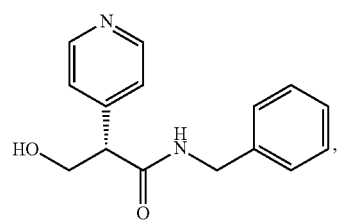
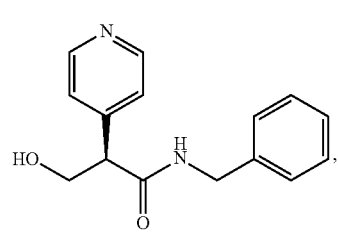
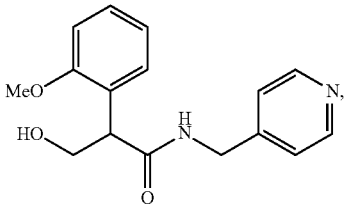
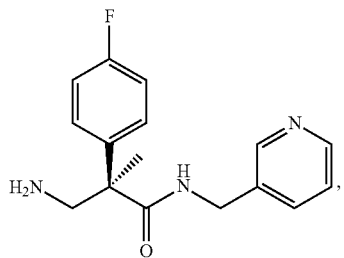

-continued

-continued
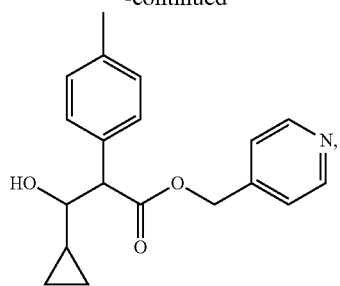
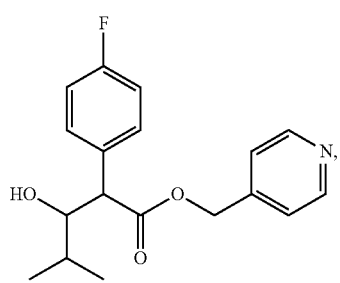
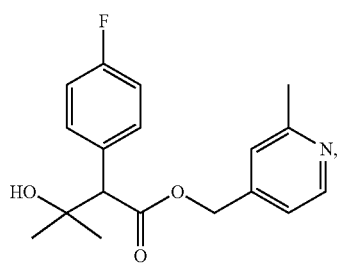
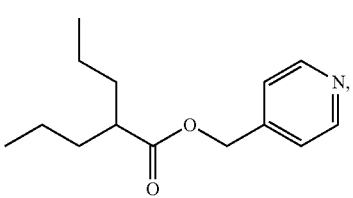
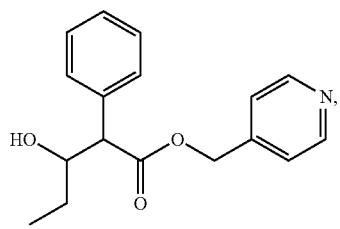
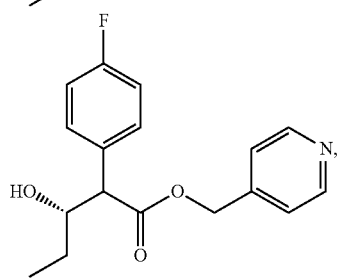
-continued
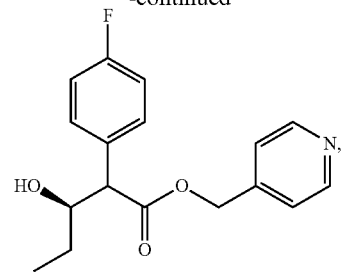
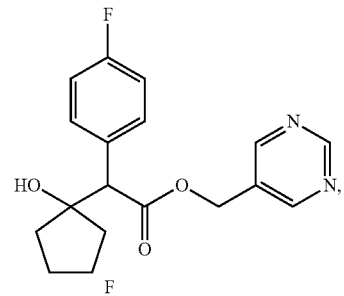
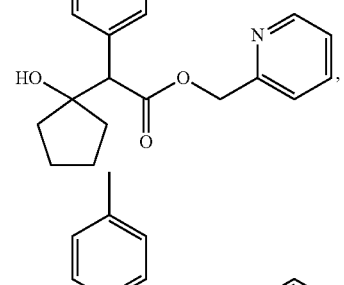
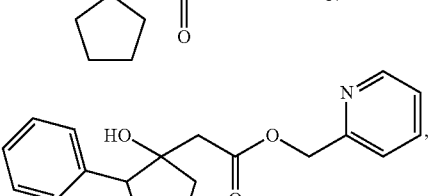
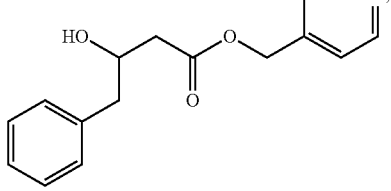
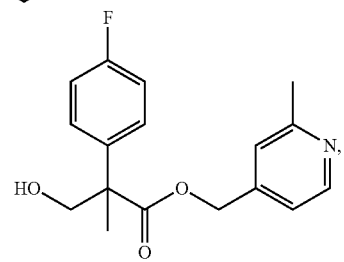

-continued

[Chemical structure: 4-(trifluoromethyl)phenyl compound with HO-CH2, methyl, ester linkage to (3-fluoropyridin-4-yl)methyl]

[Chemical structure: 4-chlorophenyl compound with H2N-CH2, ethyl, ester linkage to pyridin-4-ylmethyl]

[Chemical structure: 4-chlorophenyl compound with H2N-CH2, ester linkage to pyrimidin-5-ylmethyl]

or an analog, derivative, solvate, zwitterion, or polymorph thereof, or a pharmaceutically acceptable salt thereof.

Compositions

In another aspect, provided herein are compositions, comprising a compound provided herein.

In some embodiments, the compositions comprise a semi-fluorinated alkane.

In some embodiments, provided herein are compositions, comprising a semi-fluorinated alkane and:

a compound of Formula (I), (I)

[Chemical structure of Formula (I)]

or an analog, derivative, solvate, zwitterion, or polymorph thereof, or a pharmaceutically acceptable salt thereof, wherein $X^1$ is hydrogen, hydroxyl, halogen, $C_{1-4}$ alkyl, amino, nitro, cyano, $C_{1-4}$ carbonyl, $C_{1-4}$ carbonylamino, $C_{1-4}$ alkoxy, $C_{1-4}$ sulfonyl, $C_{1-4}$ sulfonylamino, $C_{1-4}$ thioalkyl, or $C_{1-4}$ carboxyl, $X^2$ is H or lower alkyl, $X^3$ is H or lower alkyl, $J^1$ is —$CH_2$—, —$N(R^1)$—, or —O—, wherein $R^1$ is H or lower alkyl, $Z^1$ is —$CH_2$—, —$N(R^2)$—, or —O—, wherein $R^2$ is H or lower alkyl, and when the 8-methyl-8-azabicyclo[3.2.1]octan-3-yl moiety is in an endo conformation and $J^1$ is —O—, $X^2$ is lower alkyl or $X^3$ is lower alkyl; or a compound of Formula (II), (II)

[Chemical structure of Formula (II)]

or an analog, derivative, solvate, zwitterion, or polymorph thereof, or a pharmaceutically acceptable salt thereof, wherein $X^4$ is hydrogen, hydroxyl, halogen, $C_{1-4}$ alkyl, $C_{1-4}$ haloalkyl, amino, nitro, cyano, $C_{1-4}$ carbonyl, $C_{1-4}$ carbonylamino, $C_{1-4}$ alkoxy, $C_{1-4}$ sulfonyl, $C_{1-4}$ sulfonylamino, $C_{1-4}$ thioalkyl, or $C_{1-4}$ carboxyl, $X^5$ is H or lower alkyl, $X^6$ is H or lower alkyl, $X^7$ is hydrogen, hydroxyl, halogen, $C_{1-4}$ alkyl, amino, nitro, cyano, $C_{1-4}$ carbonyl, $C_{1-4}$ carbonylamino, $C_{1-4}$ alkoxy, $C_{1-4}$ sulfonyl, $C_{1-4}$ sulfonylamino, $C_{1}$-4 thioalkyl, or $C_{1-4}$ carboxyl, $X^8$ is phenyl, pyridinyl, pyrimidinyl, or thienopyridinyl, $X^9$ is phenyl, pyridinyl, pyrimidinyl, furanyl, or thiophenyl, $X^{10}$ is hydrogen, halogen, $C_{1-4}$ alkyl, $C_{3-7}$ cycloalkyl, $C_{1-4}$ alkoxy, $C_{1-4}$ thioalkyl, or $C_{1-4}$ alkyl-phenyl, $X^{11}$ is hydrogen, halogen, $C_{1-4}$ alkyl, $C_{3-7}$ cycloalkyl, $C_{1-4}$ alkoxy, $C_{1-4}$ thioalkyl, or $C_{1-4}$ alkyl-phenyl, or $X^{10}$ and $X^{11}$, together with the atom to which they are attached, form $C_{3-7}$ cycloalkyl or $C_{3-7}$ cycloalkyl-$(X^{12})_p$, wherein each $X^{12}$ is, independently, halogen, hydroxyl, $C_{1-4}$ alkyl, $C_{1-4}$ alkoxy, $C_{1-4}$ haloalkyl, or phenyl, and p is 0, 1, 2, or 3, $J^2$ is —$CH_2$—, —$N(R^3)$—, or —O—, wherein $R^3$ is H or lower alkyl, $Z^2$ is —$CH_2$—, —$N(R^4)$—, or —O—, wherein $R^4$ is H or lower alkyl, and n is 0 or 1.

In some embodiments, provided herein are compositions, comprising a semi-fluorinated alkane, and a compound, wherein the compound is:

[Chemical structure: tropane-NH-C(=O)-CH(4-hydroxymethylphenyl)-CH2-NH2]

[Chemical structure: tropane-O-C(=O)-CH(3-chlorophenyl)-CH2-OH]

[Chemical structure: tropane-O-C(=O)-C(Me)(phenyl)-CH2-OH]

37
-continued
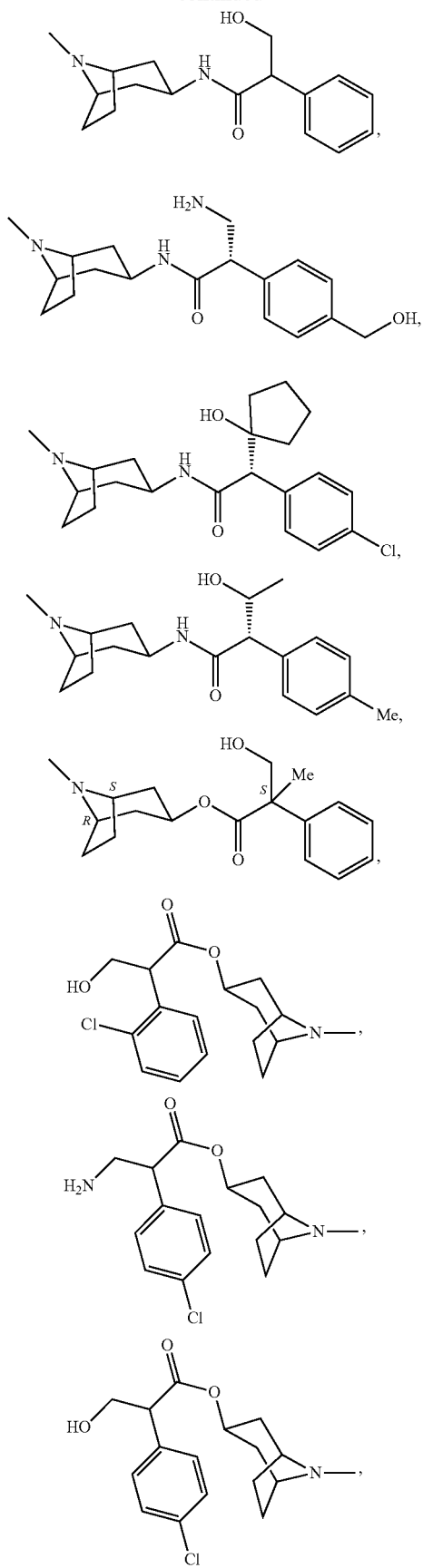
38
-continued
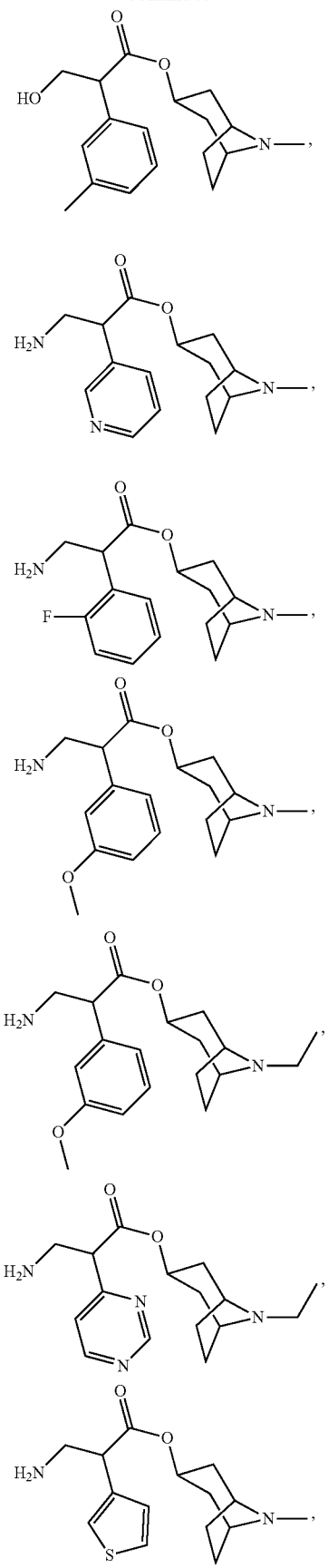

-continued
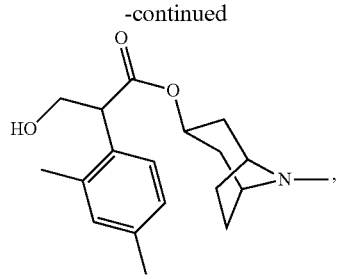
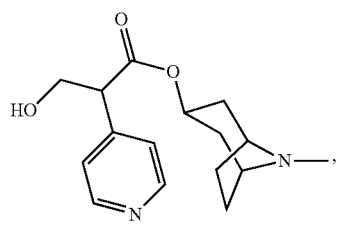
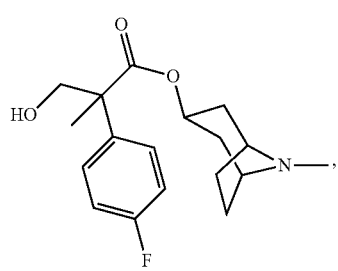
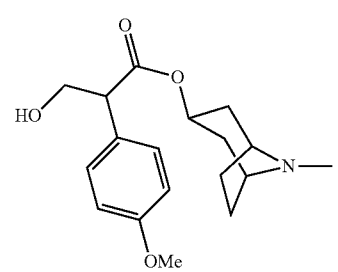
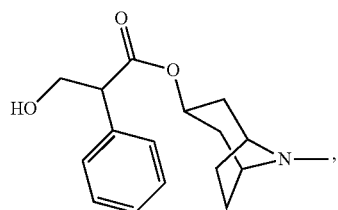
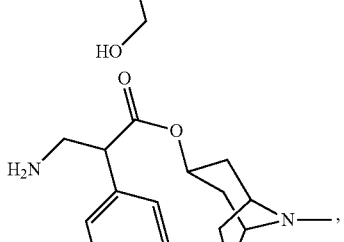
-continued
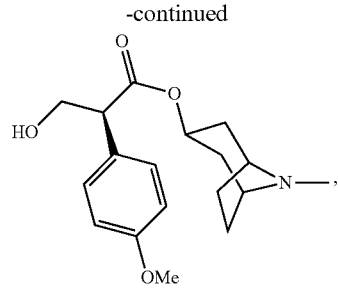
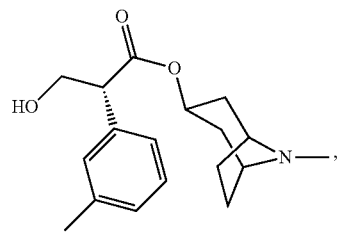
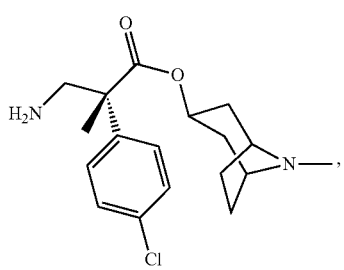
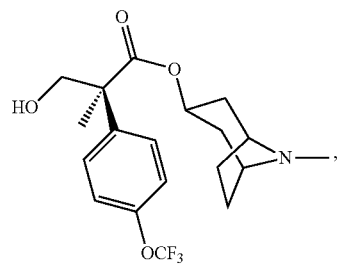
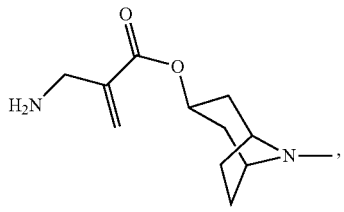
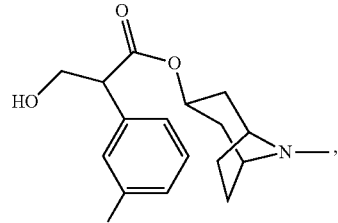
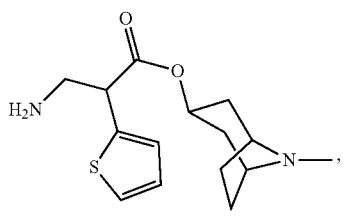

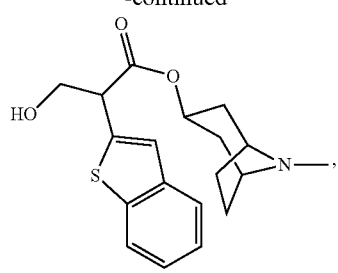
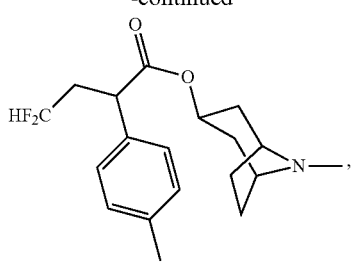
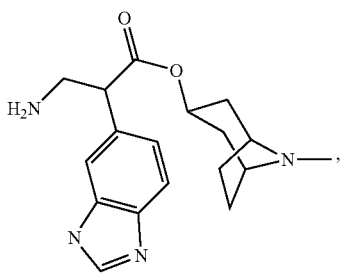
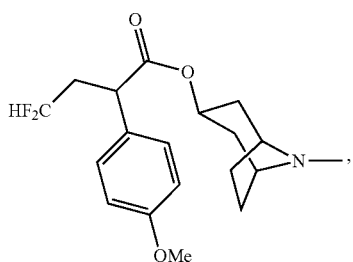
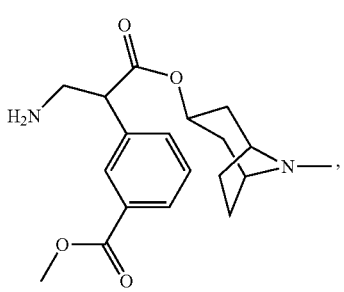
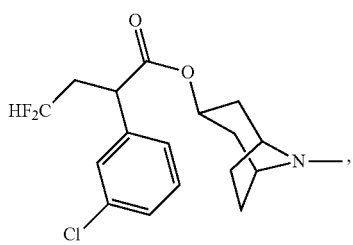
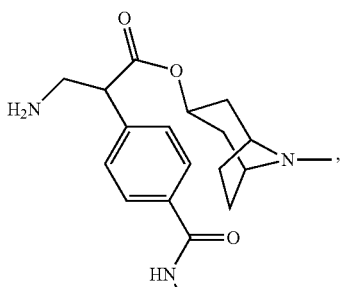
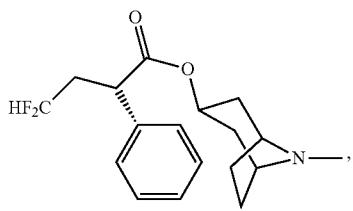
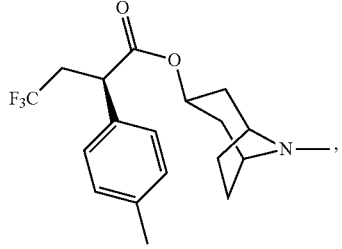
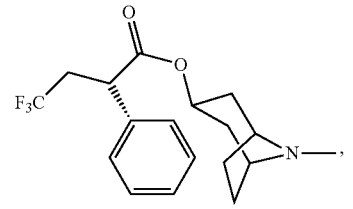
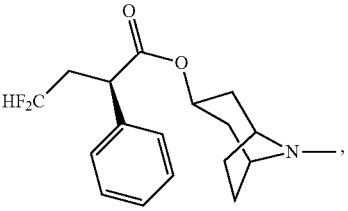
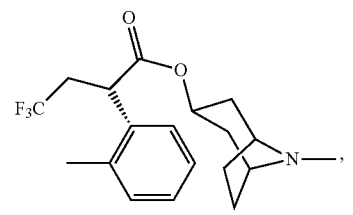
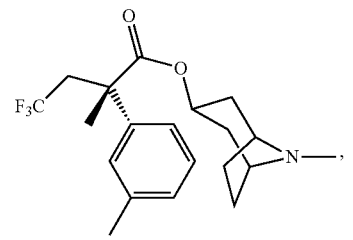

-continued

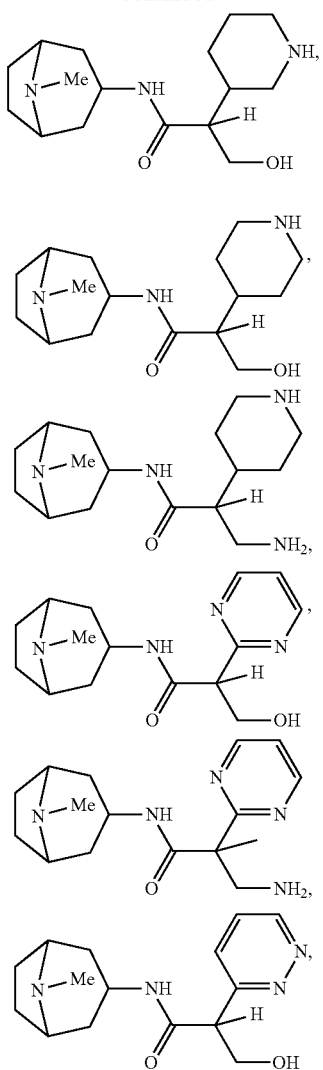
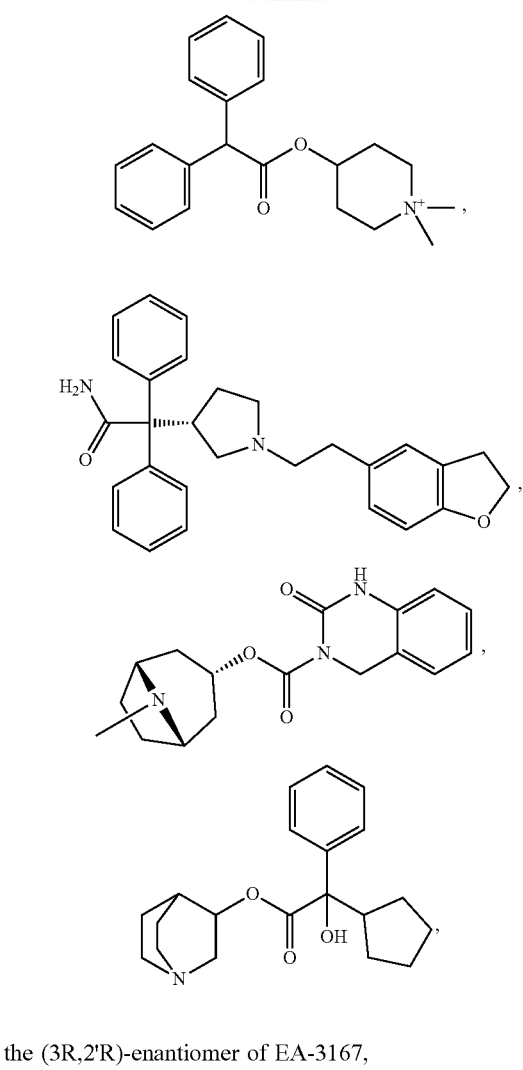
the (3R,2'R)-enantiomer of EA-3167,
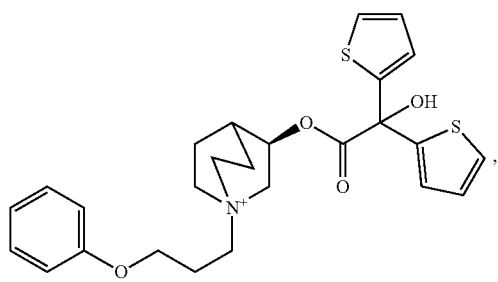
benzeneacetic acid,
α-(hydroxymethyl)-(3-endo)-8-methyl-8-azabicyclo[3.2.1]oct-3-yl ester, (αR)-benzeneacetic acid,
α-(hydroxymethyl)-(3-endo)-8-methyl-8-azabicyclo[3.2.1]oct-3-yl ester, (αS)-Benzeneacetic acid,
α-(hydroxymethyl)-(3-endo)-8-methyl-8-azabicyclo[3.2.1]oct-3-yl ester, endo-benzeneacetic acid,
α-(hydroxymethyl)-8-(methyl-d3)-8-azabicyclo[3.2.1]oct-3-yl ester,
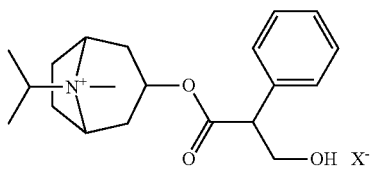
wherein X is Cl, Br or I,
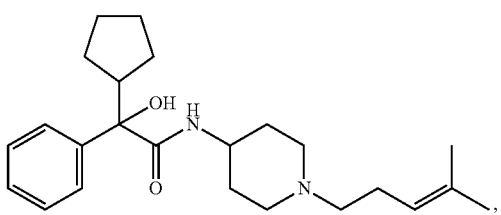

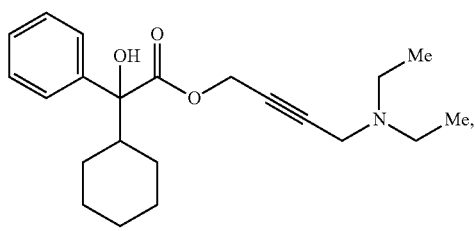
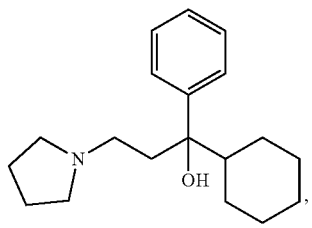
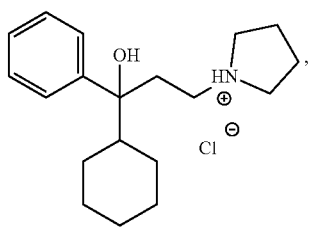
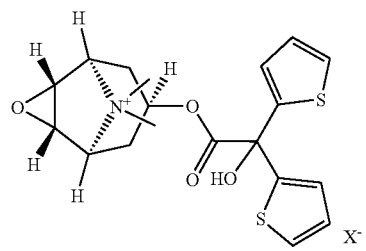
wherein X is Cl, Br or I,
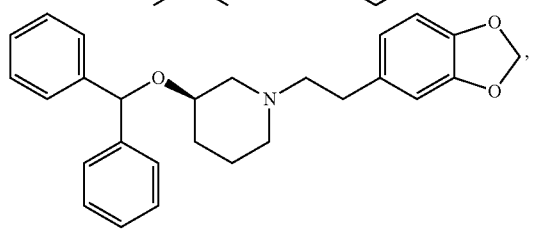
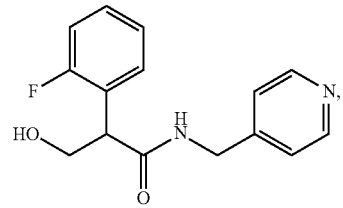
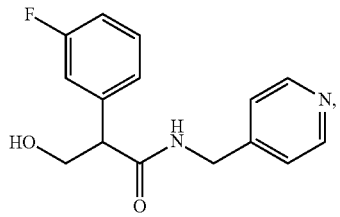
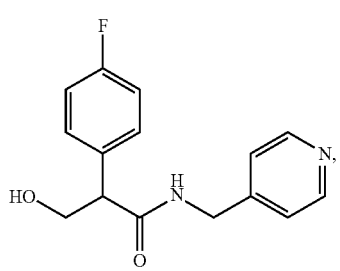
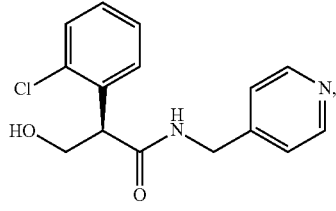
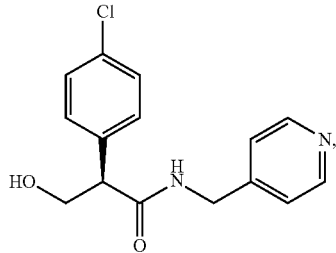
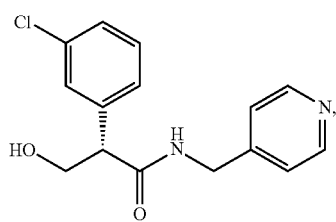
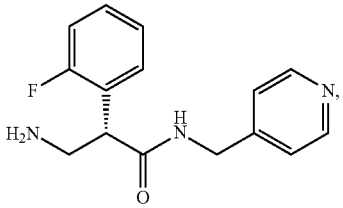
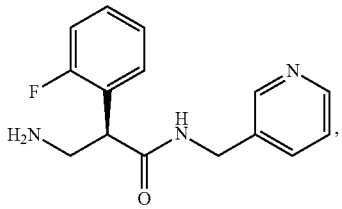

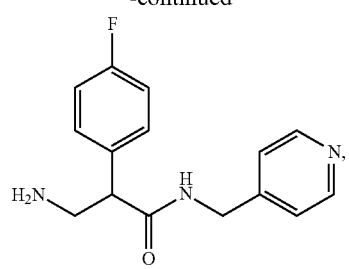
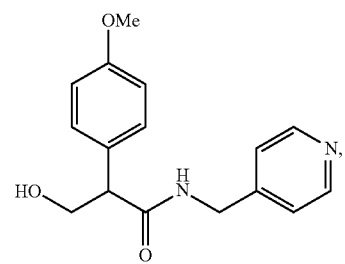
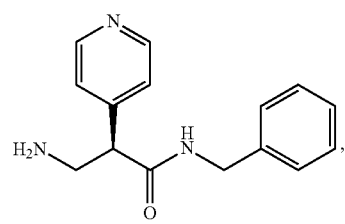
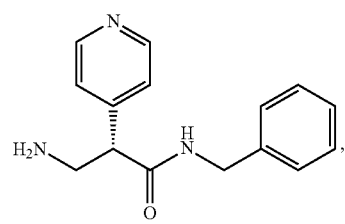
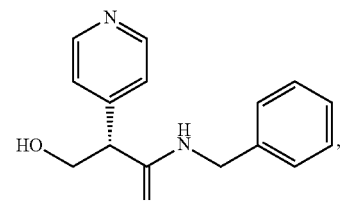
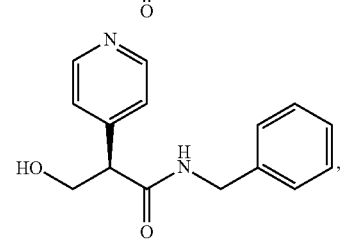
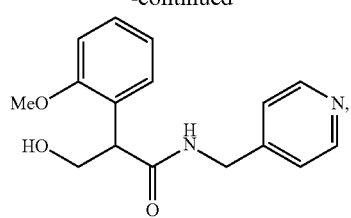
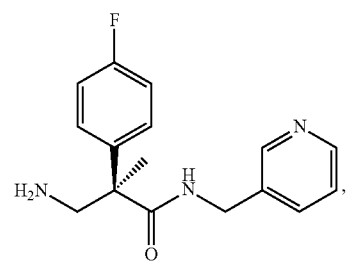
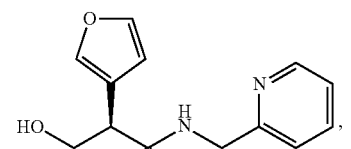
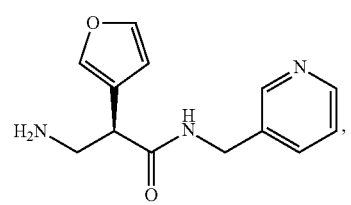
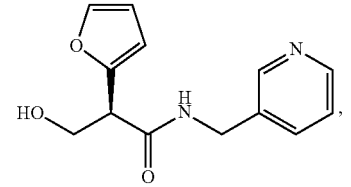
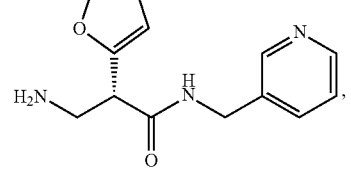
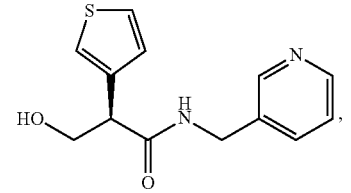
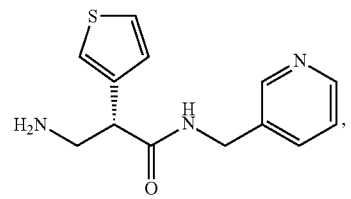

-continued
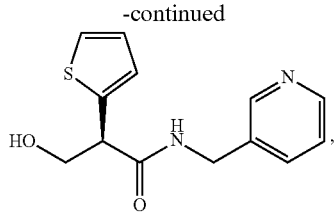
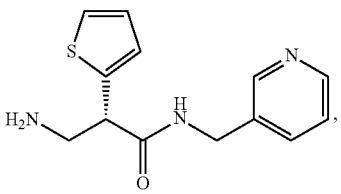
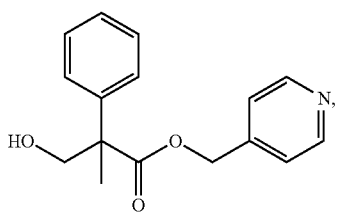
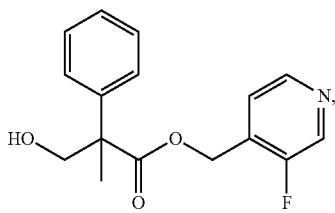
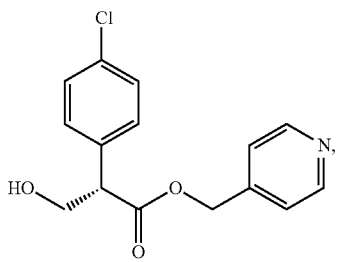
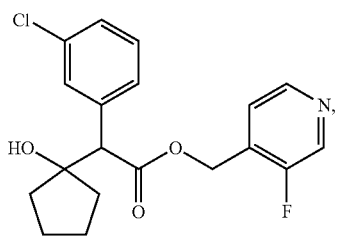
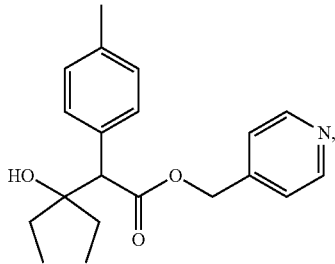
-continued
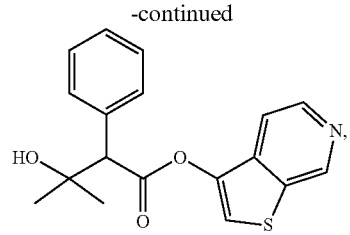
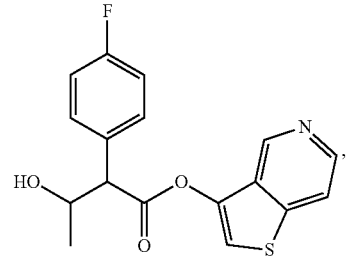
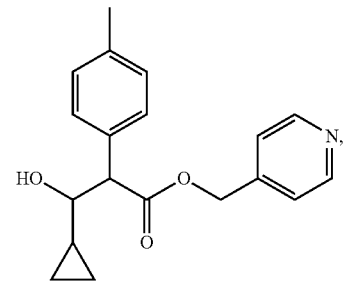
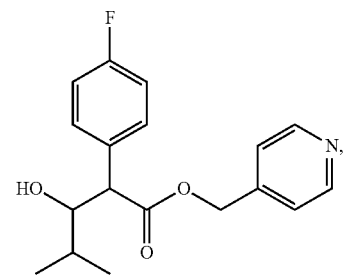
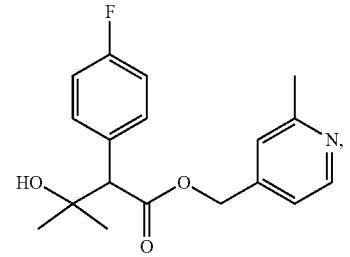
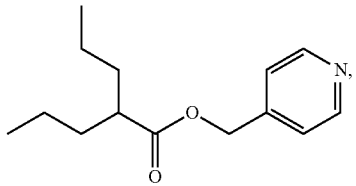
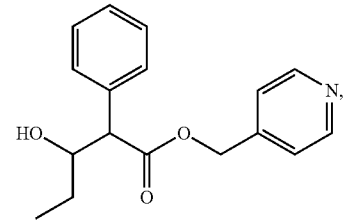

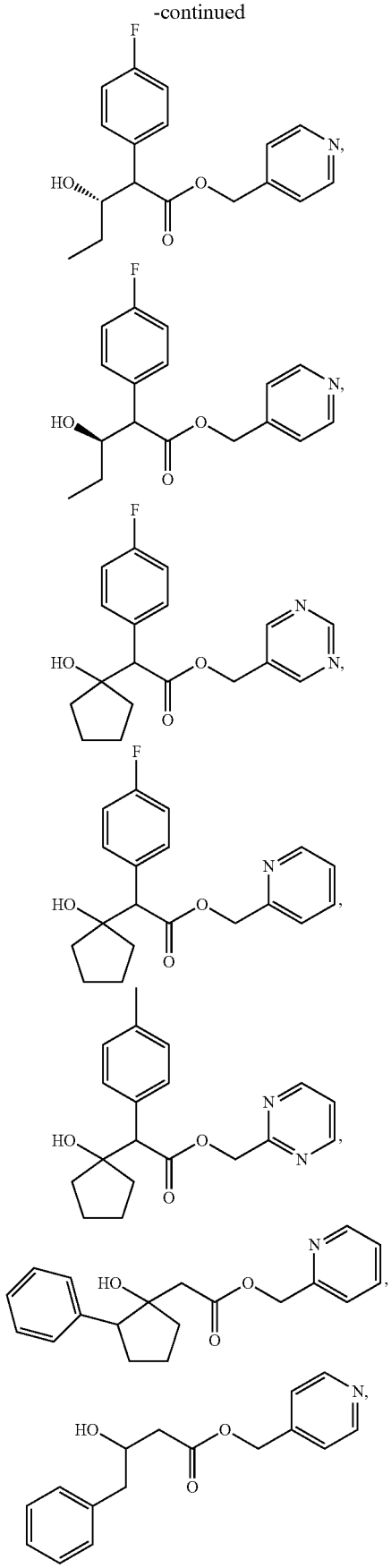

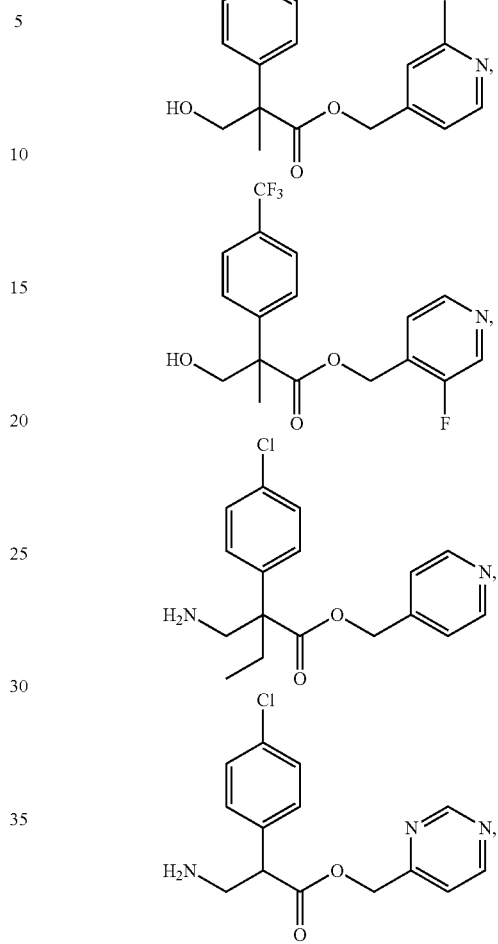

or an analog, derivative, solvate, zwitterion, or polymorph thereof, or a pharmaceutically acceptable salt thereof.

In some embodiments, the semi-fluorinated alkane is perflurohexyloctane or perflurohexylnonane.

In some embodiments, the composition is a non-aqueous composition.

In some embodiments, the compositions provided herein are pharmaceutical compositions, comprising a compound provided herein or a composition provided herein, and a pharmaceutically acceptable excipient.

Kits and Articles of Manufacture

Also provided herein are kits, comprising a compound provided herein, a composition provided herein, or a pharmaceutical composition provided herein, and instructions for use thereof.

Also provided herein are articles of manufacture, comprising a compound provided herein, a composition provided herein, or a pharmaceutical composition provided herein.

Methods

The compounds and compositions provided herein are useful in treating eye diseases or conditions. Thus, in one aspect, provided herein are methods of treating myopia in a subject in need thereof, comprising administering to the subject a therapeutically effective amount of a compound provided herein, a composition provided herein, or a pharmaceutical composition provided herein.

Also provided herein are methods of reducing the progression of myopia in a subject in need thereof, comprising administering to the subject a therapeutically effective amount of a compound provided herein, a composition provided herein, or a pharmaceutical composition provided herein.

Also provided herein are methods of delaying the onset of myopia in a subject in need thereof, comprising administering to the subject a therapeutically effective amount of a compound provided herein, a composition provided herein, or a pharmaceutical composition provided herein.

Also provided herein are methods of treating a sight threatening disease or disorder in a subject in need thereof, comprising administering to the subject a therapeutically effective amount of a compound provided herein, a composition provided herein, or a pharmaceutical composition provided herein.

In some embodiments, the sight threatening disease or disorder comprises peripheral lattice change, tear, detachment, myopic choroidal neo-vascularization, myopic macular schist, myopic macular hole, posterior staphyloma, myopic macular degeneration, early-onset cataracts, open angle glaucoma, peri-papillary atrophy, optic disc tilt, optic disc pits, or a combination thereof.

General Synthetic Scheme

The 8-methyl-8-azabicyclo[3.2.1]octan-3-yl and pyridin-4-ylmethanyl ester and amide compounds provided herein may be synthesized by the general schemes set forth below:

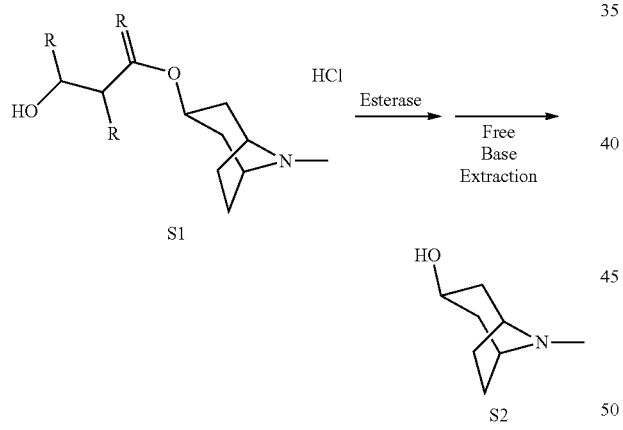

According to Scheme 1, a selected ester (S1) is reacted with an esterase enzyme such as pig liver esterase to form the desired intermediate (S2). The alcohol (S2) is extracted and purified as necessary, and then taken on to Scheme 2.

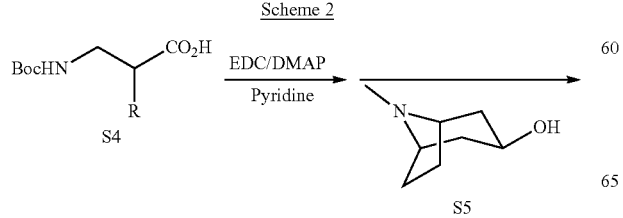

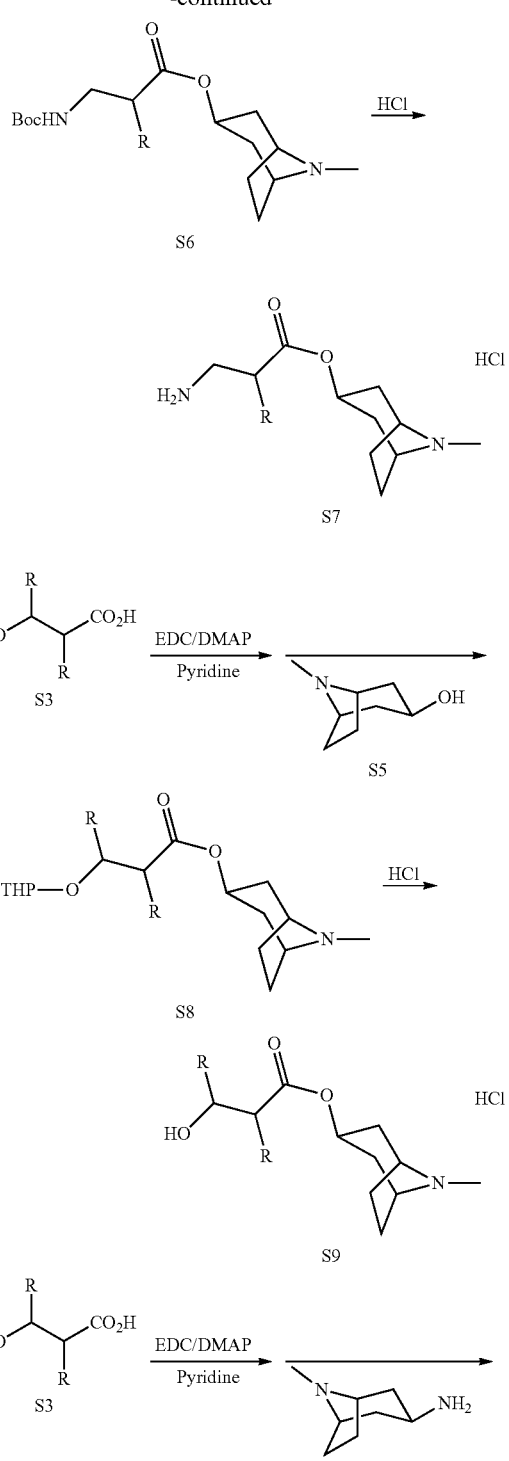

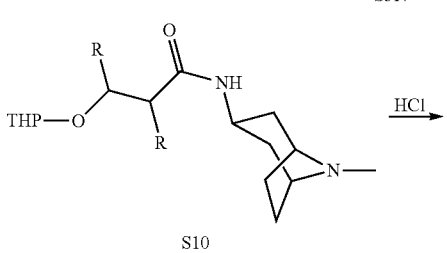

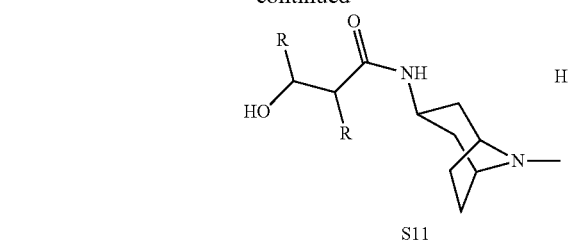

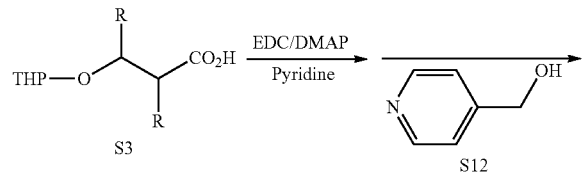

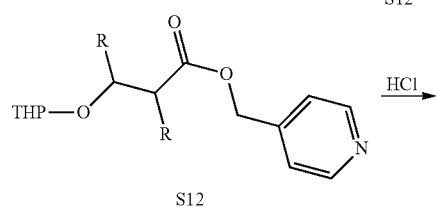

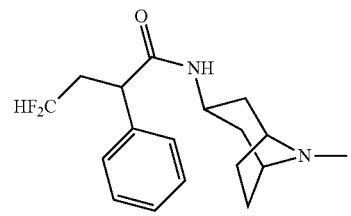

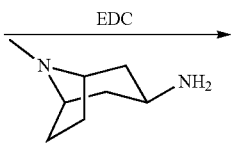

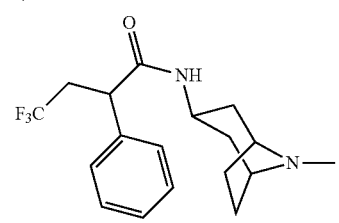

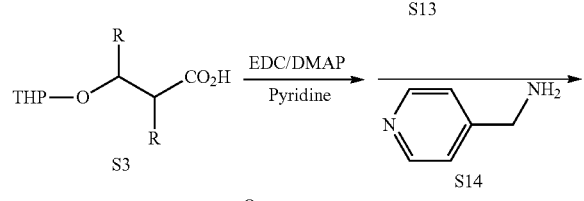

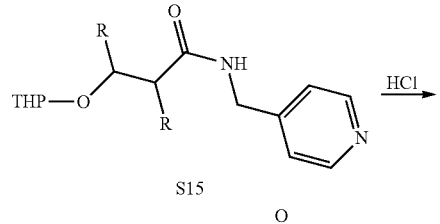

R = alkyl, aryl, heteroaryl, alkyl aryl, alkyl heteroaryl

According to Scheme 2, the selected acid (S4) is activated with an appropriate agent such as EDC then coupled to an 8-methyl-8-azabicyclo[3.2.1]octan-3-yl and pyridin-4-yl-methanyl alcohol (S5) or amine (S8) using standard coupling procedures to form the desired intermediates (S6, S9, S12 and S15). The protected amine of (S6), or the protected alcohol of (S8, S10, S12 and S15) is reacted with HCl in methylene chloride to generate the amide (S11) directly.

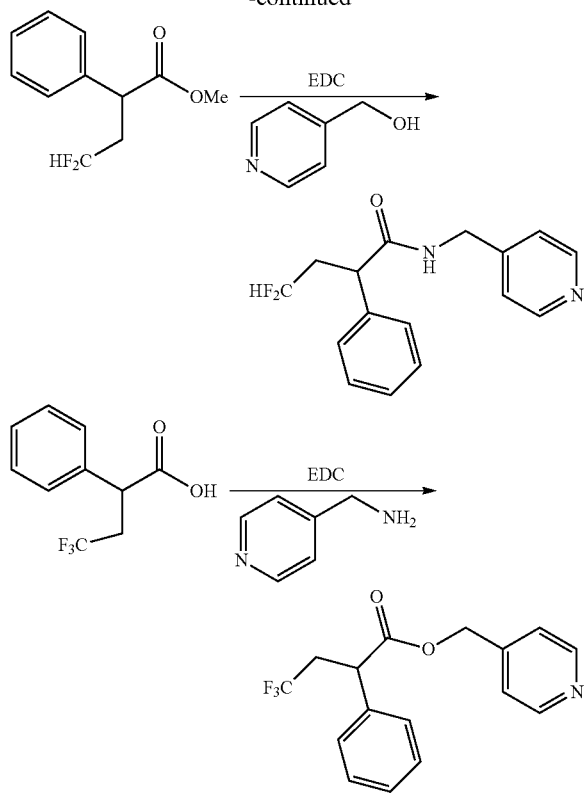

In some embodiments, the administration of an additional therapeutic agent with a compound provided herein will enable lower doses of the other therapeutic agents to be administered for a longer period of time.

Compositions including 8-methyl-8-azabicyclo[3.2.1]octan-3-yl and pyridin-4-ylmethanyl alkyl, ester and amide derivatives of Formulae I, II, or III may be obtained in the form of various salts or solvates. As the salts, physiologically acceptable salts or salts available as raw materials are used.

Compositions may include one or more of the isoforms of Formula I or II or III or IV when present. When racemates exists, each enantiomer or diastereomer may be separately used, or they may be combined in any proportion. Where tautomers exist all possible tautomers are specifically contemplated.

Pharmaceutical compositions for use in accordance as provided herein may be formulated in a conventional manner using one or more physiologically acceptable carriers or excipients. Thus, the compounds and their physiologically acceptable salts and solvates may be formulated for administration by, for example, solid dosing, eyedrop, in a topical oil-based formulation, injection, inhalation (either through the mouth or the nose), implants—including bioerodible implants placed in either the front or the back of the eye, or oral, buccal, parenteral or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

Compositions provided herein may comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, duration of treatment, the nature of concurrent therapy, the particular pharmaceutically-acceptable carrier utilized, and like factors within the knowledge and expertise of the attending physician.

The route by which the compounds provided herein (component A) will be administered and the form of the composition will dictate the type of carrier (component B) to be used. The composition may be in a variety of forms, suitable, for example, for systemic administration (e.g., oral, rectal, nasal, sublingual, buccal, implants, or parenteral) or topical administration (e.g., local application on the skin, ocular, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, q) biodegradable polymers, r) plasticizers, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of ingredient b) in the systemic or topical composition is typically about 5 to about 10%.

Ingredient c) is a binder. Suitable binders for solid dosage forms include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to 99%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as a partially fluorinated hydrocarbon, water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include AVICEL® RC-591 (from FMC Corporation of Philadelphia, Pa.) and sodium alginate. The amount of ingredient n) in the systemic or topical composition is typically about 1 to about 8%.

Ingredient o) is a surfactant such as lecithin, Polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic or topical composition is typically about 0.1% to about 5%.

Ingredient p) is a surfactant.

Ingredient q) is a biodegradable polymer. PLA or PLGA polymers, and well as PEA polymers, are specifically contemplated.

Ingredient r) is a plasticizer. These lower the TM of the polymer to allow for manufacturing at lower temperatures or under other conditions to make the manufacturing more facile. A non-limiting example Although the amounts of components A and B in the systemic compositions will vary depending on the type of systemic composition prepared, the specific derivative selected for component A and the ingredients of component B, in general, system compositions comprise 0.01% to 50% of component A and 50 to 99.99% of component B.

Compositions for parenteral administration typically comprise A) 0.1 to 10% of the compounds provided herein and B) 90 to 99.9% of a carrier comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50 to about 95% of component B), and more particularly, from about 50 to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including implants, time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics. Implants can be of the biodegradable or the non-biodegradable type. Implants may be prepared using any known biocompatible formulation.

The selection of ingredients in the carrier for oral compositions depends on secondary considerations including, but not limited to taste, cost, and shelf stability.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include implanted, sublingual, buccal and nasal dosage forms. Such compositions typically comprise one or more of soluble or biodegradable filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants. Implanted formulations typically include q) biodegradable polymers and optionally, r) plasticizers.

In one embodiment, the compounds provided herein are topically administered. Topical compositions that can be applied locally to the eye may be in any form known in the art, non-limiting examples of which include solids, gelable drops, sprays, ointments, or a sustained or non-sustained release unit placed in the conjunctival cul-du-sac of the eye, in the intracameral space, in the aqueous humor, in the vitreous humor, or another appropriate location.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the compounds described above, and component B, a carrier. The carrier of the topical composition preferably aids penetration of the compounds into the eye. Component B may further comprise one or more optional components.

The dosage range of the compound for systemic administration is from about 0.0001 to about 1000 µg/kg body weight, preferably from about 0.1 to about 100 µg/kg per body weight, most preferably form about 1 to about 50 µg/kg body weight per day. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds provided herein are useful in decreasing intraocular pressure. Thus, these compounds are useful in the treatment of glaucoma. The preferred route of administration for treating glaucoma is topically.

The exact amounts of each component in the topical composition depend on various factors. The amount of component A added to the topical composition is dependent on the $IC_{50}$ of component A, typically expressed in nanomolar (nM) units. For example, if the $IC_{50}$ of the medicament is 1 nM, the amount of component A will be from about 0.0001 to about 0.3%. If the $IC_{50}$ of the medicament is 10 nM, the amount of component A) will be from about 0.001 to about 1%. If the $IC_{50}$ of the medicament is 100 nM, the amount of component A will be from about 0.01 to about 10%. If the $IC_{50}$ of the medicament is 1000 nM, the amount of component A will be 1 to 100%, preferably 5% to 50%. If the amount of component A is outside the ranges specified above (i.e., lower), efficacy of the treatment may be reduced. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods provided herein are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, $2^{nd}$ Ed., (1976).

Component B may comprise a single ingredient or a combination of two or more ingredients. In the topical compositions, component B comprises a topical carrier. Suitable topical carriers comprise one or more ingredients selected from the group consisting of partially fluorinated hydrocarbons, phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include partially fluorinated hydrocarbons, propylene glycol, dimethyl isosorbide, and water, and even more particularly, partially fluorinated hydrocarbons, phosphate buffered saline, isotonic water, deionized water, monofunctional alcohols and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include partially fluorinated hydrocarbons, water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically 0 to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0 to about 95%.

Ingredient v) is a powder. The amount of ingredient v) in the topical composition is typically 0 to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. For ocular applications, specific powders include beta-cyclodextrin, hydroxypropyl cyclodextrin, and sodium polyacrylate. For gel dosing ocular formulations, sodium polyacrylate may be used.

Ingredient w) is a fragrance. The amount of ingredient w) in the topical composition is typically about 0 to about 0.5%, particularly, about 0.001 to about 0.1%. For ocular applications a fragrance is not typically used.

Ingredient x) is a pigment. Suitable pigments for skin applications include inorganic pigments, organic lake pigments, pearlescent pigments, and mixtures thereof. Inorganic pigments useful as provided herein include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful as provided herein include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful as provided herein include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%. For ocular applications a pigment is generally not used.

In another embodiment, topical pharmaceutical compositions for ocular administration are prepared typically comprising component A and B (a carrier), such as purified water, and one or more ingredients selected from the group consisting of y) sugars or sugar alcohols such as dextrans, particularly mannitol and dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, sodium chloride, potassium chloride, and combinations thereof.

Examples of cc) pH adjusting additives include HCl or NaOH in amounts sufficient to adjust the pH of the topical pharmaceutical composition for ocular administration to 4.5-7.5.

Component A may be included in kits comprising component A, a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

The following illustrative examples are to be considered to be non-limiting.

Specific procedures for the preparation of 8-methyl-8-azabicyclo[3.2.1]octan-3-yl and pyridin-4-ylmethanyl esters and amides are described in the following examples.

All temperatures are in degrees Centigrade. Reagents and starting materials were purchased from commercial sources or prepared following published literature procedures.

Unless otherwise noted, HPLC purification, when appropriate, was performed by redissolving the compound in a small volume of DMSO and filtering through a 0.45 micron (nylon disc) syringe filter. The solution was then purified using, for example, a 50 mm Varian Dynamax HPLC 21.4 mm Microsorb Guard-8 $C_8$ column. A typical initial eluting mixture of 40-80% MeOH:$H_2O$ was selected as appropriate for the target compound. This initial gradient was maintained for 0.5 minutes then increased to 100% MeOH:0% $H_2O$ over 5 minutes. 100% MeOH was maintained for 2 more minutes before re-equilibration back to the initial starting gradient. A typical total run time was 8 minutes. The resulting fractions were analyzed, combined as appropriate, and then evaporated to provide purified material.

Proton magnetic resonance ($^1H$ NMR) spectra were recorded on either a Varian INOVA 600 MHz ($^1H$) NMR spectrometer, Varian INOVA 500 MHz ($^1H$) NMR spectrometer, Varian Mercury 300 MHz ($^1H$) NMR spectrometer, or a Varian Mercury 200 MHz ($^1H$) NMR spectrometer. All spectra have been determined in the solvents indicated. Although chemical shifts are reported in ppm downfield of tetramethylsilane, they are referenced to the residual proton peak of the respective solvent peak for $^1H$ NMR. Interproton coupling constants are reported in Hertz (Hz).

Analytical LCMS spectra were obtained using a Waters ZQ MS ESI instrument with an Alliance 2695 HPLC and a 2487 dual wavelength UV detector. Spectra were analyzed at 254 and 230 nm. Samples were passed through a Waters Symmetry C18 4.6×75 mm 3.5 μm column with or without a guard column (3.9×20 mm 5 μm). Gradients were run with mobile phase A: 0.1% formic acid in $H_2O$ and mobile phase B: ACN with a flow rate of 0.8 mL/min. Two gradients are illustrated in Table 1.

TABLE 1

| Gradient A | | | Gradient B | | |
|---|---|---|---|---|---|
| Time | A % | B % | Time | A % | B % |
| 0.00 | 80.0 | 20.0 | 0.00 | 80.0 | 20.0 |
| 1.00 | 80.0 | 20.0 | 1.00 | 80.0 | 20.0 |
| 6.00 | 25.0 | 75.0 | 6.00 | 25.0 | 75.0 |
| 7.00 | 5.0 | 95.0 | 7.00 | 5.0 | 95.0 |
| 8.00 | 5.0 | 95.0 | 8.00 | 5.0 | 95.0 |
| 9.00 | 80.0 | 20.0 | 9.00 | 80.0 | 20.0 |
| 12.00 | 80.0 | 20.0 | 12.00 | 80.0 | 20.0 |

The settings for the MS probe were a cone voltage at 38 mV and a desolvation temperature at 250° C. Any variations in these methods are noted below.

The following preparations illustrate procedures for the preparation of intermediates and methods for the preparation of 8-methyl-8-azabicyclo[3.2.1]octan-3-yl and pyridin-4-ylmethanyl alkyl, ester and amide derivatives.

EXAMPLES

Example 1. Preparation of (1R,3S,5S)-8-methyl-8-azabicyclo[3.2.]octan-3-yl 3-((tert-butoxycarbonyl)amino)-2-phenylpropanoate

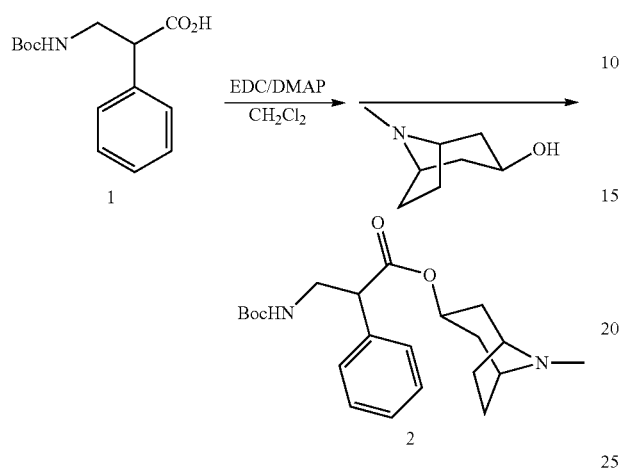

To 3-((tert-butoxycarbonyl)amino)-2-phenylpropanoic acid in CH$_2$Cl$_2$ was added EDC, DMAP and 3-((tert-butoxycarbonyl)amino)-2-phenylpropanoic acid and the solution was stirred overnight. The mixture was poured into NaHCO$_3$(sat) and extracted with CH$_2$Cl$_2$, dried (Na$_2$SO$_4$), filtered and evaporated to give crude 2. Column chromatography EtOAc-Hexanes gave pure (1R,3S,5S)-8-methyl-8-azabicyclo[3.2.1]octan-3-yl 3-((tert-butoxycarbonyl)amino)-2-phenylpropanoate.

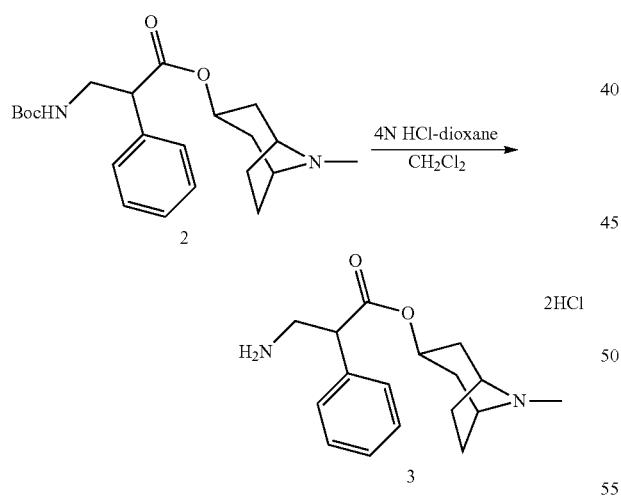

Example 2. Preparation of (1R,3S,5S)-8-methyl-8-azabicyclo[3.2.1]octan-3-yl 3-amino-2-phenylpropanoate Dihydrochloride To (1R,3S,5S)-8-methyl-8-azabicyclo[3.2.]octan-3-yl 3-((tert-butoxycarbonyl)amino)-2-phenylpropanoate in CH$_2$Cl$_2$ was added 4 N HCl-dioxane and the solution was stirred overnight. The solvents were evaporated and dried to give (1R,3S,5S)-8-methyl-8-azabicyclo[3.2.1]octan-3-yl 3-amino-2-phenylpropanoate dihydrochloride (E3).

Following the procedures above, and substituting the appropriate starting materials, certain compounds provided herein, including those of Table 2, can be made.

TABLE 2

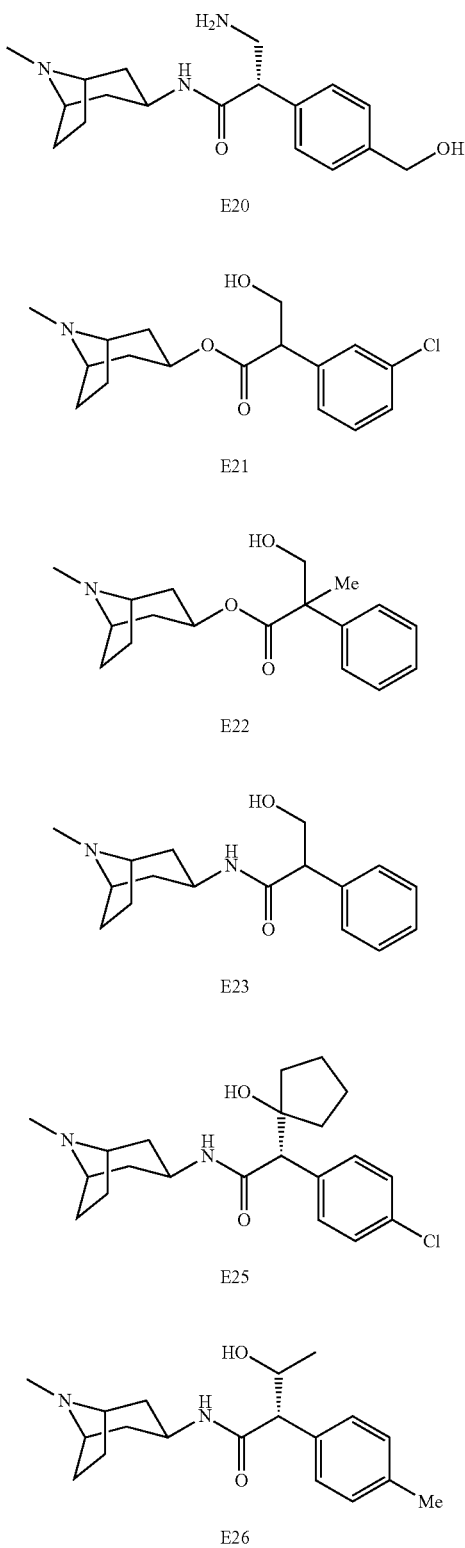

TABLE 2-continued
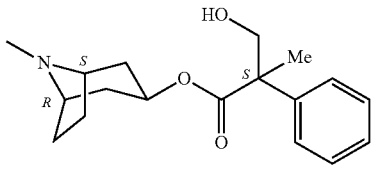
E27
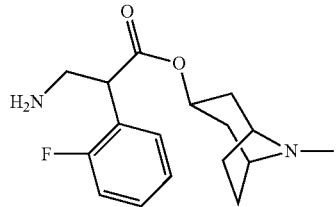
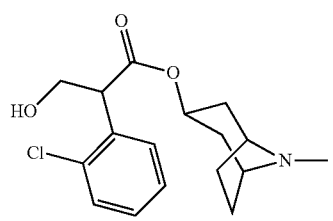 [SMILES: CN1C2CCC1CC(OC(=O)C(CO)c1ccccc1Cl)C2]
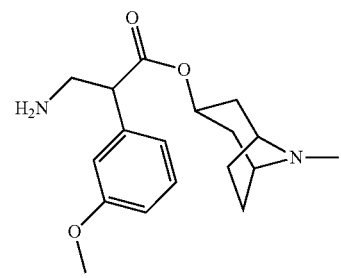
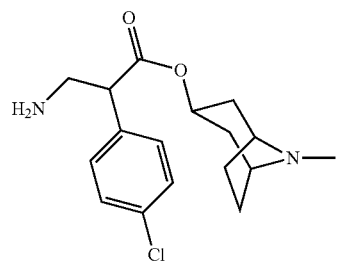 [SMILES: CN1C2CCC1CC(OC(=O)C(CN)c1ccc(Cl)cc1)C2]
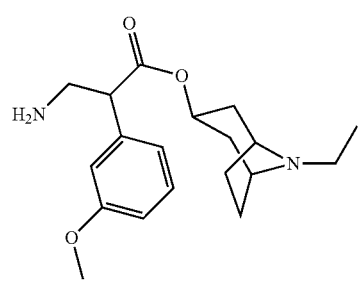
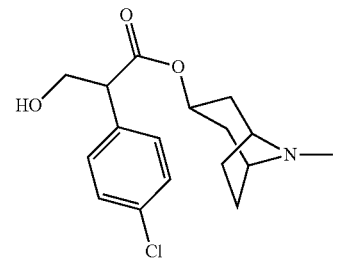 [SMILES: CN1C2CCC1CC(OC(=O)C(CO)c1ccc(Cl)cc1)C2]
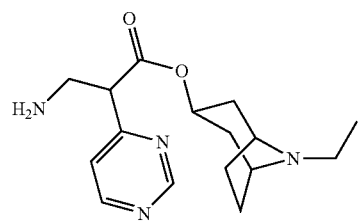
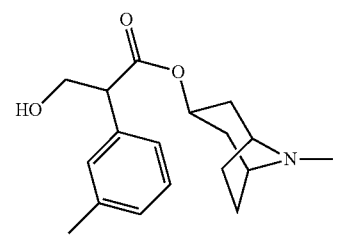 [SMILES: Cc1cccc(C(CO)C(=O)OC2CC3CCC(C2)N3C)c1]
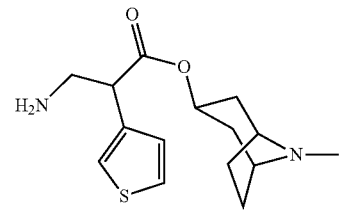
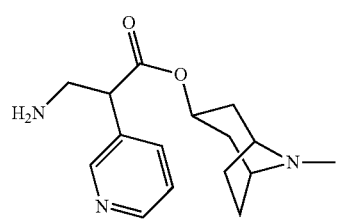 [SMILES: CN1C2CCC1CC(OC(=O)C(CN)c1cccnc1)C2]
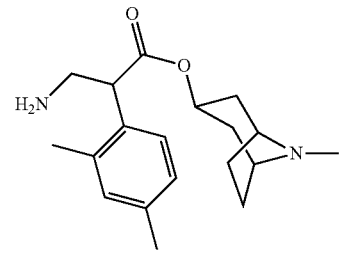 [SMILES: Cc1ccc(C(CN)C(=O)OC2CC3CCC(C2)N3C)c(C)c1]

TABLE 2-continued
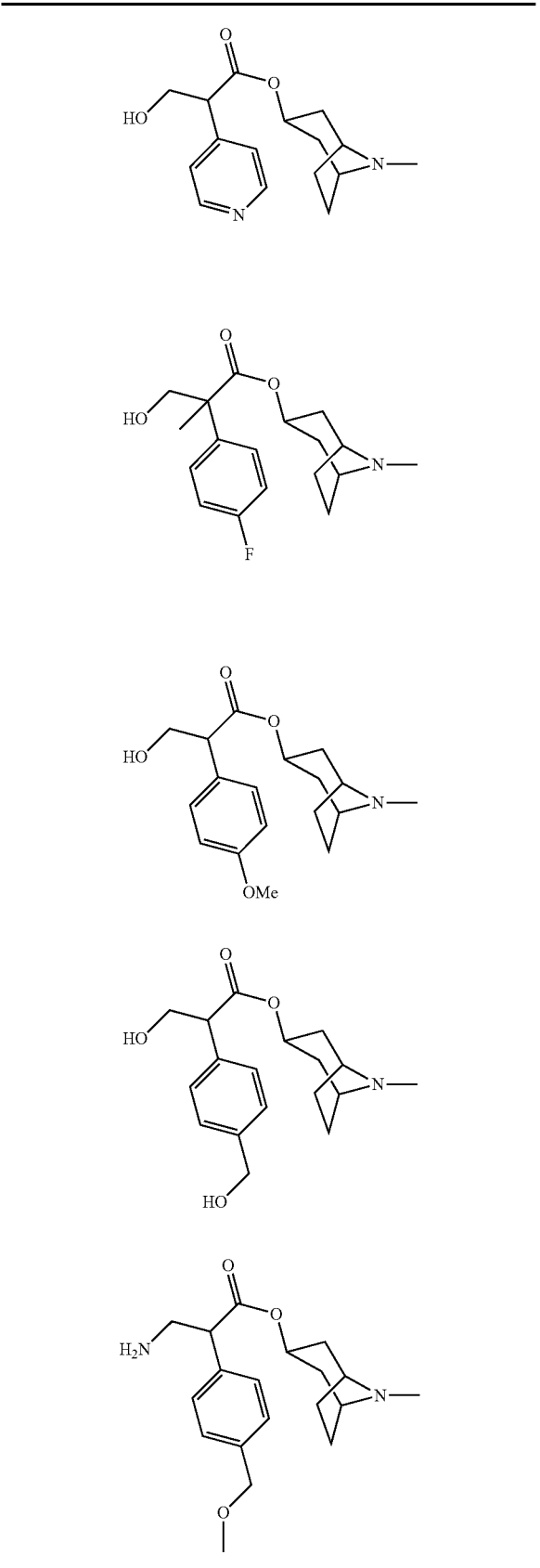
TABLE 2-continued
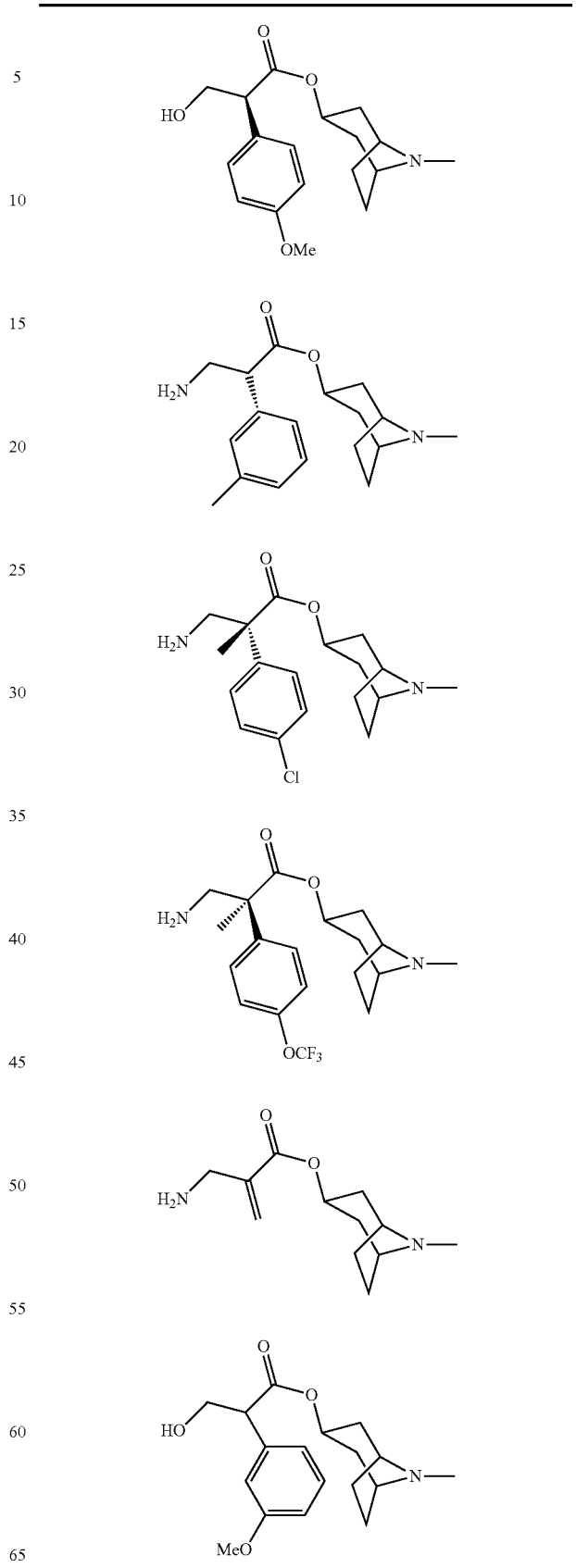

TABLE 2-continued
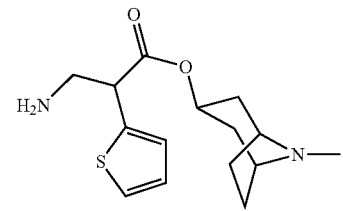 [SMILES: CN1C2CCC1CC(OC(=O)C(CN)c1cccs1)C2]
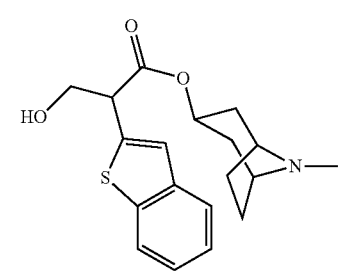 [SMILES: CN1C2CCC1CC(OC(=O)C(CO)c1cc3ccccc3s1)C2]
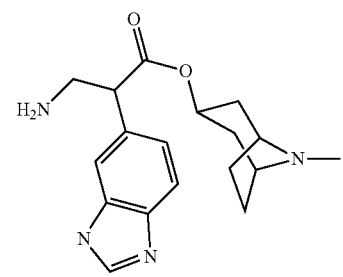 [SMILES: CN1C2CCC1CC(OC(=O)C(CN)c1ccc3nc[nH]c3c1)C2]
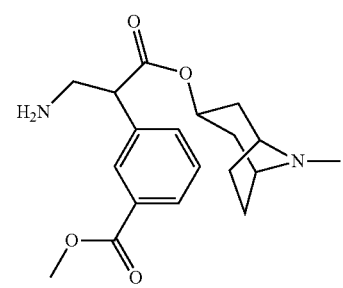 [SMILES: COC(=O)c1cccc(C(CN)C(=O)OC2CC3CCC(C2)N3C)c1]
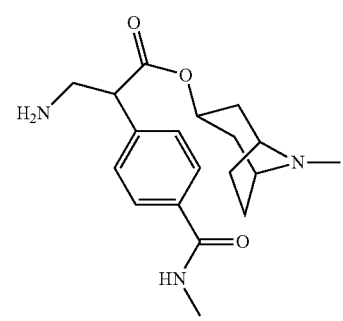 [SMILES: CNC(=O)c1ccc(C(CN)C(=O)OC2CC3CCC(C2)N3C)cc1]
TABLE 2-continued
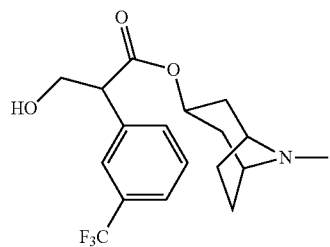 [SMILES: CN1C2CCC1CC(OC(=O)C(CO)c1cccc(C(F)(F)F)c1)C2]
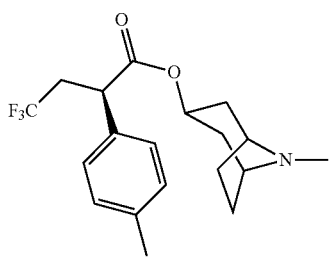 [SMILES: Cc1ccc([C@@H](CC(F)(F)F)C(=O)OC2CC3CCC(C2)N3C)cc1]
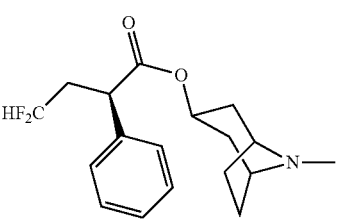
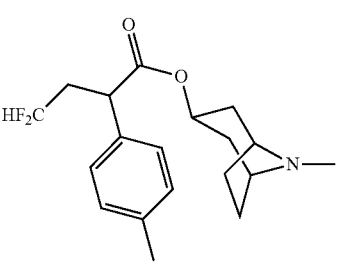
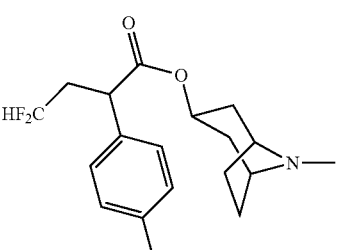

TABLE 2-continued
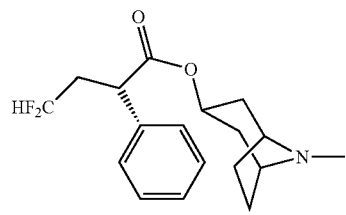
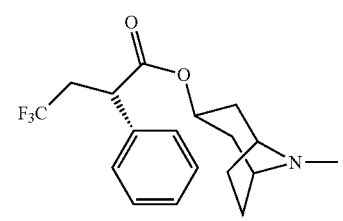
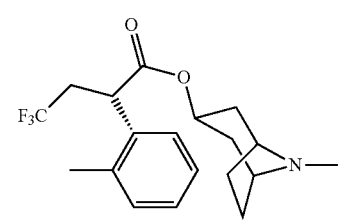
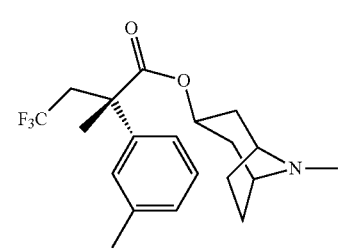
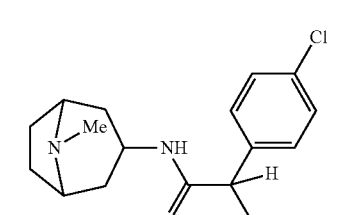
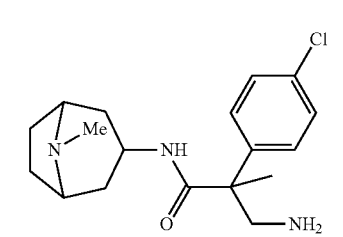
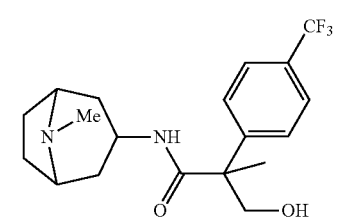 [SMILES: CN1C2CCC1CC(NC(=O)C(C)(CO)c1ccc(C(F)(F)F)cc1)C2]
TABLE 2-continued
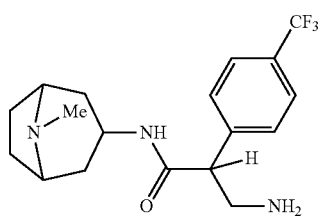 [SMILES: CN1C2CCC1CC(NC(=O)C(CN)c1ccc(C(F)(F)F)cc1)C2]
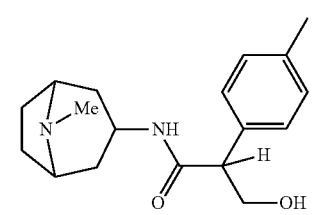 [SMILES: Cc1ccc(C(CO)C(=O)NC2CC3CCC(C2)N3C)cc1]
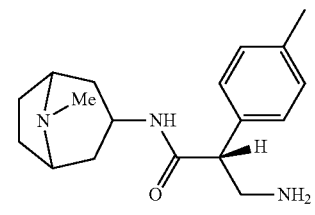 [SMILES: Cc1ccc([C@H](CN)C(=O)NC2CC3CCC(C2)N3C)cc1]
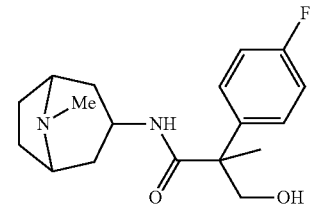 [SMILES: CN1C2CCC1CC(NC(=O)C(C)(CO)c1ccc(F)cc1)C2]
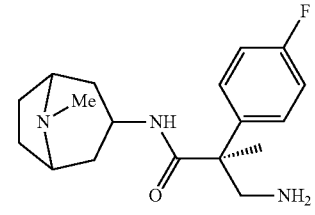 [SMILES: CN1C2CCC1CC(NC(=O)[C@](C)(CN)c1ccc(F)cc1)C2]
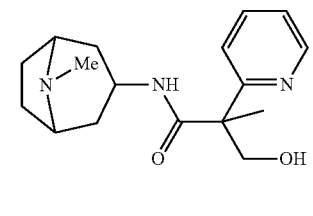 [SMILES: CN1C2CCC1CC(NC(=O)C(C)(CO)c1ccccn1)C2]
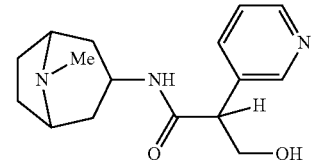 [SMILES: CN1C2CCC1CC(NC(=O)C(CO)c1cccnc1)C2]

TABLE 2-continued
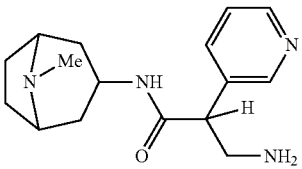 [SMILES: CN1C2CCC1CC(NC(=O)C(CN)c1cccnc1)C2]
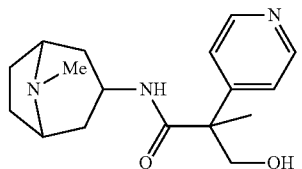 [SMILES: CN1C2CCC1CC(NC(=O)C(C)(CO)c1ccncc1)C2]
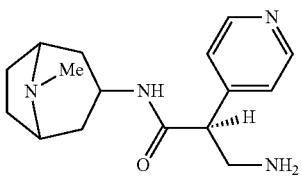 [SMILES: CN1C2CCC1CC(NC(=O)[C@H](CN)c1ccncc1)C2]
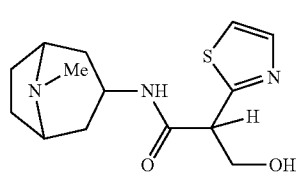 [SMILES: CN1C2CCC1CC(NC(=O)C(CO)c1nccs1)C2]
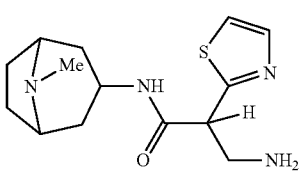 [SMILES: CN1C2CCC1CC(NC(=O)C(CN)c1nccs1)C2]
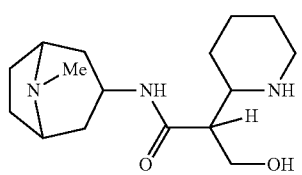 [SMILES: CN1C2CCC1CC(NC(=O)C(CO)C1CCCCN1)C2]
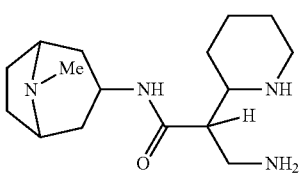 [SMILES: CN1C2CCC1CC(NC(=O)C(CN)C1CCCCN1)C2]
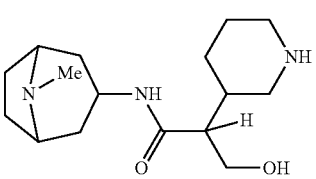 [SMILES: CN1C2CCC1CC(NC(=O)C(CO)C1CCCNC1)C2]
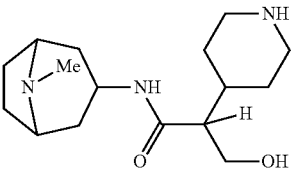 [SMILES: CN1C2CCC1CC(NC(=O)C(CO)C1CCNCC1)C2]
TABLE 2-continued
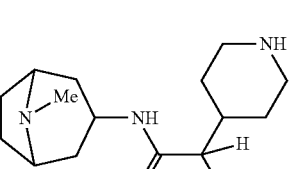
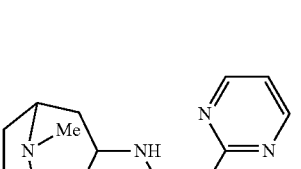
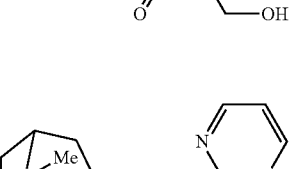
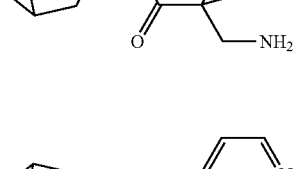
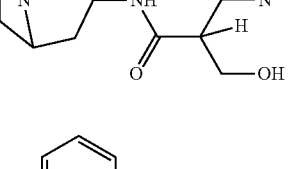
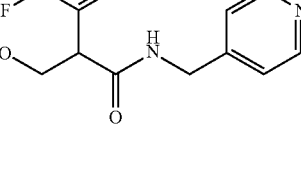
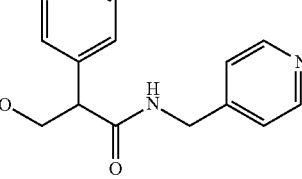
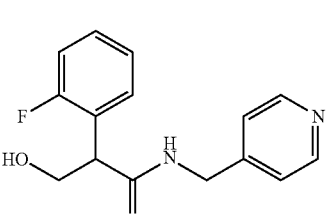
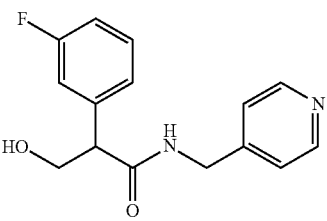 [SMILES: O=C(NCc1ccncc1)C(CO)c1cccc(F)c1]

TABLE 2-continued
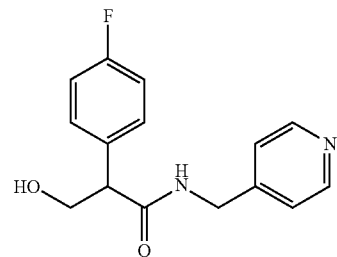 [SMILES: O=C(NCc1ccncc1)C(CO)c1ccc(F)cc1]
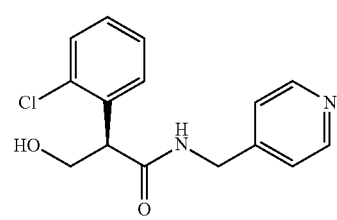 [SMILES: O=C(NCc1ccncc1)[C@@H](CO)c1ccccc1Cl]
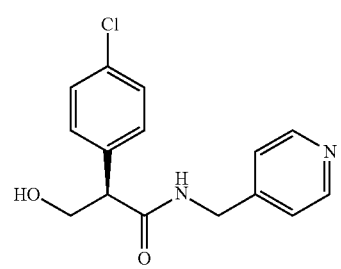 [SMILES: O=C(NCc1ccncc1)[C@@H](CO)c1ccc(Cl)cc1]
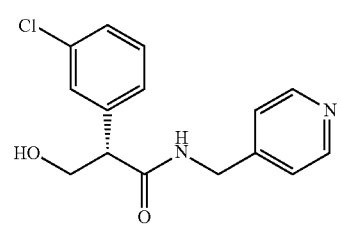
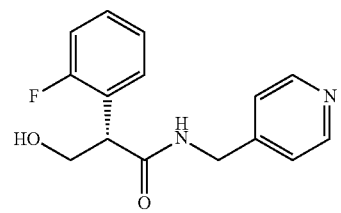 [SMILES: O=C(NCc1ccncc1)[C@H](CO)c1ccccc1F]
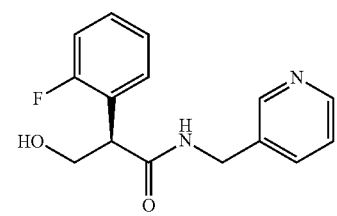 [SMILES: O=C(NCc1cccnc1)[C@@H](CO)c1ccccc1F]
TABLE 2-continued
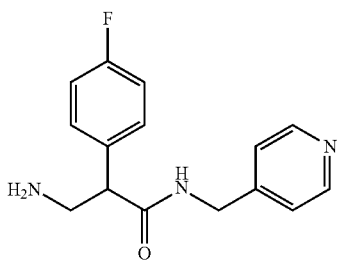 [SMILES: NCC(C(=O)NCc1ccncc1)c1ccc(F)cc1]
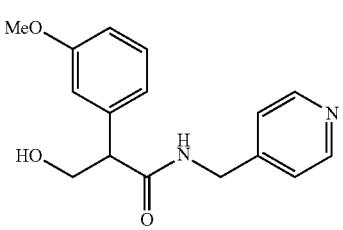 [SMILES: COc1cccc(C(CO)C(=O)NCc2ccncc2)c1]
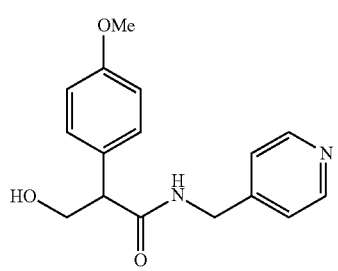 [SMILES: COc1ccc(C(CO)C(=O)NCc2ccncc2)cc1]
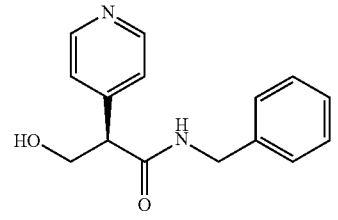 [SMILES: O=C(NCc1ccccc1)[C@@H](CO)c1ccncc1]
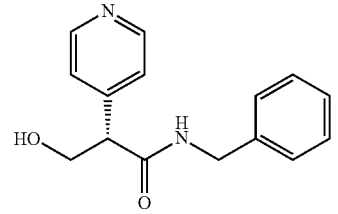 [SMILES: O=C(NCc1ccccc1)[C@H](CO)c1ccncc1]
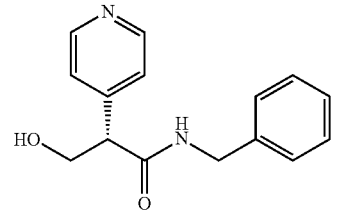 [SMILES: O=C(NCc1ccccc1)[C@H](CO)c1ccncc1]

TABLE 2-continued
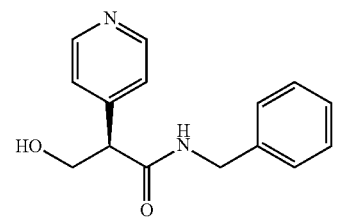 [SMILES: O=C(NCc1ccccc1)[C@@H](CO)c1ccncc1]
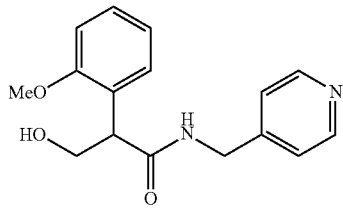 [SMILES: COc1ccccc1C(CO)C(=O)NCc1ccncc1]
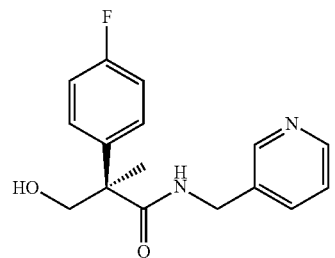 [SMILES: C[C@@](CO)(C(=O)NCc1cccnc1)c1ccc(F)cc1]
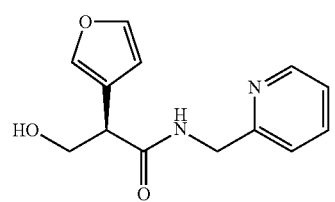 [SMILES: O=C(NCc1ccccn1)[C@@H](CO)c1ccoc1]
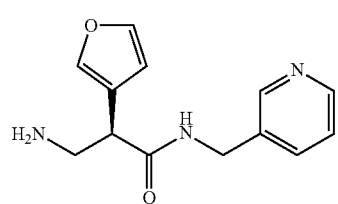 [SMILES: NC[C@H](C(=O)NCc1cccnc1)c1ccoc1]
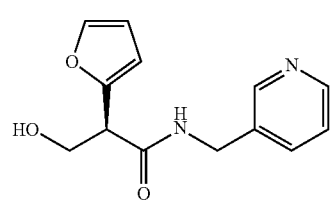 [SMILES: O=C(NCc1cccnc1)[C@@H](CO)c1ccco1]
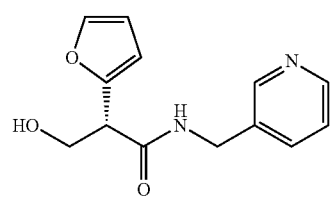 [SMILES: O=C(NCc1cccnc1)[C@H](CO)c1ccco1]
TABLE 2-continued
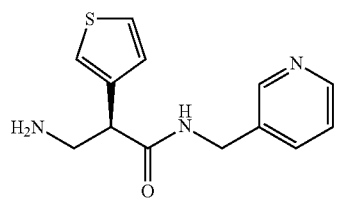
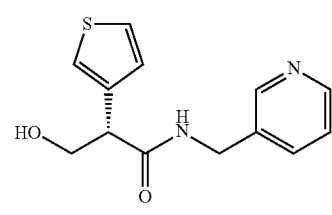 [SMILES: O=C(NCc1cccnc1)[C@H](CO)c1ccsc1]
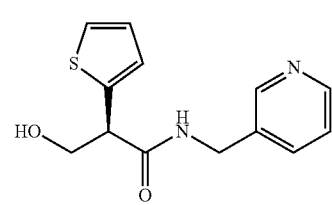 [SMILES: O=C(NCc1cccnc1)[C@@H](CO)c1cccs1]
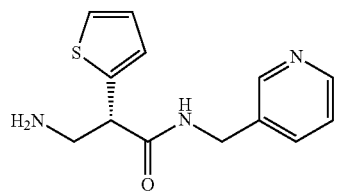 [SMILES: NC[C@@H](C(=O)NCc1cccnc1)c1cccs1]
Using techniques known in the art the following compounds could be made:
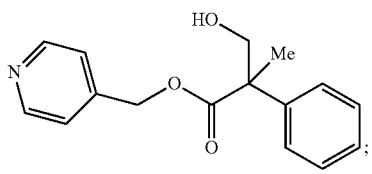
E101
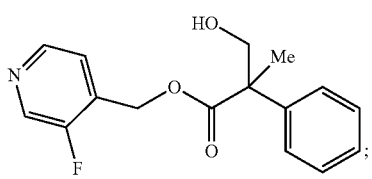
E102
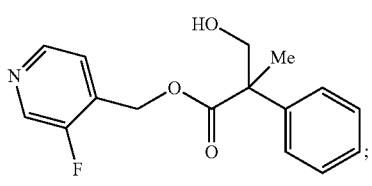
E103

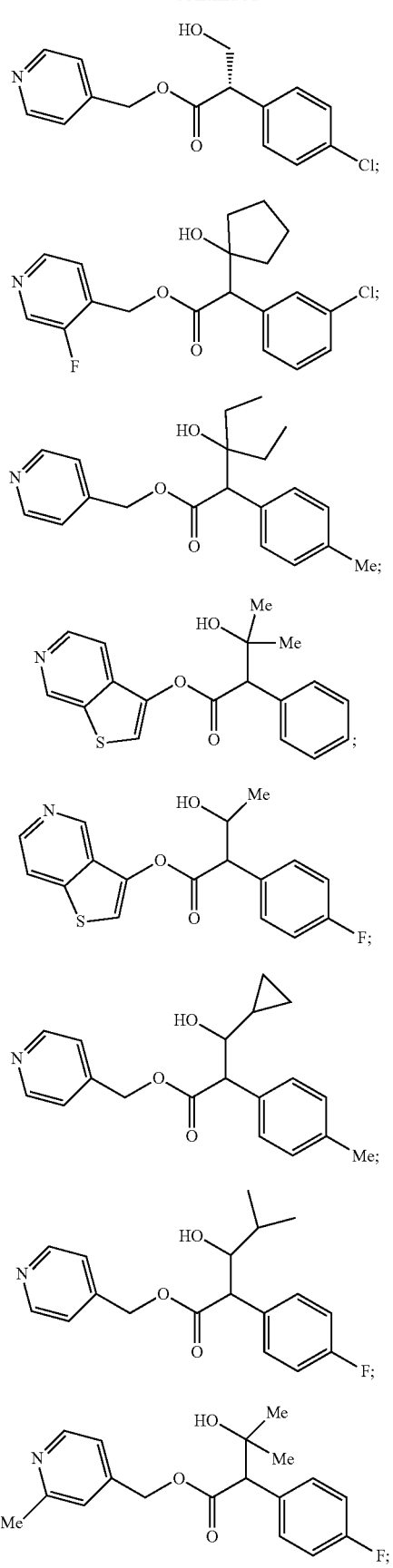
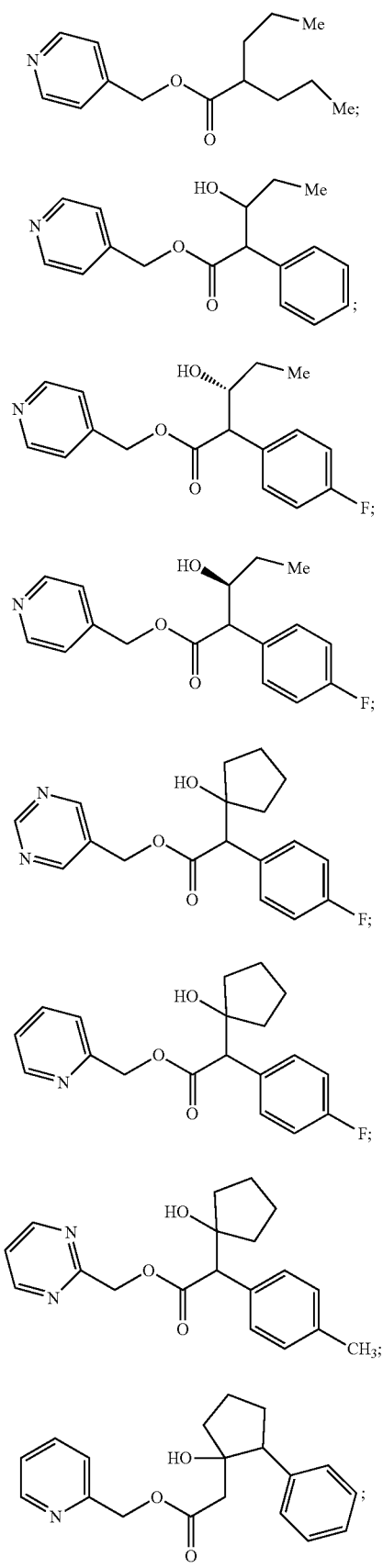

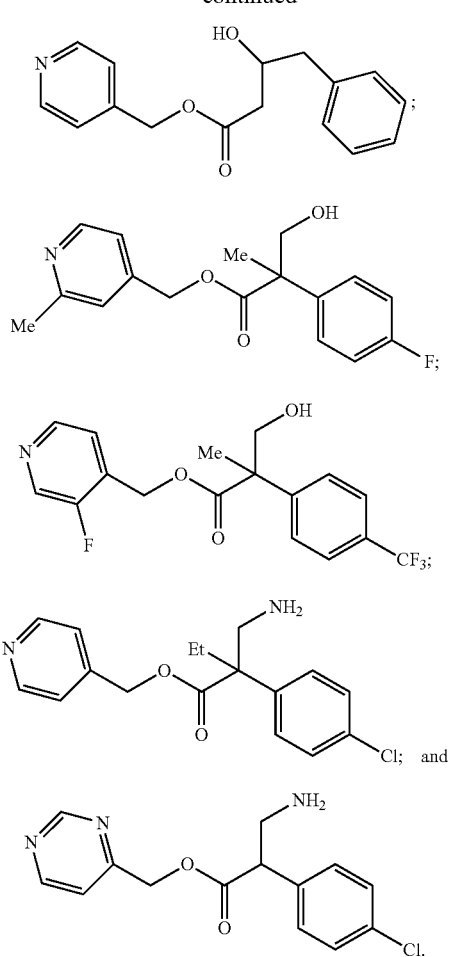

Example 3. Inducing Form Deprivation Myopia in Mouse

The mouse is a good preclinical model to evaluate pharmacological treatments for myopia since the mouse eye has a very similar structure and biochemistry as the human eye, and previous studies have confirmed the utility of the mouse model of myopia. The mouse eye also has pharmacological targets similar to those in the human eye. The results show that 8-methyl-8-azabicyclo[3.2.1]octan-3-yl analogues given topically prior to the eye experiencing a procedure to induce myopia can avert some or all of the myopic changes. It has been shown that the relevant all of muscarinic receptor types in the fibroblasts of the tough outer connective tissue coating of the eye, the sclera are similar for the mouse eye and the human eye.

In general, form deprivation myopia ("FDNT") in the mouse can be reliably created by attaching a −IOD lens over the mouse eye for 6 weeks. This causes an increase in axial length and refractive error of the mouse eye. In this procedure, the eyes will be treated with 8-methyl-8-azabicyclo[3.2.1]octan-3-yl analogues once daily for 1-14 days prior to placing the −IOD lens over the eye. Initial experimental groups (n=8/group) will include: a) 8-methyl-8-azabicyclo[3.2.1]octan-3-yl analogues treatment starting day 21 without lens placement and continuing for four weeks; b) −IOD lens placement at day 35 after two weeks of 8-methyl-8-azabicyclo[3.2.1]octan-3-yl analogues treatment and continuing lens treatment for 4 weeks; c) −IOD lens placement at day 35 after one week of 8-methyl-8-azabicydo[3.2.1]octan-3-yl analogues treatment and continuing lens treatment for 4 weeks; d) −IOD lens placement at day 35 without prior 8-methyl-8-azabicyclo[3.2.1]octan-3-yl analogues treatment and continuing for 4 weeks; e) control without lens or 8-methyl-8-azabicydo[3.2.1]octan-3-yl analogues.

After experimental treatment begins, the mice will be monitored every two weeks for axial length and refractive error changes using procedures as previously published. Refractions and biometry measurements will be carried out every two weeks. Axial length is measured with the in vivo 'Optic Low Coherence interferometry'(OLCTAcMaster). Refraction is measured by automated eccentric photo refractor. Details of the methods have been previously described (Barathi V A & Beuerman R W, 2011; Barathi et al 2013).

Example 4. Effect of 8-methyl-8-azabicydo[3.2.1]octan-3-yl Analogues Eye Drops Prior to Inducing Foral Deprivation Myopia in a Mouse Model Methods:

Animals: Breeding pair B6J (*Mus musculus*) mice were obtained from Jackson Lab and produced offspring. Naive control animals were housed in groups of 6 while experimental animals were housed individually in standard mouse cages after 21 days of age at 25° C. on a schedule of 12:12 h of light on and off with mouse pellets and water available ad libitum.

Murine Myopia Model: A −IOD contact lens (PMMA Contact Lens in Grey Tint, 8.5 mm diameter, 8 mm base curve, refractive Index: 1.43, axial, thickness: 0.5 mm) was placed over the right eye on day 21 by gluing to an annulus of Velcro, and then attaching to a matching piece of Velcro that had been previously sutured to the skin around the eye. The spectacle lenses were cleaned daily in dim light and left eyes were uncovered and served as controls. All optical appliances were removed on postnatal day 63.

Treatment Protocols:

Delayed FDM was induced in four groups of mice: groups 1-4. Group 1 (n=6, 3 batch) received a daily 10 μL of 1% topical application of 8-methyl-8-azabicyclo[3.2.1]octan-3-yl analogues on day 35 for 4 weeks, and Group 2 (n=6, 3 batch) received daily 10 μL of 1% topical application of 8-methyl-8-azabicydo[3.2.1]octan-3-yl analogues on day 21 for 2 weeks and then −IOD lens was applied to induce myopia (pATG+LIM) for 4 weeks, Group 3 (n=6, 3 batch) was treated with the −IOD lens alone to induce myopia (lens applied on day 21 and continued for 6 weeks), Group 4 (n=3 [both eyes are naive control], 3 batch) was used as naive control. The right eye was used as an experimental and left eye was served as a contralateral control in all groups. Note that experimentally-induced myopia in mice has been consistently found to have contralateral effects both for induction and for drug intervention.

Ocular biometry assessment: Refractions and biometry measurements were recorded every week until the end of the study. Axial length was measured with in vivo Optic Low Coherence Interferometry) (OLCI-AcMaster). Refraction was measured by automated eccentric photo refractor. Details of the methods were previously described (Barathi V A et al, 2013; Barathi V A & Beuerman R W, 2011).

Statistical analysis: Statistical analysis was performed using SPSS software (Version 11.0, Chicago, 145 USA). All results were expressed with mean±standard error (SEM). All values for the lens-induced eyes were statistically compared with those of the fellow eyes within the same group using a paired sample t-test. The mean interocular difference was used for an independent sample t-test between the experimental and normal groups. Statistical analysis among groups was performed by one-way analysis of variance (ANOVA), and statistical significance was considered when P<0.05.

Results:

8-methyl-8-azabicyclo[3.2.1]octan-3-yl analogues treatment delayed induction of myopia. Treatment is effective in diminishing the effect on axial length and refraction that would otherwise be expected. Eyes receiving 8-methyl-8-azabicyclo[3.2.1]octan-3-yl analogues for 2 weeks prior to induction of myopia (−10 D lens for 4 weeks) remained hyperopic.

Topical pharmaceutical compositions for treatment of myopia are prepared by conventional methods and formulated as shown in Table 3.

TABLE 3

| Ingredient | Amount (wt %) |
| --- | --- |
| 8-methyl-8-azabicyclo[3.2.1]octan-3-yl ester | 0.10 |
| Dextran 70 | 0.1 |
| Hydroxypropyl methylcellulose | 0.3 |
| Sodium Chloride | 0.77 |
| Potassium chloride | 0.12 |
| Disodium EDTA | 0.05 |
| Benzalkonium chloride | 0.01 |
| HCl and/or NaOH | pH 5.5-6.5 |
| Purified water | q.s. to 100% |

A compound provided herein is used as the 8-methyl-8-azabicyclo[3.2.1]octan-3-yl and pyridin-4-ylmethanyl ester derivative. When the composition is topically administered to the eyes once daily, the above composition decreases the rate of myopia progression.

Example 5

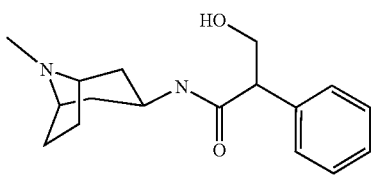

E23

Example 1 is repeated using 8-methyl-8-azabicyclo[3.2.1]octan-3-yl 3-hydroxy-2-phenylpropanamide methansulfonate (E23) provided herein. When administered as a drop 2 times per day, the above composition substantially decreases the rate of myopia progression in a human subject aged 6 years old.

Example 6

Example 1 is repeated using an 8-methyl-8-azabicyclo[3.2.1]octan-3-yl and pyridin-4-ylmethanyl amide provided herein. When administered as a drop twice per day, the above composition prevents the onset of myopia in a pre-myopic patient.

Example 7

Example 1 is repeated using 8-methyl-8-azabicyclo[3.2.1]octan-3-yl 2-(4-fluorophenyl)-3-hydroxypropanoate toluensulfonate provided herein. When administered as a drop thrice per day, the above composition substantially decreases allergic symptoms and relieves dry eye syndrome.

Example 8

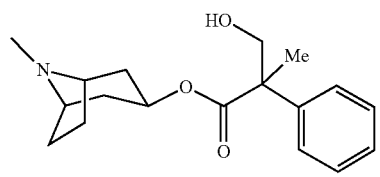

E22

Example 1 is repeated using substantially the R isomer of 8-methyl-8-azabicyclo[3.2.1]octan-3-yl 3-hydroxy-2-methyl-2-phenylpropanoate hydrochloride (E22R) provided herein. When administered as a drop as needed, the above composition substantially decreases hyperemia, redness and ocular irritation.

Example 9

Example 1 is repeated using substantially the S-isomer of 8-methyl-8-azabicyclo[3.2.1]octan-3-yl 3-hydroxy-2-methyl-2-phenylpropanoate hydrochloride (E44S) provided herein. When administered as a drop 4 times per day, the above composition substantially slows the rate of progression of myopia.

Example 10

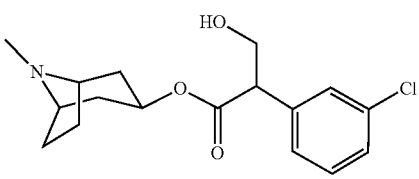

E21

Example 1 is repeated using 8-methyl-8-azabicyclo[3.2.1]octan-3-yl 2-(3-chlorophenyl)-3-hydroxypropanoate hydrochloride (E21) provided herein. When administered as a drop twice per day, the above composition substantially decreases intraocular pressure.

Example 11

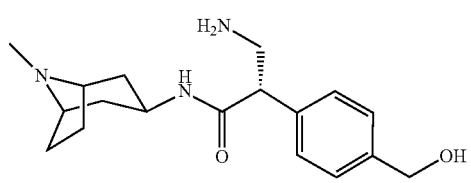

E20

Example 1 is repeated using (S)-3-amino-2-(4-(hydroxymethyl)phenyl)-N-((1R,3-endo,5S)-8-methyl-8-azabicyclo[3.2.]octan-3-yl)propanamide ditosylate (E20S) provided herein. When administered as a drop twice per day, the above composition substantially decreases ocular pressure, allergic symptoms and relieves dry eye syndrome.

Topical pharmaceutical compositions for prevention and treatment of myopia are prepared by conventional methods and formulated as shown in Table 4.

TABLE 4

| Ingredient | Amount (wt %) |
|---|---|
| 8-methyl-8-azabicyclo[3.2.1]octan-3-yl ester | 0.50 |
| SFA | 95.00 |
| 95% EtOH | q.s. to 100% |

Topical pharmaceutical compositions for prevention and treatment of myopia are prepared by conventional methods and formulated as shown in Table 5.

TABLE 5

| Ingredient | Amount (wt %) |
|---|---|
| 8-methyl-8-azabicyclo[3.2.1]octan-3-yl amide | 0.50 |
| SFA | 99.00 |
| 95% EtOH | q.s. to 100% |

Topical pharmaceutical compositions for prevention and treatment of myopia are prepared by conventional methods and formulated as shown in Table 6.

TABLE 6

| Ingredient | Amount (wt %) |
|---|---|
| 8-methyl-8-azabicyclo[3.2.1]octan-3-yl ester | 0.50 |
| SFA | 99.00 |
| 95% EtOH | q.s. to 100% |

Topical pharmaceutical compositions for prevention and treatment of myopia are prepared by conventional methods and formulated as shown in Table 7.

TABLE 7

| Ingredient | Amount (wt %) |
|---|---|
| pyridin-4-ylmethanyl amide | 0.50 |
| SFA | 99.00 |
| 95% EtOH | q.s. to 100% |

Topical pharmaceutical compositions for prevention and treatment of myopia are prepared by conventional methods and formulated as shown in Table 8.

TABLE 8

| Ingredient | Amount (wt %) |
|---|---|
| pyridin-4-ylmethanyl ester | 0.50 |
| SFA | q.s. to 100% |

Figure 2:
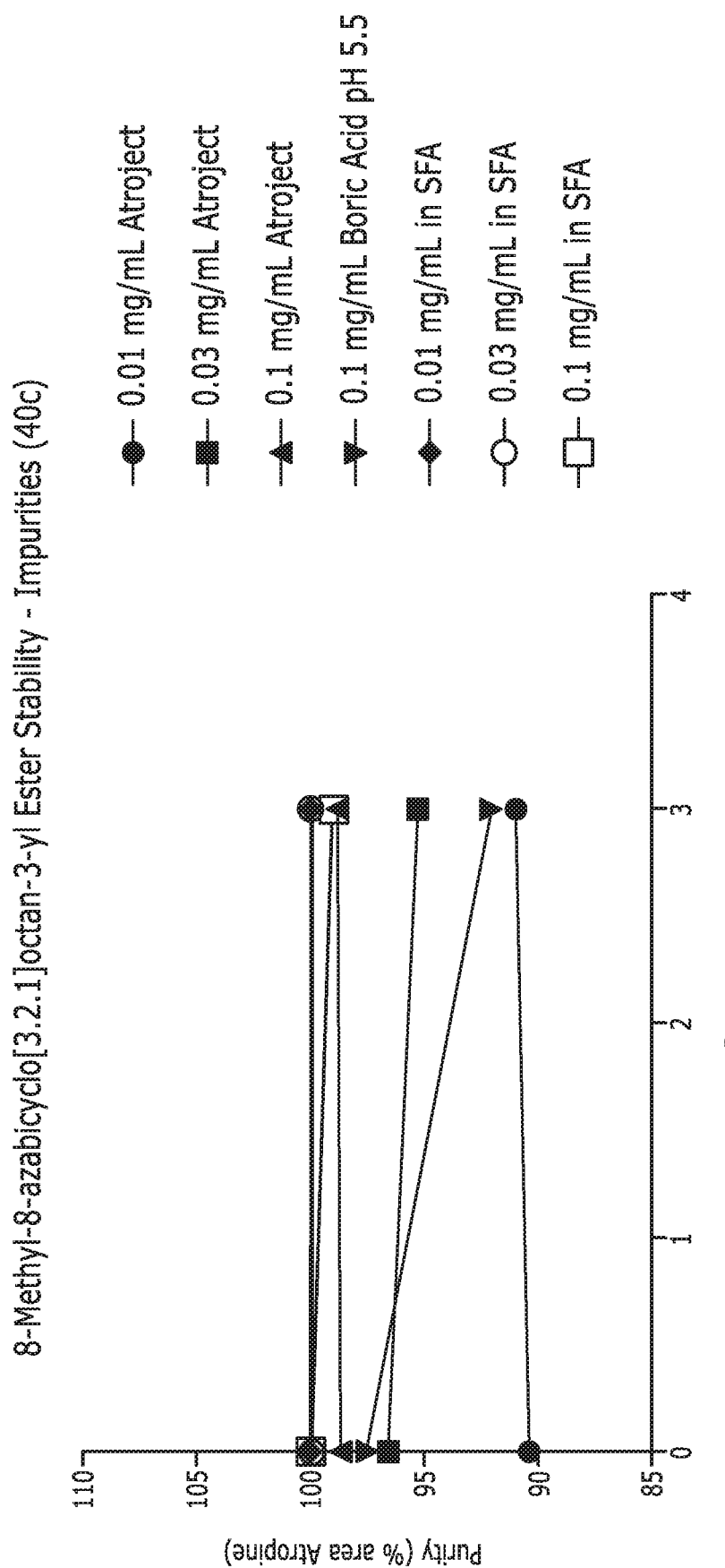
FIG. 2 shows the superior stability of the SFA formulation of Table 8 as compared to aqueous formulations for other compounds provided herein.
Figure 3:
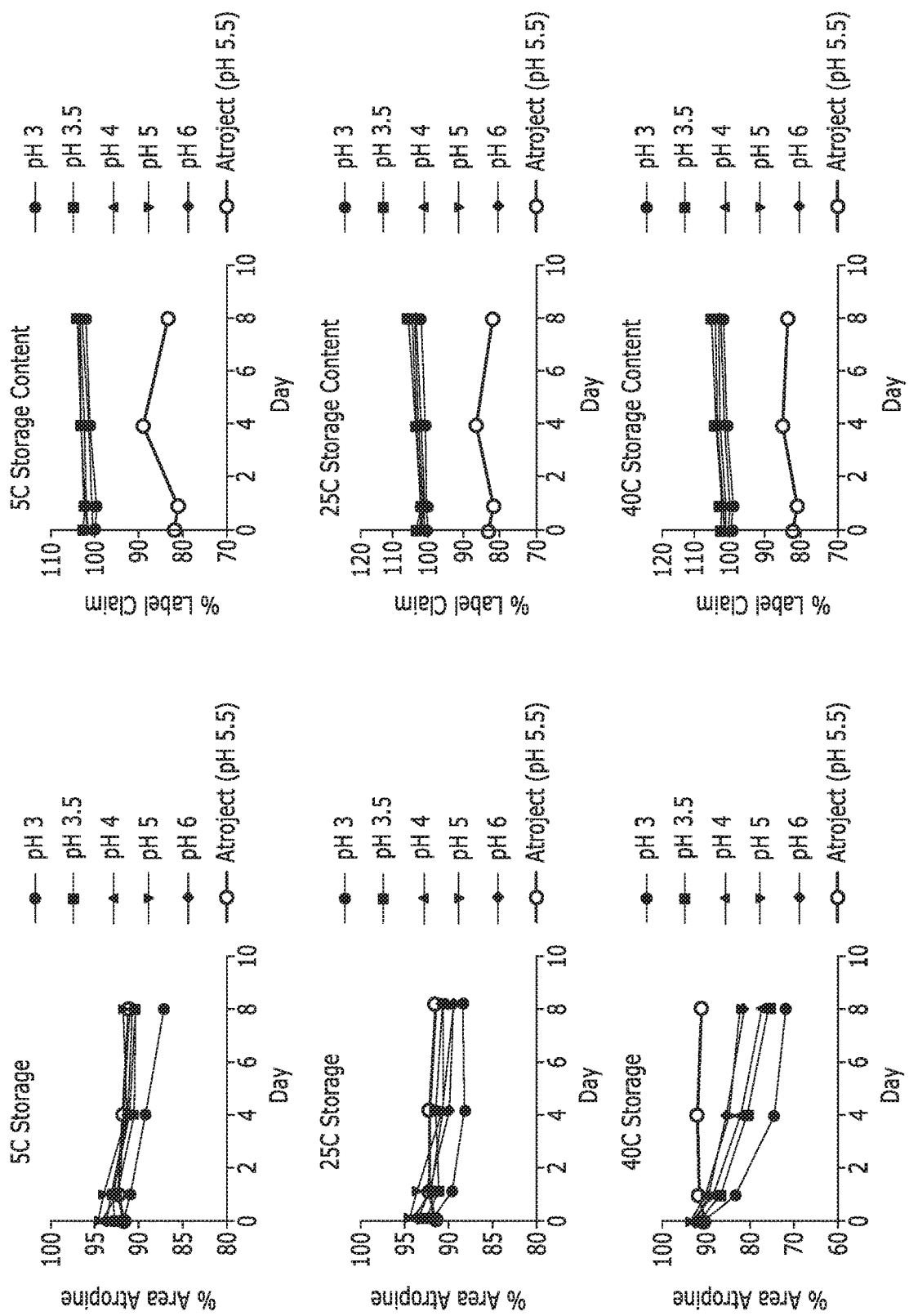
FIG. 3 shows the superior stability of the SFA formulation of Table 8 as compared to aqueous formulations for other compounds provided herein.

FIG. 1, FIG. 2, and FIG. 3 show the superior stability of the above SFA formulation (Table 8) as compared to aqueous formulations for compounds provided herein.

Topical Ointment pharmaceutical composition for prevention and treatment of myopia is prepared by conventional methods and formulated as shown in Table 9.

TABLE 9

| Ingredient | Amount (wt %) |
|---|---|
| pyridin-4-ylmethanyl ester | 1.0 |
| Mineral Oil | 20.0 |
| White Petrolatum | 79.0 |

Example 12. Preparation of Salt Forms

Methanesulfonic acid (2.5 eq. or 1.2 eq.) is added drop-wise to a stirred solution of a compound provided herein (5.0 g 1 eq.) in DCM (dichloromethane) (10 vol). The reaction mixture is stirred at room temperature over 4 hours and completion of the reaction is ascertained by HPLC. A gradual solvent switch from dichloromethane to 2-BuOH is then carried out. The solution of the DCM solvent is removed by distillation under vacuum. Next, two substantial portions of 2-BuOH are added to the residue followed by vacuum distillation. 2-BuOH (10 vol) is added to the residue and the reaction mixture is stirred at room temperature over a period of 15 hours.

The dimesylate salt or monomesylate salt is isolated as a solid by filtration under nitrogen. After washing with 2-BuOH (2×1 vol) and heptane (2×1 vol), the solid is dried in a vacuum oven at 50° C. over 15 hours. Various salt forms of the compounds provided herein may be prepared according to this procedure.

Example 13. Synthesis of endo 8-methyl-8-azabicyclo[3.2.1]octan-3-yl 3-amino-2-phenylpropanoate Dihydrochloride (3)

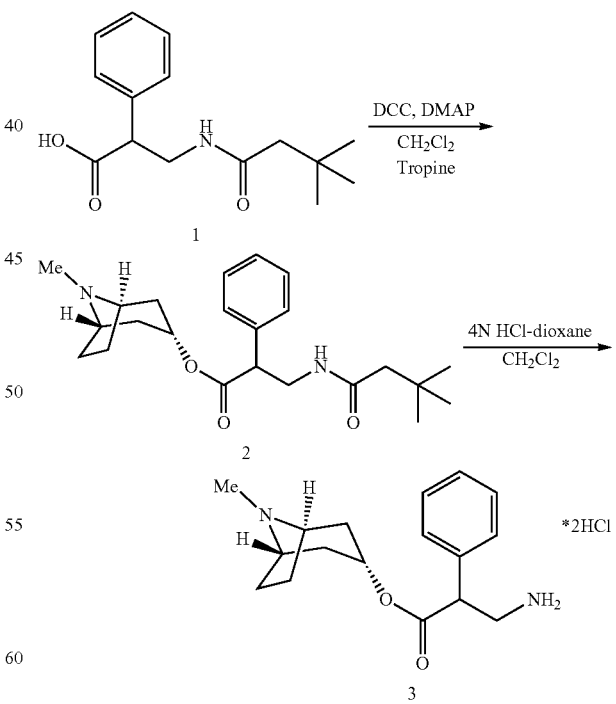

To 3-((tert-butoxycarbonyl)amino)-2-phenylpropanoic acid in CH$_2$Cl$_2$ was added, DCC, DMAP and tropine and the solution was stirred overnight at room temperature. The mixture was then filtered and extracted with NaHCO$_3$ (saturated) and NaCl (saturated), dried (Na₂SO₄) filtered and evaporated. Column chromatography 0-5% MeOH—CH₂Cl₂ gave pure endo 8-methyl-8-azabicyclo[3.2.1]octan-3-yl 3-((tert-butoxycarbonyl)amino)-2-phenylpropanoate (2, 30%).

To endo 8-methyl-8-azabicyclo[3.2.1]octan-3-yl 3-((tert-butoxycarbonyl)amino)-2-phenylpropanoate (2) in CH₂Cl₂ was added HCl (4 N in dioxane) and solution was stirred overnight. The solvents were evaporated to give endo 8-methyl-8-azabicyclo[3.2.1]octan-3-yl 3-amino-2-phenyl-propanoate dihydrochloride (3, >90%).

Example 14. Synthesis of endo 8-methyl-8-azabicyclo[3.2.1]octan-3-yl 4,4,4-trifluoro-2-phenylbutanoate (5)

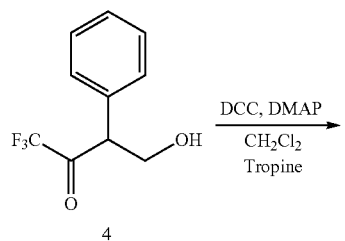

To 4,4,4-trifluoro-2-phenylbutanoic acid (4) in CH₂Cl₂ was added, DCC, DMAP and tropine and the solution was stirred overnight at room temperature. The mixture was then filtered and extracted with NaHCO₃ (saturated) and NaCl (saturated), dried (Na₂SO₄) filtered and evaporated. Column chromatography 0-10% MeOH—CH₂Cl₂ gave pure endo 8-methyl-8-azabicyclo[3.2.1]octan-3-yl 4,4,4-trifluoro-2-phenylbutanoate (5, 36%).

Example 15. Synthesis of exo 3-hydroxy-N-(8-methyl-8-azabicyclo[3.2.1]octan-3-yl)-2-phenylpropanamide (7)

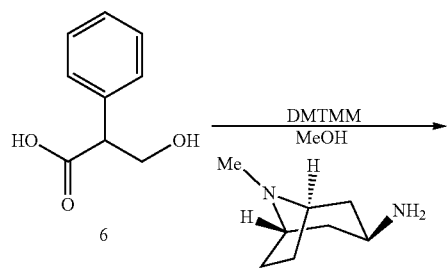

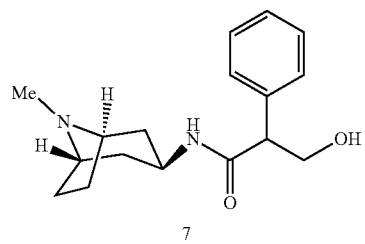

To tropic acid (6) in MeOH was added exo-8-methyl-3-amino-azabicyclo [3.2.1] octane and DMTMM and the solution was stirred at room temperature overnight. The mixture was evaporated and taken up in EtOAC and NaHCO₃(sat). The pH of the aqueous was adjusted with a solution of K₂CO₃ to pH 10 and extracted further with 2-methyl THF. The solvents were dried (Na₂SO₄), filtered and evaporated. Column chromatography 0%-90% (EtOH/2N NH₃-MeOH (85/15) —CH₂Cl₂ gave pure exo-3-hydroxyN-(8-methyl-8-azabicyclo[3.2.1]octan-3-yl)-2-phenylpropanamide (7, 30%).

Example 16. Synthesis of 3-hydroxy-N-((6-methoxypyridin-3-yl)methyl)-2-phenylpropanamide (8)

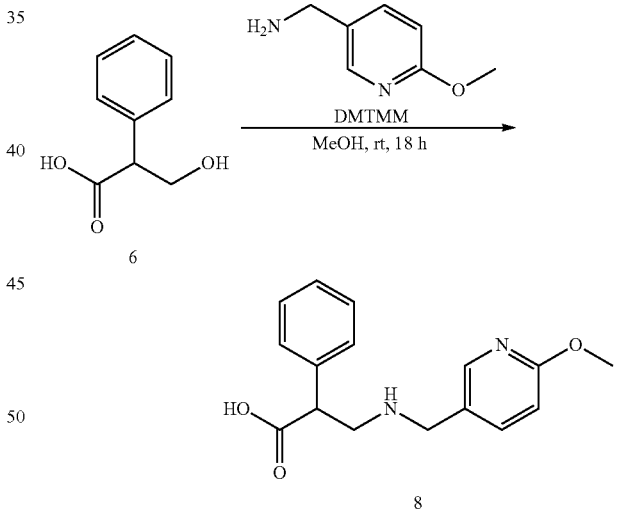

To tropic acid (6) in MeOH was added (6-methoxypyridin-3-yl)methanamine and DMTMM and the solution was stirred at room temperature overnight. The mixture was poured in water and extracted with ethyl acetate. The organics were washed with NaCl (saturated), dried (MgSO₄), filtered and evaporated. Column chromatography 0-8% MeOH—CH₂Cl₂ gave 3-hydroxy-N-((6-methoxypyridin-3-yl)methyl)-2-phenylpropanamide (8, 51%).

Using largely the procedures set forth in Examples 13-16 and substituting the appropriate starting materials, compounds of Table 10 were made.

TABLE 10

| Compound Structure | Compound Name |
|---|---|
| 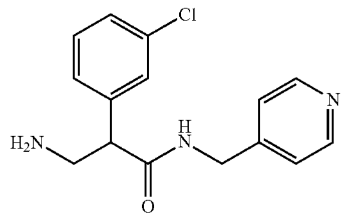 [SMILES: NCC(C(=O)NCc1ccncc1)c1cccc(Cl)c1] | 3-amino-2-(3-chlorophenyl)-N-(pyridin-4-ylmethyl)propanamide |
| 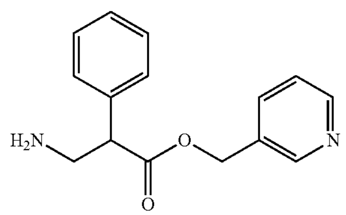 [SMILES: NCC(C(=O)OCc1cccnc1)c1ccccc1] | pyridin-3-ylmethyl 3-amino-2-phenylpropanoate |
| 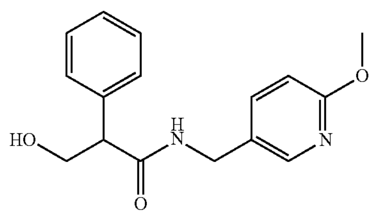 [SMILES: COc1ccc(CNC(=O)C(CO)c2ccccc2)cn1] | 3-hydroxy-N-((6-methoxypyridin-3-yl)methyl)-2-phenylpropanamide |
| 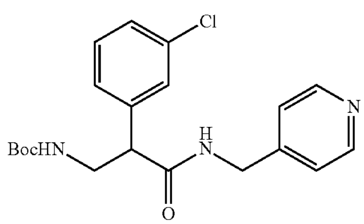 [SMILES: CC(C)(C)OC(=O)NCC(C(=O)NCc1ccncc1)c1cccc(Cl)c1] | tert-butyl (2-(3-chlorophenyl)-3-oxo-3-((pyridin-4-ylmethyl)amino)propyl)carbamate |
| 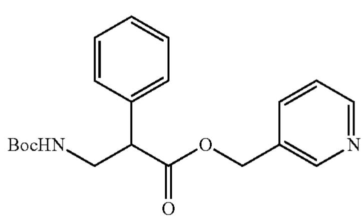 [SMILES: CC(C)(C)OC(=O)NCC(C(=O)OCc1cccnc1)c1ccccc1] | pyridin-3-ylmethyl 3-((tert-butoxycarbonyl)amino)-2-phenylpropanoate |
| 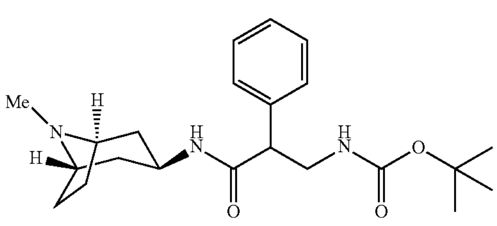 [SMILES: CN1[C@@H]2CC[C@H]1C[C@H](NC(=O)C(CNC(=O)OC(C)(C)C)c1ccccc1)C2] | Exo-rel-tert-butyl (3-(((1R,3S,5S)-8-methyl-8-azabicyclo[3.2.1]octan-3-yl)amino)-3-oxo-2-phenylpropyl)carbamimidate |
| 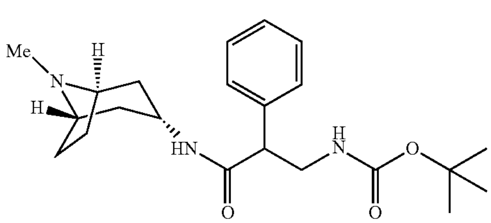 [SMILES: CN1[C@@H]2CC[C@H]1C[C@@H](NC(=O)C(CNC(=O)OC(C)(C)C)c1ccccc1)C2] | endo-rel-tert-butyl (3-(((1R,3S,5S)-8-methyl-8-azabicyclo[3.2.1]octan-3-yl)amino)-3-oxo-2-phenylpropyl)carbamate |

TABLE 10-continued

| Compound Structure | Compound Name |
|---|---|
| 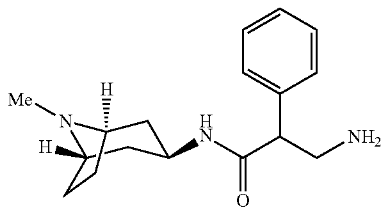 [SMILES: CN1[C@@H]2CC[C@H]1C[C@H](NC(=O)C(CN)c1ccccc1)C2] | 3-amino-N-((1R,3s,5S)-8-methyl-8-azabicyclo[3.2.1]octan-3-yl)-2-phenylpropanamide |
| 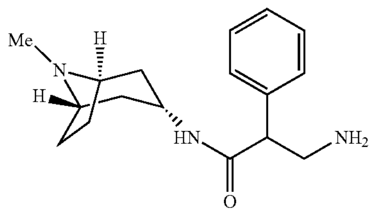 [SMILES: CN1[C@@H]2CC[C@H]1C[C@@H](NC(=O)C(CN)c1ccccc1)C2] | 3-amino-N-((1R,3r,5S)-8-methyl-8-azabicyclo[3.2.1]octan-3-yl)-2-phenylpropanamide |
| 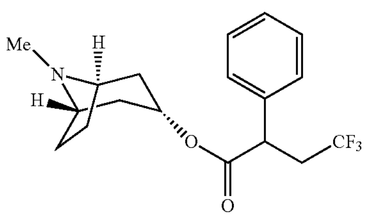 [SMILES: CN1[C@@H]2CC[C@H]1C[C@@H](OC(=O)C(CC(F)(F)F)c1ccccc1)C2] | endo 8-methyl-8-azabicyclo[3.2.1]octan-3-yl 4,4,4-trifluoro-2-phenylbutanoate |
| 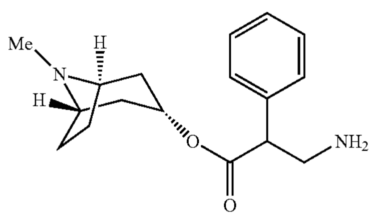 [SMILES: CN1[C@@H]2CC[C@H]1C[C@@H](OC(=O)C(CN)c1ccccc1)C2] | endo 8-methyl-8-azabicyclo[3.2.1]octan-3-yl 3-amino-2-phenylpropanoate |
| 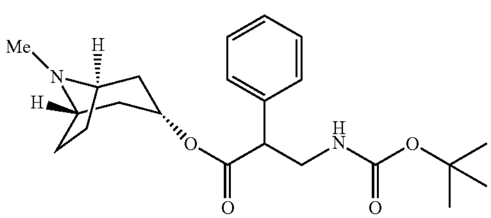 [SMILES: CN1[C@@H]2CC[C@H]1C[C@@H](OC(=O)C(CNC(=O)OC(C)(C)C)c1ccccc1)C2] | endo 8-methyl-8-azabicyclo[3.2.1]octan-3-yl 3-((tert-butoxycarbonyl)amino)-2-phenylpropanoate |
| 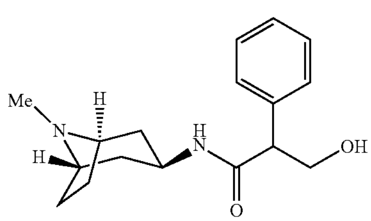 [SMILES: CN1[C@@H]2CC[C@H]1C[C@H](NC(=O)C(CO)c1ccccc1)C2] | exo 3-hydroxy-n-(8-methyl-8-azabicyclo[3.2.1]octan-3-yl)-2-phenylpropanamide |

TABLE 10-continued

| Compound Structure | Compound Name |
|---|---|
| 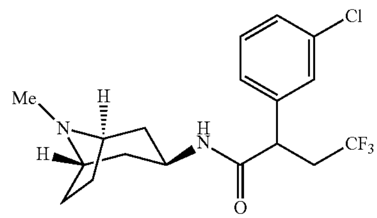 [SMILES: CN1[C@@H]2CC[C@H]1C[C@H](NC(=O)C(CC(F)(F)F)c1cccc(Cl)c1)C2] | exo2-(3-chlorophenyl)-4,4,4-trifluoro-8-methyl-8-azabicyclo[3.2.1]octan-3-yl)butanamide |
|  |  |

Example 17. Compound and Composition Storage and Stability

A compound provided herein is prepared and placed in a container for storage at ambient or elevated temperature. When the compound is stored in a polyolefin plastic container as compared to a polyvinyl chloride plastic container, discoloration of the compound is reduced, whether dissolved or suspended in a liquid composition (e.g., an aqueous or organic liquid solution), or as a solid. Without wishing to be bound by theory, the container reduces the compound's exposure to electromagnetic radiation, whether visible light (e.g., having a wavelength of about 380-780 nm) or ultraviolet (UV) light (e.g., having a wavelength of about 190-320 nm (UV-B light) or about 320-380 nm (UV-A light)). Some containers also include the capacity to reduce exposure of the container's contents to infrared light, or a second component with such a capacity. The containers used include those made from a polyolefin such as polyethylene, polypropylene, polyethylene terephthalate, polycarbonate, polymethylpentene, polybutene, or a combination thereof, especially polyethylene, polypropylene, or a combination thereof. The container may further be disposed within a second container, for example, a paper, cardboard, or foil container to further reduce exposure of the container's contents to UV, visible, or infrared light. Compounds and compositions benefiting from reduced discoloration, decomposition, or both during storage, include eye drop solutions that include a compound or composition thereof provided herein. Eye drop solutions may need storage lasting up to, or longer than, three months. The containers described herein may be eye drop containers. The containers may be in any form suitable to contain the contents; for example, a bag or a bottle.

Other suitable containers and packaging are described, for example, in International publication numbers WO 2018/159700, WO 2018/159701, and WO 2018/159702, and JP 6236167 B2, the contents of which are incorporated herein by reference.

Compositions disposed within the containers described may include: boric acid, D-mannitol, benzalkonium chloride, polyoxyl 40 stearate, polyethylene glycol 400, ethylenediamine tetraacetic acid, or a combination thereof; and water or another suitable solvent vehicle.

What is claimed is:

1. A compound, wherein the compound is:

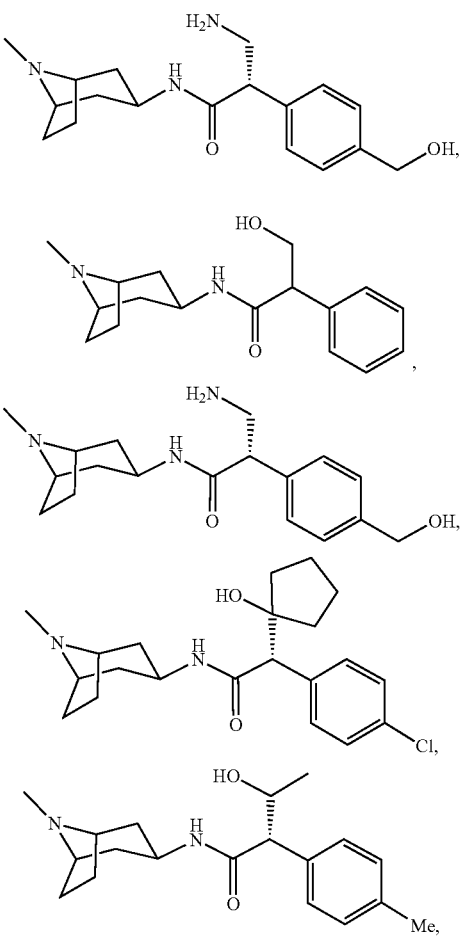

-continued
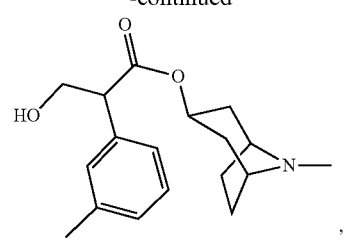
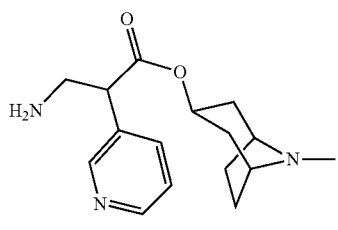
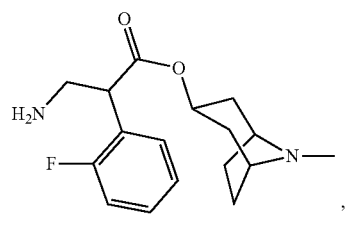
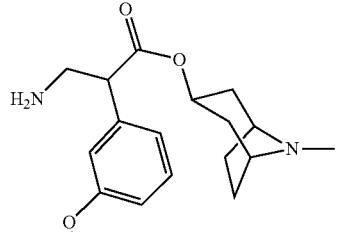
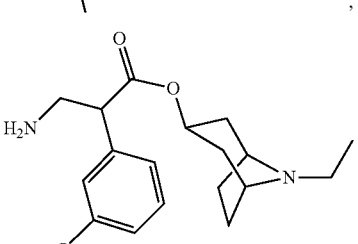
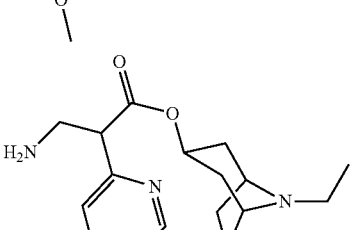
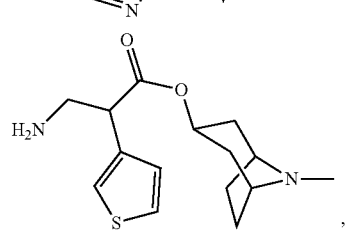
-continued
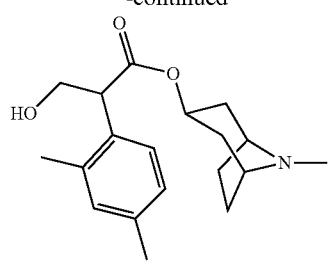
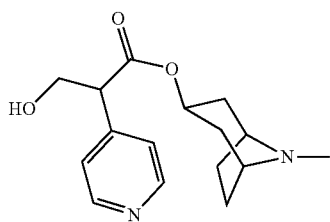
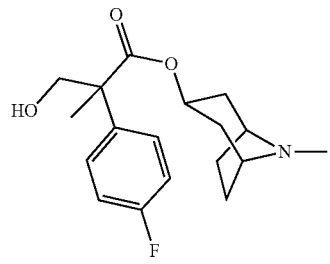
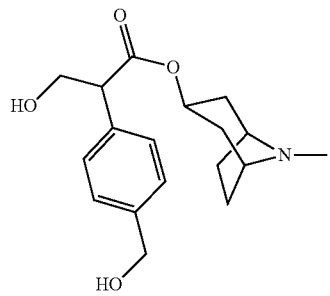
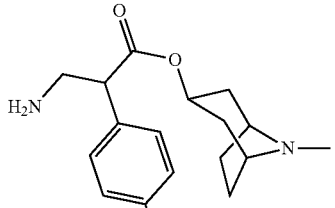
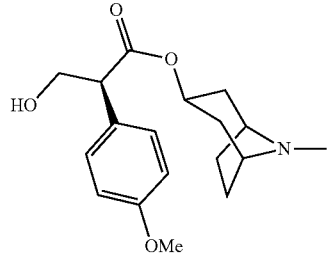

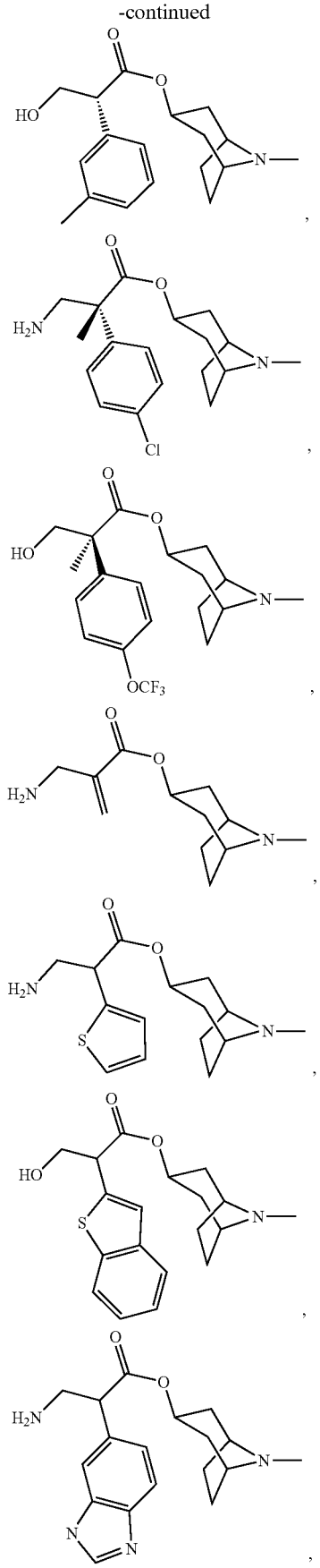
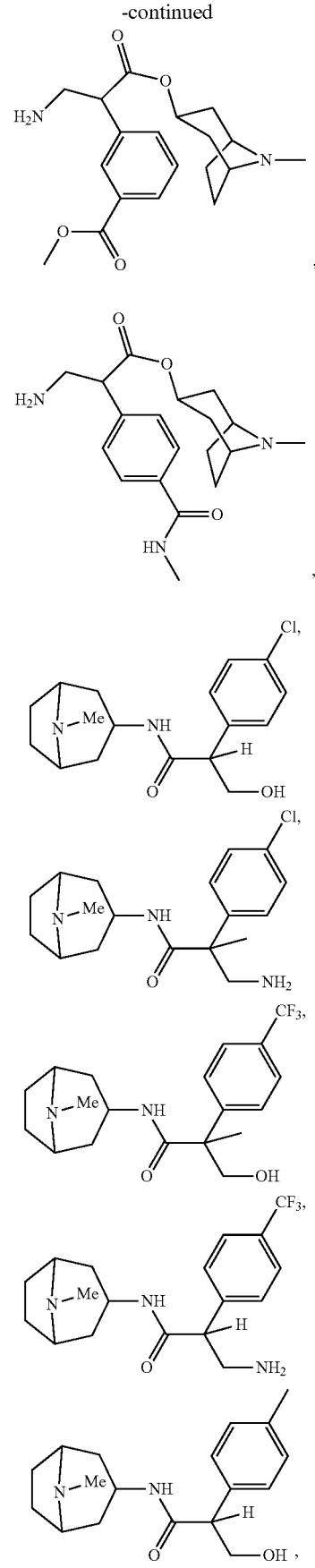

-continued
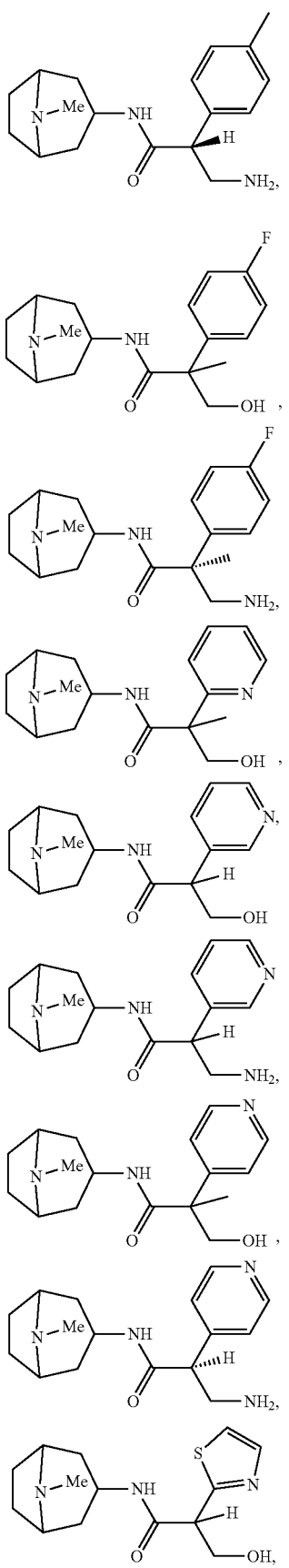
-continued
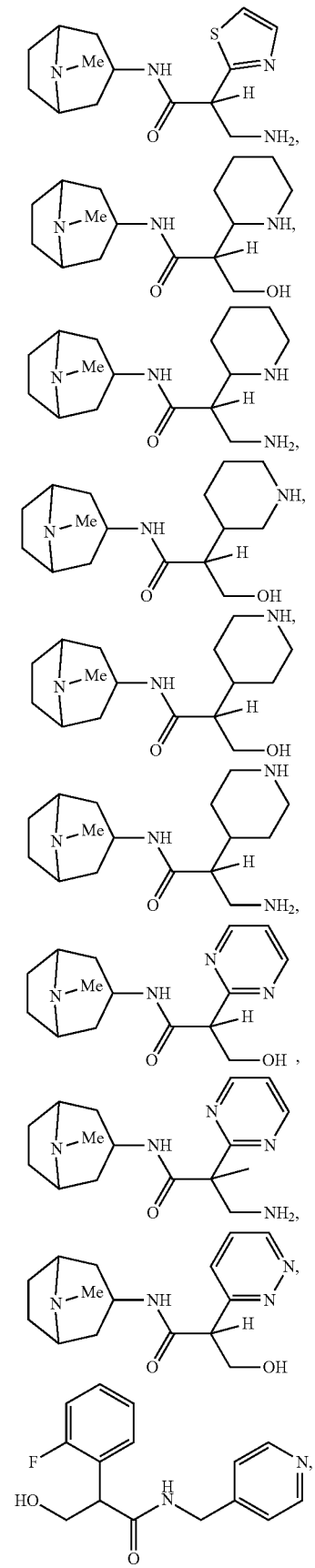

-continued

107
-continued
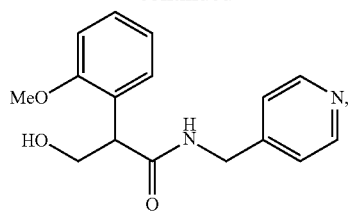
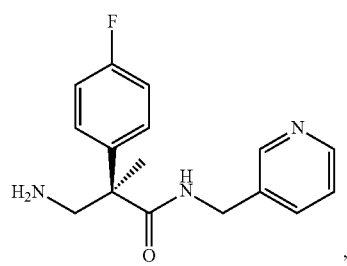
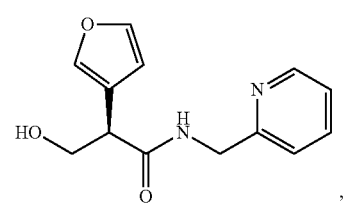
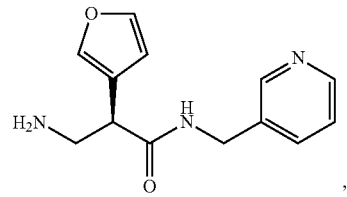
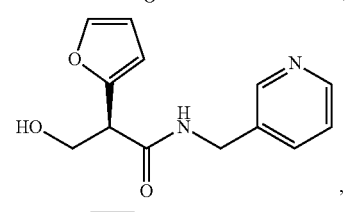
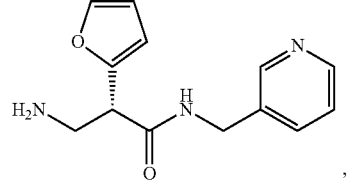
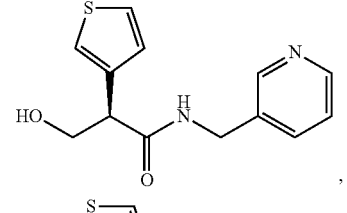
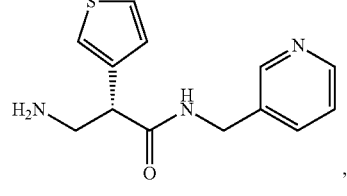
108
-continued
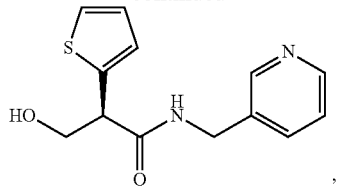
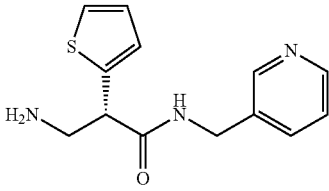
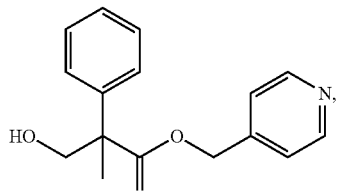
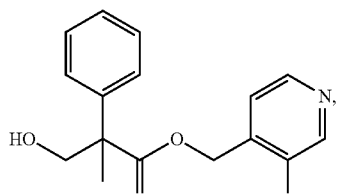
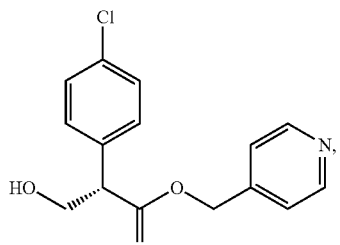
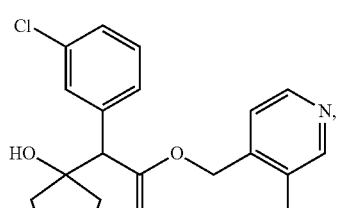
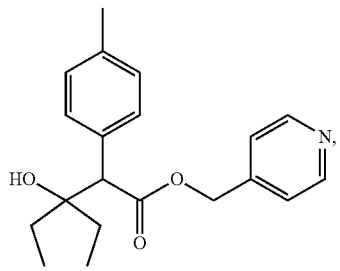

-continued
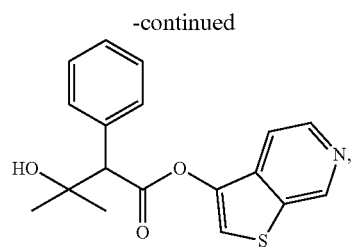
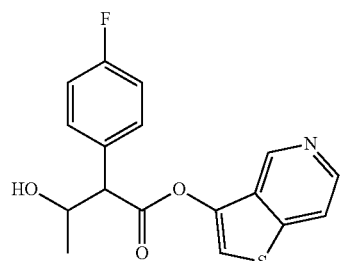
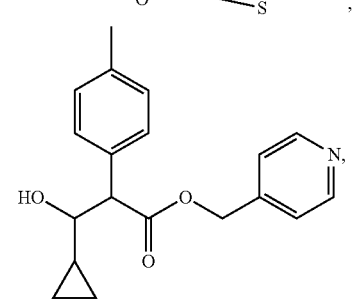
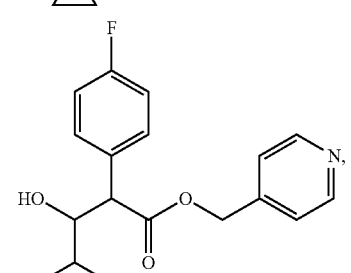
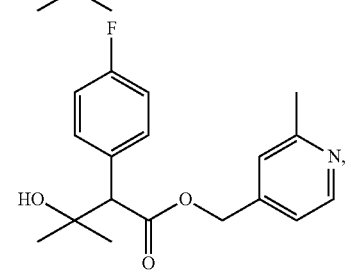
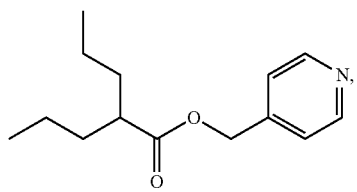
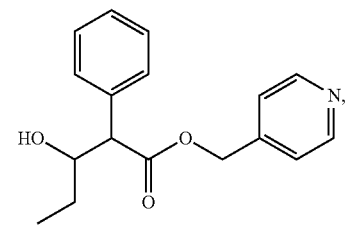
-continued
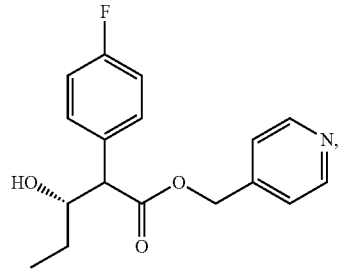
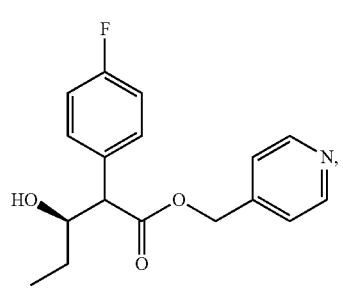
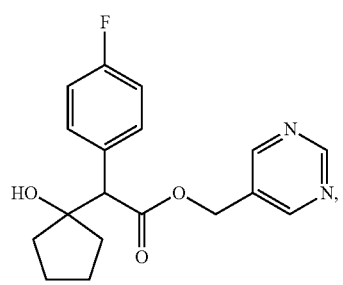
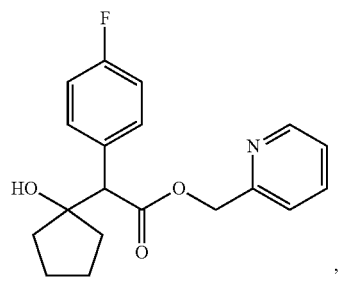
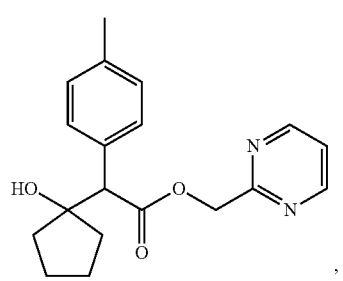

-continued
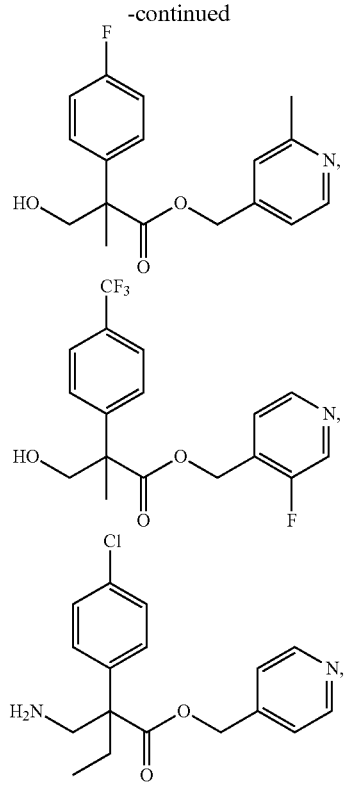
-continued
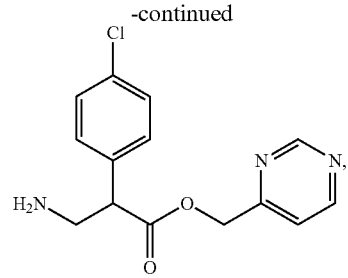
or a solvate, polymorph or a pharmaceutically acceptable salt thereof.
2. The compound of claim 1, wherein the compound is:
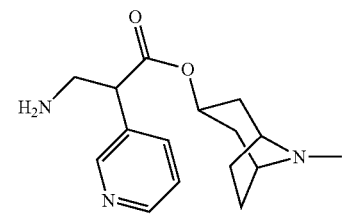 [SMILES: CN1C2CCC1CC(OC(=O)C(CN)c1cccnc1)C2]
or a solvate, polymorph thereof, or a pharmaceutically acceptable salt thereof.
* * * * *